(12) United States Patent
Welch

(10) Patent No.: US 7,884,076 B2
(45) Date of Patent: Feb. 8, 2011

(54) MULTIPEPTIDE REGIMEN FOR THE TREATMENT OF AUTISTIC SPECTRUM, BEHAVIORAL, EMOTIONAL AND VISCERAL INFLAMMATION/AUTOIMMUNE DISORDERS

(75) Inventor: Martha G. Welch, New York, NY (US)

(73) Assignee: The Trustees of Columbia University In the City of New York, New York, NY (US)

( * ) Notice: Subject to any disclaimer, the term of this patent is extended or adjusted under 35 U.S.C. 154(b) by 69 days.

(21) Appl. No.: 10/799,941

(22) Filed: Mar. 11, 2004

(65) Prior Publication Data

US 2005/0201998 A1    Sep. 15, 2005

Related U.S. Application Data

(60) Provisional application No. 60/518,389, filed on Nov. 6, 2003.

(51) Int. Cl.
*A61K 38/11*    (2006.01)
(52) U.S. Cl. .................................................... 514/15
(58) Field of Classification Search ...................... None
See application file for complete search history.

(56) References Cited

U.S. PATENT DOCUMENTS

2006/0105939 A1 *    5/2006    Hollander ....................... 514/2

FOREIGN PATENT DOCUMENTS

DE    4229880 A1 *    3/1994

OTHER PUBLICATIONS

Mayo Clinic. "CREST syndrome" internet document <http://www.mayoclinic.com/health/crest-syndrome/DS00580/DSECTION=8>, Jun. 3, 2005, 2 pages; accessed Aug. 24, 2006.*
Progressive Systemic Sclerosis (PSS) in The Merck Manual 16th edition (1992) R. Berkow, ed., pp. 1321-1323.*
NIH News Alert. "The Use of Secretin to Treat Autism" internet document <http://www.nichd.nih.gov/new/releases/secretin.cfm> Aug. 17, 2001, 2 pages; accessed Aug. 24, 2006.*
"What drugs are used to treat autism?" internet document <http://autism.about.com/od/treatmentoptions/f/drugsfaq.htm> accessed Aug. 24, 2006, 1 page.*
C.R. Ellis, et al. "Autism" internet document <http://www.emedicinehealth.com/script/main/art.asp?articlekey=59039&pf=3&page=2> last edited Oct. 21, 2005, 11 pages; accessed Aug. 24, 2006.*
IBS and IBD: Two very different disorders. Internet document <http://www.ccfa.org/printview?pageUrl=/about/news/ibsoribd> posted Oct. 6, 2005, 3 pages; accessed Aug. 24, 2006.*
INIVRASE fact sheet. Roche Laboratories, Inc.(2005) 32 pages.*
E. Swain. Pharmaceutical and Medical Packaging News (1999) 4 pages.*
PIERCE Technical Resource Sheet TR0043.0 "Protein Stability and Storage" Jun. 2003, 3 pages.*
Autism FAQ- Treatment. internet document <http://www.autism-resources.com/autismfaq-trea.html.*
E. Hollander et al. Neuropsychopharmacology. (Jan. 2003); 28(1), pp. 193-198.*
Abad C, Martinez C, Juarranz MG, Arranz A, Leceta J, Delgado M, Gomariz RP. Therapeutic effects of vasoactive intestinal peptide in the trinitrobenzene sulfonic acid mice model of Crohn's disease. Gastroenterology. Apr. 2003,124(4).
Anisman H, Merali Z. Cytokines, stress and depressive illness: brain-immune interactions. Ann Med. 2003;35(1):2-11.
Armando I, Carranza A, Nishimura Y, Hoe KL, Barontini M, Terron JA, Falcon-Neri A, Ito T, Juorio AV, Saavedra JM. (2001) Peripheral administration of an angiotensin II AT(1) receptor antagonist decreases the hypothalamic-pituitary-adrenal response to isolation stress. Endocrinology. Sep.;142(9):3880-9.
Aylward EH, Minshew NJ, Goldstein G, Honeycutt NA, Augustine AM, Yates KO, Barta PE, Pearlson GD. MRI volumes of amygdala and hippocampus in non-mentally retarded autistic adolescents and adults. Neurology. Dec. 10, 1999; 53(9): 2145-50.
Baker H, Joh TH, Ruggiero DA, Reis DJ. Variations in number of dopamine neurons and tyrosine hydroxylase activity in hypothalamus of two mouse strains. J Neurosci. Apr. 1983;3(4):832-43.
Baron-Cohen S, Ring HA, Wheelwright S, Bullmore ET, Brammer MJ, Simmons A, Williams SC. Social intelligence in the normal and autistic brain: an fMRI study. Eur J Neurosci. Jun. 1999; 11(6):1891-8.
Bauman M, Kemper TL. Histoanatomic observations of the brain in early infantile autism. Neurology. Jun. 1985; 35(6): 866-74.
Bayliss WM and Starling EH (1902) The mechanism of pancreatic secretion. J Physiol (Lond) 28, 325-353.
Bitton A, Sewitch MJ, Peppercorn MA, deB Edwardes MD, Shah S, Ransil B, Locke SE. Psychosocial determinants of relapse in ulcerative colitis: a longitudinal study. Am J Gastroenterol. Oct. 2003;98(10):2203-8.
Blair HT, Schafe GE, Bauer EP, Rodrigues SM, LeDoux JE. Synaptic plasticity in the lateral amygdala: a cellular hypothesis of fear conditioning. Learn Mem. Sep.-Oct. 2001;8(5):2.

(Continued)

*Primary Examiner*—Andrew D Kosar
(74) *Attorney, Agent, or Firm*—Wilmer Cutler Pickering Hale and Dorr LLP

(57) ABSTRACT

The present invention provides compositions and methods for preventing and treating gastrointestinal disorders by administering to a subject an effective amount of secretin either alone or in combination with an effective amount of oxytocin. The invention also provides compositions and methods for preventing and treating central nervous system disorders by administering to a subject an effective amount of secretin in combination with an effective amount of oxytocin. The invention further provides compositions and methods for treating and preventing a variety of autoimmune diseases by administering to a subject an effective amount of secretin in combination with an effective amount of oxytocin. Additionally, the invention provides compositions and methods for preventing and treating pain by administering to a subject using a combination of an effective amount of secretin and an effective amount of oxytocin. The invention also provides kits for use in treating and/or preventing gastrointestinal disorders, central nervous system disorders, autoimmune diseases and pain comprising a combination of secretin and oxytocin.

22 Claims, 25 Drawing Sheets
(14 of 25 Drawing Sheet(s) Filed in Color)

OTHER PUBLICATIONS

Bregonzio C, Armando I, Ando H, Jezova M, Balardi G, Saavedra JM. (2003) Anti-inflammatory effects of angiotensin II AT1 receptor antagonism prevent stress-induced gastric injury. Am J Physiol Gastrointest Liver Physiol. Aug. 2003;285(2):G414-23.

Chariton CG, Miller RL, Crawley JN, Handelmann GE, O'Donohue TL. Secretin modulation of behavioral and physiological functions in the rat. Peptides. Sep.-Oct. 1983;4(5):739-42.

Charlton CG, O'Donohue TL, Miller RL, Jacobowitz DM. Secretin immunoreactivity in rat and pig brain. Peptides. 1981;2 Suppl 1:45-9.

Chugani DC, Muzik O, Rothermel R, Behen M, Chakraborty P, Mangner T, da Silva EA, Chugani HT. Altered serotonin synthesis in the dentatothalamocortical pathway in autistic boys. Ann Neurol. Oct. 1997;42(4):666-9.

Chugani DC, Sundram BS, Behen M, Lee ML, Moore GJ. (1999) Evidence of altered energy metabolism in autistic children. Prog Neuropsychopharmacol Biol Psychiatry. May;23(4):635-41.

Comi AM, Zimmerman AW, Frye VH, Law PA, Peeden JN. Familial clustering of autoimmune disorders and evaluation of medical risk factors in autism. J Child Neurol. Jun. 1999; 14(6): 388-94.

Cook EH. Autism: review of neurochemical investigation. Synapse. 1990; 6(3): 292-308.

Cushing BS, Yamamoto Y, Hoffman GE, Carter CS. Central expression of c-Fos in neonatal male and female prairie voles in response to treatment with oxytocin. Brain Res Dev Brain Res. Jul. 12, 2003; 143(2): 129-36.

Dantzer R. Cytokine-induced sickness behavior: mechanisms and implications.Ann N Y Acad Sci. Mar. 2001;933:222-34.

Delgado M, Leceta J, Sun W, Gomariz RP, Ganea D. VIP and PACAP induce shift to a Th2 response by upregulating B7.2 expression. Ann N Y Acad Sci. 2000; 921: 68-78.

Dohi T, Fujihashi K, Rennert PD, Iwatani K, Kiyono H, McGhee JR. Hapten-induced colitis is associated with colonic patch hypertrophy and T helper cell 2-type responses. J Exp Med. Apr. 19, 1999; 189(8): 11 169-80.

Drossman DA, Ringel Y. Vogt BA, Leserman J, Lin W, Smith JK, Whitehead W. Alterations of brain activity associated with resolution of emotional distress and pain in a case of severe irritable bowel syndrome. Gastroenterology. Mar. 2003;124(3):754-61.

Farmer MA, Sundberg JP, Bristol IJ, Churchill GA, Li R, Elson CO, Leiter EH. A major quantitative trait locus on chromosome 3 controls colitis severity in IL-10-deficient mice. Proc Natl Acad Sci U S A. Nov. 20, 2001; 98(24): 13820-5. Epub Nov. 13, 2001.

Farrell RJ. Epidermal growth factor for ulcerative colitis. N Engl J Med. Jul. 24, 2003;349(4):395-7.

Francis DD, Diorio J, Plotsky PM, Meaney MJ. Environmental enrichment reverses the effects of maternal separation on stress reactivity. J Neurosci. Sep. 15, 2002;22(18):7840-3.

Francis DD, Young LJ, Meaney MJ, Insel TR. Naturally occurring differences in maternal care are associated with the expression of oxytocin and vasopressin (V1a) receptors: gender differences. J Neuroendocrinol. May 2002; 14(5): 34.

Gandhi S, Tsueshita T, Onyuksel H, Chandiwala R, Rubinstein 1. (2002) Interactions of human secretin with sterically stabilized phospholipid micelles amplify peptide-induced vasodilation in vivo. Peptides. ug;23(8):1433-9.

Gassull MA. Nutrition and inflammatory bowel disease: its relation to pathophysiology, outcome and therapy. Dig Dis. 2003; 21(3): 220-7.

Guilloteau P, Chayvialle JA, Toullec R, Grongnet JF, Bernard C. Early-life patterns of plasma gut regulatory peptide levels in calves: effects of the first meals. Biol Neonate. 1992;61(2):103-9.

Gupta S, Aggarwal S, Rashanravan B, Lee T. Th1- and Th2-like cytokines in CD4+ and CD8+ T cells in autism. JNeuroimmunol. May 1, 1998; 85(1): 106-9.

Guth PH, Smith E. The effect of gastrointestinal hormones on the gastric microcirculation. Gastroenterology. Sep. 1976;71(3):435-8.

Gutkowska J, Jankowski M, Mukaddam-Daher S, McCann SM. Oxytocin is a cardiovascular hormone. Braz J Med Biol Res. Jun. 2000;33(6):625-33.

Hart A, Kamm MA. Review article: mechanisms of initiation and perpetuation of gut inflammation by stress. Aliment Pharmacol Ther. Dec. 2002; 16(12):2017-28.

Haznedar MM, Buchsbaum MS, Wei TC, Hof PR, Cartwright C, Bienstock CA, Hollander E. (2000) Limbic circuitry in patients with autism spectrum disorders studied with positron emission tomography and magnetic resonance imaging. Am J Psychiatry. Dec.; 157.

Helou CM, Imbert-Teboul M, Doucet A, Rajerison R, Chollet C, Alhenc-Gelas F, Marchetti J. (2003) Angiotensin receptor subtypes in thin and muscular juxtamedullary efferent arterioles of rat kidney. Am J Physiol Renal Physiol. Sep.;285(3):F507-14.

Higa KT, Mori E, Viana FF, Morris M, Michelini LC. Baroreflex control of heart rate by oxytocin in the solitary-vagal complex. Am J Physiol Regul Integr Comp Physiol. Feb. 2002;282(2):R537-45.

Hollander E, Novotny S, Hanratty M, Yaffe R, DeCaria CM, Aronowitz BR, Mosovich S. (2003) Oxytocin infusion reduces repetitive behaviors in adults with autistic and Asperger's disorders. Neuropsychopharmacology. Jan.;28(1):193-8.

Horvath K, Papadimitriou JC, Rabsztyn A, Drachenberg C, Tildon JT. (1999) Gastrointestinal abnormalities in children with autistic disorder. J Pediatr. Nov.; 135(5):559-63.

Horvath K, Stefanatos G, Sokolski KN, Wachtel R, Nabors L, Tildon JT. (1998) Improved social and language skills after secretin administration in patients with autistic spectrum disorders. J Assoc Acad Minor Phys.; 9(1): 9-15.

Iijima H, Takahashi I, Kishi D, Kim JK, Kawano S, Hori M, Kiyono H. (1999) Alteration of interleukin 4 production results in the inhibition of T helper type 2 cell-dominated inflammatory bowel disease in T cell receptor alpha chain-deficient mice. J Exp Med. Sep. 6; 190(5): 607-15.

Jyonouchi H, Sun S, Itokazu N. Innate immunity associated with inflammatory responses and cytokine production against common dietary proteins in patients with autism spectrum disorder. Neuropsychobiology. 2002;46(2):76-84.

Jyonouchi H, Sun S, Le H. Proinflammatory and regulatory cytokine production associated with innate an adaptive immune responses in children with autism spectrum disorders and developmental regression. J Neuroimmunol. Nov. 1, 2001;120(1-2):170-9.

Konturek SJ, Zabielski R, Konturek JW, Czarnecki J. Neuroendocrinology of the pancreas; role of brain-gut axis in pancreatic secretion. Eur J Pharmacol. Nov. 14, 2003;481(1):1-14.

Kucharzik T, Lugering N, Adolf M, Domschke W, Stoll R. Synergistic effect of immunoregulatory cytokines on peripheral blood monocytes from patients with inflammatory bowel disease. Dig Dis Sci. Apr. 1997; 42(4): 805-12.

Leong DS, Terron JA, Falcon-Neri A, Armando I, Ito T, Johren 0, Tonelli LH, Hoe KL, Saavedra JM. (2002) Restraint stress modulates brain, pituitary and adrenal expression of angiotensin II AT(IA), AT(IB) and AT(2) receptors. Neuroendocrinology. Apr.;75(4):227-40.

Levitt JG, O'Neill J, Blanton RE, Smalley S, Fadale D, McCracken JT, Guthrie D, Toga AW, Alger JR. Proton magnetic resonance spectroscopic imaging of the brain in childhood autism. Biol Psychiatry. Dec. 15, 2003;54(12)1355-66.

Linthorst AC, Reul JM. Brain neurotransmission during peripheral inflammation. Ann N Y Acad Sci. May 1, 1998;840:139-52.

Luna B, Minshew NJ, Garver KE, Lazar NA, Thulborn KR, Eddy WF, Sweeney JA. Neocortical system abnormalities in autism: an fMRI study of spatial working memory. Neurology. Sep. 24, 2002;59(6):834-40.

Mack SO, Kc P, Wu M, Coleman BR, Tolentino-Silva FP, Haxhiu MA. Paraventricular oxytocin neurons are involved in neural modulation of breathing. J Appl Physiol. Feb. 2002;92(2):826-34.

Malek-Ahmadi P. Cytokines and etiopathogenesis of pervasive developmental disorders. Med Hypotheses. Mar. 2001;56(3):321-4.

Matthiesen AS, Ransjo-Arvidson AB, Nissen E, Uvnas-Moberg K. Postpartum maternal oxytocin release by newborns: effects of infant hand massage and sucking. Birth. Mar. 2001;28(1):13-9.

McEwen BS. The neurobiology of stress: from serendipity to clinical relevance. Brain Res. Dec. 15, 2000;886(1-2):172-189.

Meaney MJ, Aitken OH, van Berkel C, Bhatnagar S, Sapolsky RM. Effect of neonatal handling on agerelated impairments associated with the hippocampus. Science. Feb. 12, 1988;239(4841 Pt 1):766-8.

Michelini LC, Marcelo MC, Amico J, Morris M. Oxytocinergic regulation of cardiovascular function: studies in oxytocin-deficient mice. Am J Physiol Heart Circ Physiol. Jun. 2003;284(6):H2269-76.

Nelson KB, Grether JK, Croen LA, Dambrosia JM, Dickens BF, Jelliffe LL, Hansen RL, Phillips TM. Neuropeptides and neurotrophins in neonatal blood of children with autism or mental retardation. Ann Neurol. May 2001; 49(5): 597-606.

Palecek J, Willis WD. The dorsal column pathway facilitates visceromotor responses to colorectal distention after colon inflammation in rats. Pain. Aug. 2003;104(3):501-7.

Palmer GC. Neurochemical coupled actions of transmitters in the microvasculature of the brain. Neurosci Biobehav Rev. 1986 Summer; 10(2):79-101.

Penny WJ, Mayberry JF, Aggett PJ, Gilbert JO, Newcombe RG, Rhodes J. Relationship between trace elements, sugar consumption, and taste in Crohn's disease. Gut. Apr. 1983,24(4):288-92.

Peterson G, Mason GA, Barakat AS, Pedersen CC. Oxytocin selectively increases holding and licking of neonates in preweanling but not postweanling juvenile rats. Behav Neurosci. Jun. 1991; 105(3): 470-7.

Porter RH, Winberg J. Unique salience of maternal breast odors for newborn infants. Neurosci Biobehav Rev. 1999;23(3):439-49.

Rominger JM, Chey WY, Chang TM. Plasma secretin concentrations and gastric pH in healthy subjects and patients with digestive diseases. Dig Dis Sci. Jul. 1981; 26(7): 591-7.

Saitoh 0, Karns CM, Courchesne E. Development of the hippocampal formation from 2 to 42 years: MRI evidence of smaller area dentata in autism. Brain. Jul. 2001; 124(Pt 7): 1317-24.

Sica AL, Greenberg HE, Scharf SM, Ruggiero DA. Chronic-intermittent hypoxia induces immediate early gene expression in the midline thalamus and epithalamus. Brain Res. Nov. 17, 2000;883(2):224-8.

Sidman R.L., Angevine J.B., Jr., Pierce E.T., (1971) Atlas of the Mouse Brain and Spinal Cord. Harvard University Press. Cambridge.

Siegel BV Jr, Asarnow R, Tanguay P, Call JD, Abel L, Ho A, Lott I, Buchsbaum MS. Regional cerebral glucose metabolism and attention in adults with a history of childhood autism. J Neuropsychiatry Clin Neurosci. 1992 Fall; 4(4): 406-14.

Spencer DM, Veldman GM, Banerjee S, Willis J, Levine AD. Distinct inflammatory mechanisms mediate early versus late colitis in mice. Gastroenterology. Jan. 2002; 122(1): 94-105.

Sweeten TL, Bowyer SL, Posey DJ, Halberstadt GM, McDougle CJ. Increased prevalence of familial autoimmunity in probands with pervasive developmental disorders. Pediatrics. Nov. 2003; 112(5): e420.

Tache Y, Garrick T, Raybould H. Central nervous system action of peptides to influence gastrointestinal motor function. Gastroenterology. Feb. 1990;98(2):517-28.

Torrente F, Ashwood P, Day R, Machado N, Furtano RI, Anthony A, Davies SE, Wakefield AJ, Thomson MA, Walker-Smith JA, Murch SH. (2002) Small intestinal enteropathy with epithelial IgG and complement deposition in children with regressive autism. Mol Psychiatry;7(4):375-82, 334.

Traub RJ, Silva E, Gebhart GF. Solodkin A. Noxious colorectal distention induced-c-Fos protein in limbic brain structures in the rat. Neurosci Lett. Sep. 13, 1996;215(3):165-8.

Uno H, Tarara R, Else JG, Suleman MA, Sapolsky RM. (1989) Hippocampal damage associated with prolonged and fatal stress in primates. J Neurosci. May;9(5):1705-11.

Uvnas-Moberg K. Oxytocin linked antistress effects—the relaxation and growth response. Acta Physiol Scand Suppl. 1997;640:38-42.

Walker JK, Premont RT, Barak LS, Caron MG, Shetzline MA. (1999) Properties of secretin receptor internalization differ from those of the beta(2)-adrenergic receptor. J Biol Chem. Oct. 29;274(44):31515-23.

Welch MG, Chaput P. Mother-child holding therapy and autism. Pa Med. Oct. 1988;91(10):33-8.

Welch MG, Keune JD, Welch-Horan TB, Anwar N, Anwar M, Ruggiero DA. Secretin activates visceral brain regions in the rat including areas abnormal in autism. Cell Mol Neurobiol. Oct. 2003; 23(4-5): 817-37.

Welch MG, Welch-Horan TB, Keune JD, Anwar N, Anwar M, Ludwig RJ, Ruggiero DA. Secretin: hypothalamic distribution and hypothesized neuroregulatory role in autism. Cell Mol Neurobiol. Apr. 2004; 24(2): 167-89.—(not available).

Welch MG. (1983b) Retrieval from autism through mother-child holding therapy. In Call JD, Galenson E, Tyson RL, eds. Frontiers of Infant Psychiatry. 1983b New York: Basic Books.

Welch MG. Appendix I: retrieval from autism through mother-child holding therapy in Tinbergen N and Tinbergen EA, 'Autistic' Children: New Hope for a Cure. George Allen & Unwin. London 1983a. 322-336.

Welch MG. Toward prevention of developmental disorders. Pa Med. Mar. 1987;90(3):47-52.

Welch, M.G. (1983a) Retrieval from autism through mother-child holding. In Tinbergen N and EA. Autistic Children—New Hope for a Cure. London and Boston: George, Allen and Unwin.

White JF. (2003) Intestinal pathophysiology in autism. Exp Biol Med (Maywood). Jun.;228(6):639-49.

Yaniv D, Schafe GE, LeDoux JE, Richter-Levin G. A gradient of plasticity in the amygdala revealed by cortical and subcortical stimulation, in vivo. Neuroscience. 2001;106(3):613-20.

Yaraee R, Ebtekar M. Ahmadiani A, Sabahi F. Neuropeptides (SP and CGRP) augment pro-inflammatory cytokine production in HSV-infected macrophages. Int Immunopharmacol. Dec. 2003; 3(13-14): 1883-7.

Yirmiya N, Pilowsky T, Nemanov L, Arbelle S, Feinsilver T, Fried I, Ebstein RP. Evidence for an association with the serotonin transporter promoter region polymorphism and autism. Am J Med Genet. May 8, 2001; 105(4): 381.

Welch et al.: Neuropeptide Treatment of Genetic and Acquired IBD and Concomitant Brain Activation in Areas Abnormal in Autism, Autism Abstracts presented at Society for Neuroscience, Nov. 8-12, 2003, New Orleans, LA, p. 9.

International Search Report of International Application No. PCT/US2005/008277.

Asarian, Lori et al. "Stimuli from Conspecifics Influence Brain Mast Cell Population in Male Rats." Hormones and Behavior, 42:1-12. (2002).

Bauminger, Nirit and Connie Kasari. "Loneliness and Friendship in High-Functioning Children with Autism." Child Development, 71(2): 447-456. (Apr. 2000).

Bradesi, Sylvie et al. "Inflammatory bowel disease and Irritable bowel syndrome: separate or unified?" Curr. Opin. Gastroentereology, 19:336-342. (2003).

Breiner, Jeri and Steven Beck. "Parents as Change Agents in the Management of their Developmentally Delayed Children's Noncompliant Behaviors: A Critical Review." Applied Research in Mental Retardation, 5:259-278. (1984).

Buchsbaum, Monte S. et al. "Effect of fluoxetine on regional cerebral metabolism in autistic spectrum disorders: a pilot study." Int'l Journal of Neuropsychopharmacology, 4:119-125. (2001).

International Search Report of International Application No. PCT/US2005/008277.

Eskandari, Farideh et al. "Neural Immune pathways and their connection to inflammatory diseases." Arthritis Res Ther., 5:251-265. (2003).

Friebe-Hoffmann, Ulrike et al. "Effect of IL-1β and IL-6 on Oxytocin Secretion in Human Uterine Smooth Muscle Cells." AJRI, 46:226-231. (2001).

Gershon, Michael D. "The Second Brain." HarpersCollins, New York. (1998).

Horvath, Karoly and Jay A. Perman. "Autism and Gastrointestinal Symptoms." Current Gastroenterology Reports, 4:251-258. (2002).

Kuntz, A. et al. "Effects of Secretin on Extracellular Amino Acid Concentrations in Rat Hippocampus." Journal of Neural Transmission. 111:931-939. (2004).

Leventhal, Bennett L. et al. "Relationships of Whole Blood Serotonin and Plasma Norepinephrine Within Families." Journal of Autism and Development Disorders, 20(4):499-511. (1990).

Lightdale, Jenifer R. et al. "Gastrointestinal Symptoms in Autistic Children." Clinical Perspectives in Gastroenterology, pp. 56-58. (2001).

Lupoli, Berit et al. "Effect of suckling on the release of oxytocin, prolactin, cortisol, gastrin, cholecystokinin, somatostatin and insulin in dairy cows and their calves." Journal of Dairy Research, 68:175-187. (2001).

Manfredini, Rossella et al. "Development of an IL-6 antagonist peptide that induces apoptosis in 7TD1 cells." Peptides, 24:1207-1220. (2003).

McEwen, Bruce S. "Early Life Influences on Life-Long Patterns of Behavior and Health," Mental Retardation and Developmental Disabilities Research Reviews, 9:149-154. (2003).

Paxinos, George and Charles Watson. "The Rat Brain in Stereotaxic Coordinates." Elsevier Academic Press, Burlington, MA. (2005).

Pedersen, Cod A. and Maria L. Boccia. "Oxytocin Links Mothering Received, Mothering Bestowed and Adult Stress Responses." Stress, 5(4):259-267. (2002).

Popovic, Miroljub et al. "Immune Responses in Nucleus Basalis Magnocellularis-Lesioned Rats Exposed to Chronic Isolation Stress." Intern. J. Neuroscience, 100:125-131. (2000).

Porter, Richard H. "Olfaction and human kin recognition." Genetica, 104:259-263. (1999).

Rumsey, Judith M. and Monique Ernst. "Functional Neuroimaging of Autistic Disorders." Mental Retardation and Developmental Disabilities Research Reviews, 6:171-179. (2000).

Saitoh, O. et al. "Cross-sectional area of the posterior hippocampus in autistic patients with cerebellar and corpus callosum abnormalities." Neurology, 45:317-324. (1995).

Swanson, L. W. "Brain Maps: Structure of the Rat Brain." Elsevier, Amsterdam, The Netherlands. (1998).

Warren, Reed P. et al. "Brief Report: Immunoglobulin A Deficiency in a Subset of Autistic Subjects." Journal of Autism and Developmental Disorders, 27(2):187-192. (1997).

Welch, M. G. et al. "Neuropeptide Treatment of Genetic and Acquired IBD and Concomitant Brain Activation in Areas Abnormal in Autism." Society for Neuroscience. (2003).

Welch, Martha G. "Holding Time: How to Eliminate Conflict, Temper Tantrums, and Sibling Rivalry and Raise Happy, Loving, Successful Children." Century, London, Great Britain. (1989).

Welch, Martha G. et al. "Outcomes of Prolonged Parent-Child Embrace Therapy among 102 Children with Behavioral Disorders." Complementary Therapies in Clinical Practice, 12:3-12. (2006).

Welch, Martha G. et al. "Holding Time: What, Where, When, How and Why." Proceedings of the First International Congress or Holding Therapy, Regensburg, Germany. (1989).

* cited by examiner

Central Amygdala (10x) - IBD Untreated

Central Amygdala (10x) –
IBD VIP & Oxytocin Treated

Somatosensory area (4x) - IBD Untreated

Somatosensory area (4x) –
IBD VIP & Oxytocin Treated

Paraventricular Hypothalamus (10x) –
IBD Untreated

Paraventricular Hypothalamus (10x) - IBD VIP
& Oxytocin Treated

MULTIPEPTIDE REGIMEN FOR THE TREATMENT OF AUTISTIC SPECTRUM, BEHAVIORAL, EMOTIONAL AND VISCERAL INFLAMMATION/AUTOIMMUNE DISORDERS

CROSS-REFERENCE TO RELATED APPLICATIONS

This application claims priority to U.S. provisional application Ser. No. 60/518,389, filed on Nov. 6, 2003.

STATEMENT OF GOVERNMENT INTEREST

This invention was made with government support under NIH Grant No. RO1 36363 (DAR). As such, the United States government may have certain rights in this invention.

BACKGROUND OF THE INVENTION

Autism is a disorder defined by both American and International diagnostic systems (i.e., the Diagnostic and Statistical Manual of Mental Disorders, 4th edition (DSM-IV) and World Health Organization: International Classification of Diseases, Tenth revision (ICD-10)). Autism is the third most prevalent developmental disability in the United States, currently affecting over one-half million people. The disorder is typically characterized by multiple distortions in the development of basic psychological functions that are involved in the development of social skills and verbal and non-verbal communication, such as attention, perception reality testing and motor movement. Children and adults suffering from autism may exhibit repeated body movements, unusual responses to people or attachments to objects and may resist any changes in routines. In some cases, those suffering from the disorder may exhibit aggressive or self-injurious behavior. Additionally, many patients diagnosed with Autism suffer from primary diffuse gastrointestinal problems such as protracted diarrhea and constipation. The specific cause of Autism is not known and there is no known cure for the disorder. Additionally, conventional methods of treatment, including dietary alteration, behavioral modification, and medication, have proven unsuccessful in allowing such children and adults to become symptom, or disorder free.

To date, there is no comprehensive treatment for the broad range of autistic symptomatology: seizures (Park 2003); attentional/arousal dysregulation, ADHD (Booth, et al., 2003); obsessive-compulsive disorder (OCD) (Hollander, et al., 2003a); stereotypies (Militemi, et al., 2002); social isolation (Iqbal 2002); attachment disorders (Tinbergen and Tinbergen 1983, Kobayashi, et al., 2001); face recognition deficits (Ogai, et al., 2003, Schultz, et al., 2003); gaze aversions (Richer, et al., 1976); gastrointestinal disorders (Horvath, et al., 1998, Horvath, et al., 2002, Torrente, et al., 2002, Gershon 2003 personal communication); and altered heart rate variability (Graveling and Brooke 1978, Corona, et al., 1998). Current drugs directed at treating these symptoms have long-term side effects and efficacy not far above placebo rates (Posey, et al., 2000), resulting in motivation to seek new treatments.

Gastrointestinal (GI) disorders, including inflammatory bowel diseases (IBDs), affect millions of people of all ages world wide, and the social and economic costs of these disorders are enormous. The symptoms of GI disorders range from inconvenience and mild discomfort to total incapacitation. For those with severe symptoms, GI disorders can be debilitating, rendering participation in social and professional activities impossible. Because much remains unknown about GI disorders, misdiagnosis and ineffective treatment for these disorders is common. For example, women suffering from irritable bowel syndrome (IBS) have an increased risk of unnecessary surgery including unnecessary hysterectomy and ovarian surgery. Longstreth G F, "Irritable Bowel Syndrome: A Multibillion-Dollar Problem" *Gastroenterology*, 109:2029-2042 (1995). Accordingly, a current need exists for new and better methods for improving the prognosis of patients suffering from GI disorders.

The pathogenesis of inflammatory bowel diseases (IBDs) is multifactorial, involving immune dysfunctions, specifically a dysregulation of Th1/Th2 type cytokines (Iijima, et al., 1999). Alteration of interleukin 4 production results in the inhibition of T helper type 2 cell-dominated inflammatory bowel disease in T cell receptor alpha chain-deficient mice. *J. Exp. Med.*, 190(5): 607-15; Dohi, et al. Hapten-induced colitis is associated with colonic patch hypertrophy and T helper cell 2-type responses. *J. Exp. Med.*, 1999; 189(8): 1169-80; Kucharzik, et al., Synergistic effect of immunoregulatory cytokines on peripheral blood monocytes from patients with inflammatory bowel disease. *Dig. Dis. Sci.*, 1997, 42(4):805-12). Such Th1/Th2 dysregulation has been suggested in the pathogenesis of autism as well. (Gupta, et al., 1998, 85(1): 106-9.) Interestingly, a shift from Th1 to predominantly Th2 cytokines is induced by vasoactive intestinal peptide (VIP) (Dohi, et al.). Elevated levels of plasma VIP in neonates later diagnosed with autism were reported in a large prospective study (Dohi, et al.). Some cases of autism are reported with onset subsequent to an IBD episode. (Lightdale, et al., Gastronintestinal symptoms in autistic children, *Clin. Perspec. Gastroenterol.*, 156-58 (2001); White, Intestinal pathophysiolgy in autism, *Exp. Biol. Med.* (Maywood) (2003) 228(6): 639-49; Horvath, et al., 1999, Gastrointestinal abnormalities in children with autistic disorder; *J. Pediatr.* 135(3):559-63.) Autism is also associated with a high incidence of familial autoimmune disorders (Comi, et al., Familial clusterin of autoimmune disorders and evaluation of medical risk factors in autism, *J. Child. Neurol.*, 1999, 14(6):388-94) and is often associated with a familial finding of elevated plasma levels of serotonin (5HT) (Cook, Autism: review of neurochemical investigation. (Synapse, 1990, 6(3):292-308). The body's predominant source of 5HT is the gastrointestinal tract. (Gershon 1998). The Second Brain: a groundbreaking new understanding of nervous disorders of the stomach and intestine. (New York: Harper Collins, p. 163.) If serum 5HT is elevated, there are abnormalities in the bowel that lead to excessive 5HT release. (Gershon 1998).) Serotonin/secretin co-localization and the number of S cells have been found to be markedly altered in the autistic gut. (Gershon, et al., Personal communication 2003.) Secretin has long been recognized as a gut peptide (Bayliss, et al., 1902). The mechanism of pancreatic secretion (*J. Physiol.* (Lond) 28, 325-353), and more recently as a neuropeptide. (Welch, et al., Secretin: hypothalmamic distribution and hypothesized neuroregulatory role in autism; *Cell. Mol. Neurobiol.*, 2004, 24(2):167-89.)

Recent studies have demonstrated pathology in the gastrointestinal tract of autistic children, including findings of impaired gut/immune system development, altered production of gut/brain peptides, increased intestinal mucosal permeability, and inflammation. (Warren, et al., 1997). Brief report: immunoglobulin: A deficiency in a subset of autistic subjects, *J. Autism. Dev. Disord.*, 27(2): 187-92; Nelson, et al., Neuropeptides and neurotrophins in neonatal blood of children with autism or mental retardation. *Ann. Neurol.*, (2001) 49(5):597-606; Torrente, et al., 2002). Small intestinal enteropathy with epithelial IgG and complement deposition in children with regressive autism. *Mol. Psychiatry;* 7(3): 375-82, 334; White 2003). Intestinal pathophysiology in autism. *Exp. Biol. Med.* (Maywood) 228(6):639-49)). Other results have highlighted the possibility of homeostatic imbalance in autistic children (Chugani, et al., 1999). Evidence of altered energy metabolism in autistic children; *Prog. Neurophsychopharmacol Biol. Psychiatry,* 23(4):635-41), and have called attention to the dysregulation of peptide hormones protective of homeostasis. (Nelson, et al., Neuropeptides and neurotrophins in neonatal blood of children with autism or mental retardation; *Ann. Neurol.* (2001) 49(5):597-606; Hollander, et al., 2003). Oxytocin infusion reduces repetitive behaviors in adults with autistic and Asperger's disorders. *Neuropsychopharmacology,* 28(1): 193-8; Gerson, et al., Personal communication 2003). Thus, effective clinical or pharmacokinetic intervention for autistic symptoms may require a method that acts simultaneously upon gut/brain and on the associated gut/brain stress axis in order to re-establish homeostasis. (Welch, et al., 2003b) Neurohormonal Resolution of Genetic and Acquired IBD and Secondary Brain Activation in Areas Abnormal in Autism, *Neurosci. Abstracts:* 33$^{rd}$ Annual Meeting November 8-12.) Furthermore, cerebral metabolic imbalances in autism have been identified via functional imaging. (Haznedar, et al., 2000). Limbic circuitry in patients with autism spectrum disorders studied with positron emission tomography and magnetic resonance imaging. *Am. J. Psychiatry,* 157(12): 1994 -2001); Naturalistic and/or peptide therapies (Welch 1983a), Retrieval from autism through mother-child holding. In Tinbergen N and EA. Autistic Children—New Hope for a Cure. London and Boston: George, Allen and Unwin; Welch 1983b), Retrieval from autism through mother-child holding therapy. In Call, et al., eds. Frontiers of Infant Psychiatry (1983b) New York: Basic Books; Horvath, et al., 1998). Improved social and language skills after secretin administration in patients with autistic spectrum disorders. *J. Assoc. Acad. Minor Phys.;* 9(1): 9-15; Hollander, et al., 2003) Oxytocin infusion reduces repetitive behaviors in adults with autistic and Asperger's disorders. *Neuropsychopharmacology,* 28(1):193-8; Welch, et al., 2003b) Neurohormonal Resolution of Genetic and Acquired IBD and Secondary Brain Activation in Areas Abnormal in Autism, *Neurosci. Abstracts:* 33$^{rd}$ Annual Meeting November 8-12) may be effective to the extent that they correct such imbalances. Peptide infusions can access the sympathetic ganglia that regulate systemic and cerebral microvasculature (Palmer, Neurochemical coupled actions of transmitter in the microvasculature of the brain, *Neurosci. Biobehav. Rev.* (1986) Summer; 10(2):79-101) and innervate the pineal gland, the richest source of secretin. (Chariton, et al., Secretin immunoreactivity in rat and pig brain, Peptides (1981) 2 Suppl 1:45-9.) Two studies of peptide treatments, epidermal growth factor enemas and systemic VIP, a member of the secretin family, have demonstrated efficacy in ameliorating IBD in humans and in an animal model, respectively (Farrell, Epidermal growth factor for ulcerative colitis, *N. Engl. J. Med.* (2003) 349(4):395 -7; Abad, et al., Therapeutic effects of vasoactive intestinal peptide in the trinitrobenzene sulfonic acid mice model of Chrohn's disease, *Gastroenterology* (2003) 124(4):961-71). However, neither study examined the treatment's effect on the brain.

It remains a major therapeutic challenge to find new effective approaches to improve the diagnosis and treatment of GI and other brain/gut disorders. The etiology of psychiatric disorders such as autism, as well as the link between these psychiatric disorders and gastrointestinal abnormalities remains poorly understood. Accordingly, a need exists for the development of novel therapeutic measures for treating patients with psychiatric and physical illness associated with chronic visceral inflammation.

The rationale for examining peptide treatment for visceral inflammation and its concomitant brain changes emerges from clinical work demonstrating the efficacy of intensive maternal nurturing and from the literature on maternal nurturing in animal models. (Meaney, et al., Effect of neonatal handling on age-related impairments associated with the hippocampus, *Science* (1988) 239(4841 Pt 1):766-8) Clinical work (Tinbergen, et al., 1983, Welch, 1983a,b, 1989) has shown that autistic spectrum disorders are ameliorated by reinstating components of maternal nurturing, including the establishment of synchronous attunement between mother and child (Welch, 1983a,b, 1987, 1988 a, b, 1989, Welch, et al., 1988). Mother/infant interaction appears to be a powerful stimulus to neuropeptide release (Matthiesen, et al., 2001). In clinical practice, autistic children and adopted orphans with severe maternal deprivation syndromes were treated with Prolonged Mother-Child Embrace, an intervention that reinstates specific components of maternal nurturing (holding, embracing, comforting, licking, talking, feeding). This intervention has been reported to resolve behavioral and visceral symptoms and restore normal development. (Welch, Appendix I: retrieval from autism through mother-child holding therapy In Tinbergen, et al., 'Autistic' Children: New Hope for a Cure. George Allen & Unwin, London (1983a.) 322-336; (1983b) Retrieval from autism through mother-child holding therapy, In Call, et al., eds. *Frontiers of Infant Psychiatry* (1983b) New York: Basic Books; Toward prevention of developmental disorders, *Pa Med.* (1987) 90(3):47-52; Welch, Mother-child holding therapy and autism, *Pa Med.* (1988) 91(10):33-8; Welch, Holding Time. New York: Simon and Schuster (1988); Welch (1989) Holding Time: How When Why, Proceedings of the First International Congress of Holding Therapy, Regensberg, Germany; Welch, et al., Outcomes of an intervention to reinstate maternal nurturing among children with behavioral disorders, In prep.) It is hypothesized that the amelioration of symptoms associated with Prolonged Mother-Child Embrace is the result of a testable mechanism involving S and OT up-regulation. (Rominger, et al., Plasma secretin concentrations and gastric pH in healthy subjects and patients with digestive diseases, *Dig. Dis. Sci.* (1981) 26(7): 591-7; Peterson, et al., Oxytocin selectively increases holding and licking of neonates in preweanling but not postweanling juvenile rats, *Behav. Neurosci.* (1991) 105(3): 470-7; Matthiesen, et al., Postpartum maternal oxytocin release by newborns: effects of infant hand massage and sucking, *Birth,* 2001 28(1):13-9; Pedersen, et al., Oxytocin links mothering received, mothering bestowed and adult stress responses, *Stress,* 2002 5(4): 259-67; Francis, et al., Naturally occurring differences in maternal care are associated with the expression of oxytocin and vasopressin (V1a) receptors: gender differences, *J. Neuroendocrinol.* (2002) 14(5): 349-53; Welch, et al., Outcomes of an intervention to reinstate maternal nurturing among children with behavioral disorders, In prep.) Brain/gut neuropeptides contribute to developmental neuroregulation of growth, differentiation and regeneration and to the control of hormone release (Houben, et al., 1994), as well as to the resolution of visceral inflammation and brain activation in brain/gut dysregulation models (Welch, et al., 2002b). These studies indicate that maternal nurturing, as well as interventions that effectively replicate it, involves ameliorative mechanisms that stimulate neuropeptide release.

The inventors' propose that some childhood development abnormalities are spectrum disorders of brain/gut dysregulation that can be ameliorated by naturalistic and/or peptide therapy. Recent research has reveled pathology in the gastrointestinal tract of autistic children extending from the esophagus to the colon. This finding has led to investigations of impaired gut/immune system development, altered production of brain/gut peptides, increased intestinal mucosal permeability, and inflammation (Warren, et al., 1997; Nelson, et al., 2001; Torrente, et al., 2002; White 2003). Other evidence has focused attention on the possibility of homeostatic imbalance, such as altered central and peripheral energy metabolism in autistic children (Chugani, et al., 1999), and dysregulation of peptide hormones that protect homeostasis (Nelson, et al., 2001; Hollander, et al., 2003b; Gershon 2003 personal communication). Effective clinical or pharmacokinetic intervention in autistic symptomatology will require a mechanism that acts simultaneously upon the mind/brain/body stress axis to re-establish homeostasis (Welch, et al., 2002b). Metabolic imbalances in autism have been defined via fMRI (Haznedar, et al., 2000). Naturalistic and/or peptide therapies (Welch 1983a,b; Horvath, et al., 1998; Hollander, et al., 2003b; Welch, et al., 2003b) will be effective to the extent that they address such imbalances.

Psychotherapeutic and pharmacologic measures (Langworthy-Lam, et al., 2002; Diggle, et al., 2003), including peptide neurohormone administration, have been attempted in autistic children, with limited outcomes (Horvath, et al., 1998; Lamson 2001; Sandler, et al., 1999; Coniglio, et al., 2001; Dunn-Geier, et al., 2000; Koren 2001; Lightdale, et al., 2001; Owley, et al., 2001; Roberts, et al., 2001; Kern, et al., 2002). Research supports the importance of peptides in treating behavioral and developmental disorders in autistics: at the bedside, through systemic peptide administration (Horvath, et al., 1998; Hollander, et al., 2003b), in clinical studies (Matthiesen, et al., 2001), and in experimental animals, through reinstating components of maternal nurturing, such as feeding, handling, and licking (Francis, et al., 2002; Bredy, et al., 2003). Experimental models show that feeding and handling ameliorate brain pathology resulting from the social-isolation stress of maternal deprivation (Meaney, et al., 1988, 1991; Anisman, et al., 1998). One peptide in particular, secretin, is associated with feeding and handling, a form of controlled restraint (Lauterbach, et al., 1980; Mineo, et al., 1990).

Secretin is a bioactive peptide endogenously and predominantly synthesized by upper intestinal secretin S cells (Bloom, et al., 1974; Miller, et al., 1978; Strauss, et al., 1978; Paquette, et al., 1982; Chang, et al., 1999). It is also synthesized in mice by the pancreas and colon (Lopez, et al., 1995), and by flora that inhabit the gut (Gauthier, et al., 2003). Whether secretin is synthesized by the forebrain is the subject of this study. Secretin belongs to the secretin/vasoactive intestinal peptide (VIP)/glucagon receptor family with actions at high and low-affinity secretin receptors (Ichihara, et al., 1983). It is a twenty-seven amino acid peptide and an enterogastrone (Jin, et al., 1994; Li, et al., 1998). Secretin receptors couple to G-proteins that stimulate adenylate cyclase and, in turn, lead to the production of cyclic adenosine monophosphate (cAMP) and the stimulation of associated second messenger systems (Harmar 2001). Secretin receptors concentrate in brain regions (Itoh, et al., 1991; Ohta, et al., 1992) that are responsive to intracerebroventricular (i.c.v.) administration of the secretin peptide (Welch, et al., 2002a,b, 2003a), brain regions that are also sites of pathology in autism (Bauman, et al. 1985; Haznedar, et al., 2000; Ogai, et al., 2003; Schultz, et al., 2003).

Secretin's peripheral role as a gastric hormone has long been established (Bayliss and Starling 1902). Less is known about the central actions of secretin. Secretin regulates the central and peripheral stress axes via neurohumoral mechanisms (Ruggiero, et al., 2003; Welch, et al., 2002a,b, 2003a,b) that involve interactions with other signaling systems acting at the level of the hypothalamus, such as secretin/angiotensin (Walker, et al., 1999) and secretin/dopamine (Fuxe, et al., 1979). Secretin functions to modulate HPA stress axis output, and, in contrast to VIP, increases norepinephrine and dopamine turnover in the hypothalamus and median eminence (Fuxe, et al., 1979). Assays finding positive secretin bioactivity, radioimmunoreactivity, or secretin precursor mRNA expression indicated high secretin levels in the hypothalamus and hypophysis, with the preponderance of evidence suggesting that the hypothalamus is a site of origin of endogenous secretin (Fuxe, et al., 1979; Mutt, et al., 1979; Charleton, et al., 1981; O'Donohue, et al., 1981; Samson, et al., 1984; Chang, et al., 1985; Itoh, et al., 1991; Ohta, et al., 1992; Nussdorfer, et al., 2000). Another study assessing the presence of secretin in the rat brain and gut did not find central expression of the bioactive peptide (Kopin, et al., 1990). These studies, however, lacked the single cell resolution needed to precisely delineate the organization of a presumptive secretinergic system. Recently, studies found secretin immunoreactivity in the brain stem and cerebellum (Yung, et al., 2001; Koves, et al., 2002; Ng, et al., 2002), but not in the forebrain. According to Ng, "secretin is only present at detectable levels in the brainstem and cerebellum," although unpublished data suggest "the presence of secretin-producing cells in the cerebral cortex" (Ng, et al., 2002).

The inventors previously tested the hypothesis that secretin regulates stress response patterns via endogenous synthesis along the hypothalamic stress axis. Central secretin administration, i.c.v., activates the area postrema, nucleus of solitary tract (NTS) and its terminal fields, including parabrachial complex, amygdala, and hypothalamus. In addition, secretin activates the visceral thalamus and its insula/orbital and medial prefrontal cortical projection fields, which regulate visceral reflex networks overlapping areas of pathology in autism (Welch, et al., 2002a,b, 2003a). Corroborating some of these results was a report focused on the effects of secretin-induced c-fos gene expression in the amygdala of rats (Goulet, et al., 2003). In a subsequent study, long-term systemic administration of bioactive peptides, including trials with secretin, was found to resolve inflammatory bowel lesions and stress-related effects on specific CNS regions that corresponded to sites of pathology in autism (Welch, et al., 2003b). Systemic exogenous secretin was found to reestablish communicative and affiliative interactions in autistic children with gastrointestinal abnormalities (Horvath, et al., 1998), an observation supported by Lamson (Lamson, et al., 2001). This interest in secretin has led to a current investigative effort to replicate Horvath's novel peptide therapy (Wheeler 2003).

Before the present invention, there was a study demonstrating secretinergic neurons in the forebrain with single cell resolution. The inventors sought to determine whether secretin is synthesized specifically in the forebrain, and whether its specificity and distribution patterns might predict possible interactions of secretin with other hormones involved in stress adaptation. The inventors also investigated whether secretin is synthesized on demand in distinct areas of the HPA stress axis of rats. The central distribution of secretin immunoreactivity in adult male Sprague-Dawley rats was mapped to single-cell resolution using immunocytochemistry.

Although secretin has been identified primarily as a gut hormone, the inventors demonstrated secretinergic immunoreactivity in the hypothalamus of a rat. Secretin also has been shown to have regulatory effects on other organ systems, including the immune system, the central nervous system, the endocrine system, and the respiratory and cardiovascular systems. Van Tol, et al., found that secretin plays a role in the regulation of cellular cytotoxicity against tumor cells. Several studies have reported secretin immunoreactivity in widespread areas of the central nervous system (Chang, et al., 1985; Mutt, et al., 1979; O'Donohue, et al., 1981). Many of the studies have focused particularly on the hypothalamus of various species (Chang, et al., 1985; Charlton, et al., 1981; Mutt, et al., 1979; O'Donohue, et al., 1981; Samson, et al., 1984). Though Kopin, et al. (1990) failed to detect secretin mRNA in the central nervous system (CNS), Itoh, et al., 1991 and Ohta, et al. 1992, reported CNS expression of an mRNA precursor to secretin in the brainstem, thalamus, hypothalamus, and cerebral cortex. In a later study by Nozaki, et al., 2002, secretin was found to bind with specificity and high affinity to the nucleus of the solitary tract, and other regions in the brainstem, thalamus, hypothalamus, and cerebral cortex.

Secretin has long been thought to be a central neuromodulator, prompting several studies examining the actions of secretin injected into the cerebroventricular system: Charlton, et al., 1981, found that intracerebroventricular (i.c.v.) injection of secretin in rats significantly increased defecation, decreased novel-object approaches and open-field locomotor activity, and altered respiration. Weick, et al., 1992, showed that i.c.v. secretin administration inhibited pulsatile luteinizing hormone secretion in the ovariectomized rat. It is conceivable that secretin is synthesized endogenously in the central nervous system (Fuxe, et al., 1979; Itoh, et al., 1991; O'Donohue, et al., 1981; Ohta, et al., 1992). In the cardiovascular system, Gunnes, et al., 1983, found in human subjects that secretin has both iontropic and vasodilating effects. Kitani, et al., 1978, found that secretin increased cardiac output distribution to the stomach, small intestine, and pancreas in rats. In another study, i.c.v. secretin injection induced hypothermia and elevated blood pressure without effects on heart rate (Shido, et al., 1989), although the central sites of action were not identified.

Taken together, these data suggest that secretin is a regulatory hormone with peripheral and central mechanisms of action on multiple organ systems. Although one hypothesized mechanism of secretin is its well-established role in regulating gut function, secretin's regulatory role in other organ systems may underlie some of its ameliorative, though short-lived, actions in autistic children (Horvath, et al., 1998). Earlier studies have localized secretin and its presumptive receptor binding sites in viscerolimbic brain regions involved in central autonomic regulation (Itoh, et al., 1991; Nozaki, et al., 2002; Ohta, et al., 1992). Before the present invention, no study had examined the effects of i.c.v. administration of secretin on visceral brain regions that may be differentially activated.

Oxytocin is a nine amino acid peptide that is synthesized in hypothalamic neurons and transported down axons of the posterior pituitary for secretion into the blood. Oxytocin's physiological roles include stimulation of uterine contraction during childbirth, establishment of maternal behavior, and to cause milk ejection from the breast by contraction of the myoepithelial cells in response to suckling (let down reflex). In males, oxytocin is involved in facilitating sperm transport within the male reproductive system. Acute stress can inhibit oxytocin release. For example, oxytocin neurons are repressed by catecholamines, which are released from the adrenal gland in response to stress. Surprisingly, the inventors of the present invention have discovered that localizations of secretin overlap with those of oxytocin.

The inventors have shown for the first time that peptide therapy, particularly therapy utilizing co-administration of secretin and oxytocin, provides a simultaneous resolution of gut and brain disorders. Gut and brain areas affected by co-administration of secretin and oxytocin overlap those affected in autism, including: thalamus amygdale, HF, Cingulate orbital frontal insula, and PFC.

SUMMARY OF THE INVENTION

In accordance with the present invention, there is provided multi-peptide therapy to effectively treat autism, autistic spectrum disorders and a wide range of other dysregulated behaviors. More specifically, the present invention relates to chemical compounds which deliver a therapeutic dose of a combination of peptides for the treatment of gastrointestinal disorders and other visceral and autoimmune disorders, central nervous system disorders, behavioral disorders and pain. Specifically, the present invention is directed to pharmaceutical compositions comprising a therapeutically effective amount of secretin in combination with a therapeutically effective amount of oxytocin and a pharmaceutically acceptable carrier, as well as to methods of treating gastrointestinal disorders, autoimmune disorders, CNS disorders, and pain by administration of the pharmaceutical composition, optionally in combination with protease inhibitors. The present invention contemplates all forms of the compounds. When the pharmaceutical composition is used as a treatment in a human subject, the total daily dose administered in a single or divided doses may be in amounts, for example from 0.001 to 1000 mg per day and more usually 1 to 100 mg per peptide or dosages in International Units (IU dosage).

The inventors have shown that dysregulated behavior, including brain/gut disorders, may be ameliorated by neuropeptide therapy. Accordingly, the present invention provides compositions and methods for treating and preventing gastrointestinal disorders by administering to a patient a therapeutically effective amount of secretin in combination with a therapeutically effective amount of oxytocin. In an embodiment of the invention, effective amounts of secretin and oxytocin are administered in combination with protease inhibitors. In one embodiment of the invention, the dosage of secretin may be about 0.001 mg/day to about 1000 mg/day. More preferably, the dosage of secretin is about 1 mg/day to 100 mg/day. Likewise, the dosage of oxytocin may be from 0.001 mg/day to about 1000 mg/day, and more usually is delivered in a dosage from about 1 mg/day to about 100 mg/day.

The inventors have demonstrated that the pharmaceutical composition of the present invention is useful in the prevention and treatment of a variety of gastrointestinal disorders including, but not necessarily limited to, irritable bowel disease, irritable bowel syndrome, dyspepsia, diarrhea, incontinence, pelvic floor pain, biliary disorders, abdominal bloating, colitis, constipation and gastrodueodenal disorders. In a preferred embodiment, the disorder treated by the pharmaceutical composition of the invention is irritable bowel disease.

The invention additionally provides compositions and methods for treating various autoimmune diseases by administering to a patient a therapeutically effective amount of secretin in combination with a therapeutically effective amount of oxytocin, optionally in combination with protease inhibitors. The autoimmune disorders include, but are not necessarily limited to, Hashimoto's thyroiditis, pernicious anemia, scleroderma, anti-phospholipid syndrome, autoimmune inner ear disease, Behcet's syndrome, chronic inflammatory polyneuritis, CREST syndrome, Churg Strauss Syndrome, Guillain-Barre syndrome, Goodpasture's syndrome, primary biliary cirrhosis, Crohn's disease, ulcerative colitis, Celiac disease, Wegner's granulomatosis, Sclerosing cholangitis, Addison's disease, type 1 diabetes, rheumatoid arthritis, systemic lupus erythematosus, dermatomyositis, Sjogren's syndrome, lupus erythematosus, multiple sclerosis, myasthenia gravis, Retiter's syndrome and Grave's disease.

The invention also provides compositions and methods for treating various central nervous system disorders, including various behavioral disorders, by administering to a patient a therapeutically effective amount of secretin in combination with a therapeutically effective amount of oxytocin, optionally in combination with protease inhibitors. The central nervous system disorders include, but are not necessarily limited to, autism and autistic spectrum disorders, seizures, conduct disorder, oppositional defiant disorder (ODD), attentional/arousal dysregulation, attention-deficit/hyperactivity disorder (ADHD), obsessive-compulsive disorder, stereotypies, reactive attachment disorder, social isolation, attachment disorders, face recognition deficits, gaze aversions, and altered heart rate variability.

The present invention additionally provides methods and pharmaceutical compositions for treating pain. The pharmaceutical composition can be administered with or without protease inhibitors. The invention further provides kits for use in treating gastrointestinal disorders, central nervous system disorders, autoimmune disorders, and pain, comprising a combination of secretin and oxytocin. The kits can optionally contain one or more protease inhibitors in addition to secretin and oxytocin. The protease inhibitors of the present invention can include, but are not necessarily limited to, Invirase® (saquinavir), Fortovase® (saquinavir), Norvir® (ritonavir), Crixivan® (indinavir), Viracept® (nelfinavir), Agenerase® (amprenavir), Keletra® (lopinavir+ritonavir), Reyataz® (atazanavir) and Lexiva® (fosamprenavir).

DESCRIPTION OF THE FIGURES

The patent or application file contains at one drawing executed in color. Copies of this patent or patent application publication with color drawing(s) will be provided by the Office upon request and payment of the necessary fee.

FIG. 26B shows intralamanar thalamus of IBD secretin-oxytocin treated mouse. Note decrease in thalamic activation after 20 days of treatment with peptides.

Figure 1:
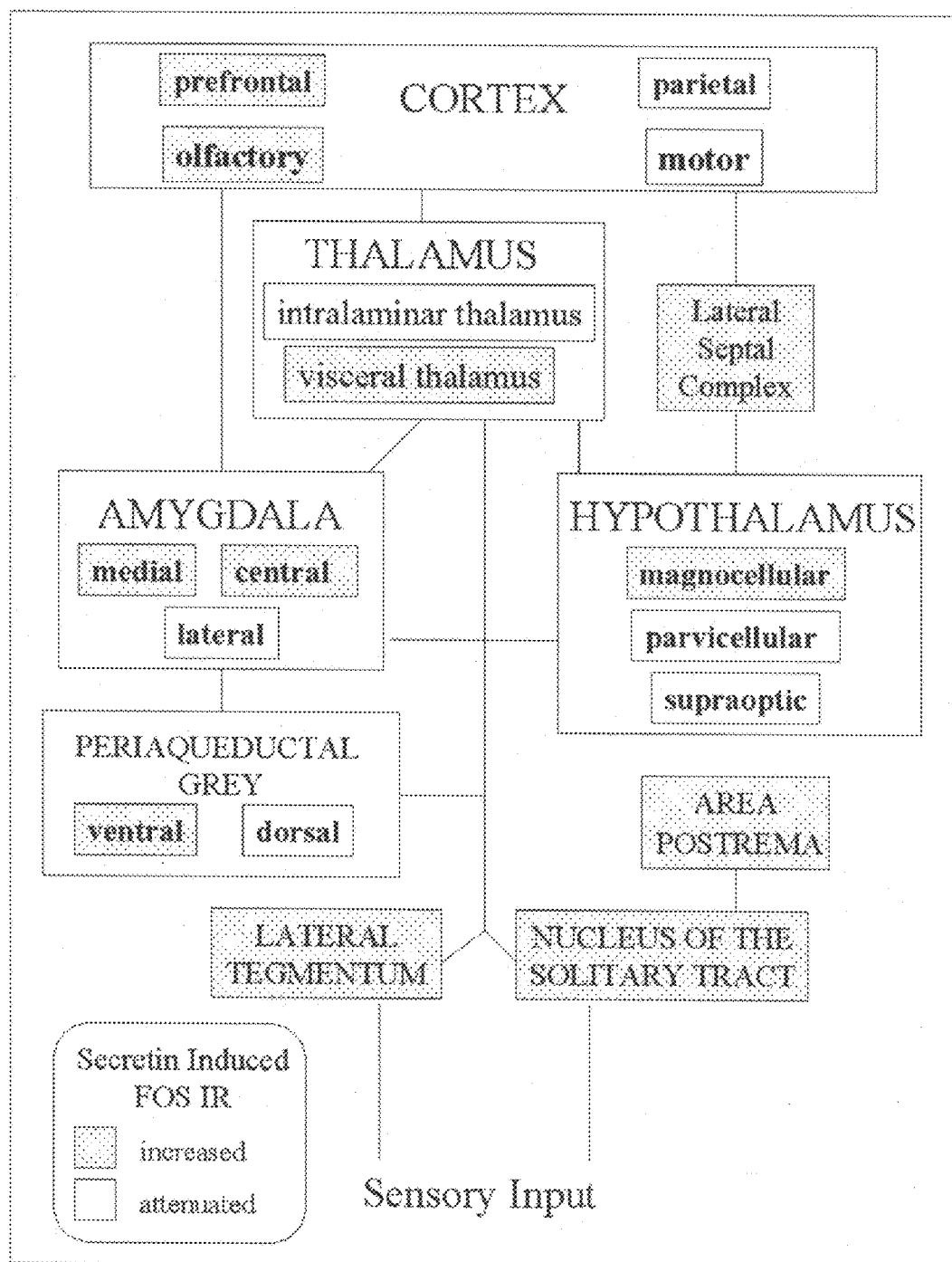
FIG. 1 illustrates brain regions with altered Fos expression in response to intracerebroventricular secretin. Secretin-induced Fos immunoreactivity in behavioral, endocrine, and autonomic areas of experimental animals. A few regions revealed attenuated Fos labeling as compared to controls.

Additional aspects of the present invention will be apparent in view of the description which follows.

DETAILED DESCRIPTION OF THE INVENTION

The inventors of the present invention have provided the first direct immunocytochemical demonstration of secretinergic immunoreactivity in the forebrain, indicating that the hypothalamus, like the gut, is capable of synthesizing the neuropeptide secretin. Secretin's dual expression by gut and brain secretin cells, as well as its overlapping central distribution with other stress-adaptation neurohormones, especially oxytocin, indicates that it is stress-sensitive. In addition, these findings indicate the existence of a neuroregulatory relationship between the peripheral and central stress response systems, as well as a dual role for secretin in conditioning both those stress adaptation systems. The inventors' discovery that colchicine up-regulates secretin further indicates that secretin may be synthesized on demand in response to stress, a mechanism that likely underlying secretin's role in autism.

The inventors have also shown that maternal intervention that includes reinstatement of specific components of maternal nurturing, including the establishment of synchronous attunement between mother and child, and/or treatments that replicate these effects pharmacologically, can effectively ameliorate severe behavioral symptomology.

In sum, the inventors have demonstrated that the brain and body form a single physiological circuit and that neuropeptides such as secretin and oxytocin form a communication mode that acts upon the brain and body simultaneously. The inventors have shown that neuropeptide release is a product of stress conditioning and determines regulated or dysregulated behavior, and further, that dysregulated behavior, including brain/gut disorders, autoimmune disorders, CNS disorders and pain may be ameliorated by neuropeptide therapy. The inventors have shown that stress-regulatory neuropeptides condition the brain/gut axis, accounting for their role in behavioral regulation, gastrointestinal function and dysfunction, and potential amelioration of autistic symptoms, which may be linked to visceral dysregulation.

Accordingly, the present invention encompasses compositions and methods for treating and preventing gastrointestinal disorders, central nervous system and behavioral disorders, autoimmune disorders and pain in a subject by administering to the subject a therapeutically effective amount of a vasoactive intestinal peptide (VIP), such as secretin, in combination with oxytocin.

The terms "gastrointestinal disorder," "gut disorder" and "brain/gut disorder" are used interchangeably herein and refer to any condition characterized by abnormal function, inflammation, pain, distress or discomfort involving the gastrointestinal system. When the nerves or muscles in any portion of the gastrointestinal system do not function in a coordinated fashion, the patient develops symptoms related to gastrointestinal motility. Typical symptoms of gastrointestinal disorders include heartburn, abdominal distension, nausea, vomiting diarrhea and constipation. Gastrointestinal disorders treatable by the present invention include, but are not necessarily limited to, irritable bowel disease, irritable bowel syndrome, dyspepsia, diarrhea, incontinence, pelvic floor pain, biliary disorders, abdominal bloating colitis, constipation and gastrodueodenal disorders.

Treating a disorder, as used herein, refers to treating any one or more of the functional conditions underlying the disorder. As used herein, preventing a disorder includes preventing the initiation of the disorder, delaying the initiation of the disorder, preventing the progression or advancement of the disorder, slowing the progression or advancement of the disorder, and delaying the progression or advancement of the disorder.

In one embodiment of the invention, the gastrointestinal disorder is treated in a subject in need of treatment by administering to the subject a therapeutically effective amount of secretin in combination with a therapeutically effective amount of oxytocin effective to treat the gastrointestinal disorder. In another embodiment, the secretin and oxytocin are administered in combination with protease inhibitors. The subject of the present invention is preferably a mammal (e.g., humans, domestic animals, and commercial animals, including cows, dogs, monkeys, mice, pigs, and rats), and is most preferably a human. The term "therapeutically effective amount," or "effective amount" as used herein mean the quantity of the composition according to the invention which is necessary to prevent, cure, ameliorate or at least minimize the clinical impairment, symptoms or complications associated with the disorder in either a single or multiple dose. The amounts of secretin and oxytocin effective to treat the disorder will vary depending on the disorder as well as the particular factors of each case, including the stage or severity of the gastrointestinal disorder, the subject's weight, the subject's condition, the subject's age and the method of administration. The skilled artisan can readily determine these amounts.

For purposes of the present invention, the term "central nervous system (CNS) disorder" refers to any condition characterized by dysregulated behavior, abnormal function, pain, distress or discomfort involving the central nervous system. Central nervous system disorders treatable by the present invention include, but are not necessarily limited to autism and autistic spectrum disorders, seizures, conduct disorder, oppositional defiant disorder (ODD), attentional/arousal dysregulation, attention-deficit/hyperactivity disorder (ADHD), obsessive-compulsive disorder, stereotypies, reactive attachment disorder, social isolation, attachment disorders, face recognition deficits, gaze aversions, and altered heart rate variability.

In one embodiment of the invention, the CNS is treated in a subject in need of treatment by administering to the subject a therapeutically effective amount of secretin in combination with a therapeutically effective amount of oxytocin effective to treat the CNS disorder. In another embodiment, the secretin and oxytocin are administered in combination with protease inhibitors.

For purposes of the present invention, the terms "autoimmune disorder" and "autoimmune disease" are used interchangeably and refer to any condition in which the production of antibodies or T cells directed against a self-antigen is a major cause of the pathology of the disease. Autoimmune disorders treatable by the present invention include, but are not necessarily limited to Hashimoto's thyroiditis, pernicious anemia, scleroderma, anti-phospholipid syndrome, autoimmune inner ear disease, Behcet's syndrome, chronic inflammatory polyneuritis, CREST syndrome, Churg Strauss Syndrome, Guillain-Barre syndrome, Goodpasture's syndrome, primary biliary cirrhosis, Crohn's disease, ulcerative colitis, Celiac disease, Wegner's granulomatosis, Sclerosing cholangitis, Addison's disease, type 1 diabetes, rheumatoid arthritis, systemic lupus erythematousus, dermatomyositis, Sjogren's syndrome, lupus erythematosus, multiple sclerosis, myasthenia gravis, Retiter's syndrome and Grave's disease.

In one embodiment of the invention, the autoimmune disorder is treated in a subject in need of treatment by administering to the subject a therapeutically effective amount of secretin in combination with a therapeutically effective amount of oxytocin effective to treat the GI disorder. In another embodiment, the secretin and oxytocin are administered in combination with protease inhibitors.

The term "pain" refers to any physical suffering usually associated with bodily disorder such as a disease, characterized by physical discomfort or distress.

In one embodiment of the invention, a subject experiencing pain is treated by administering to the subject a therapeutically effective amount of secretin in combination with a therapeutically effective amount of oxytocin effective to ameliorate the pain. In another embodiment, the secretin and oxytocin are administered in combination with one or more protease inhibitors.

The present invention establishes that vasoactive intestinal peptides (VIPs) such as secretin can be used in combination with oxytocin to prevent and treat patients suffering from gastrointestinal disorders. This new therapy will provide a unique strategy to treat brain/gut disorders, including gastrointestinal disorders, as well as other visceral and autoimmune disorders, central nervous system disorders, and pain.

As used herein, "secretin" refers to secretin and analogues and derivatives thereof, including, for example, natural or synthetic functional variants which have secretin biological activity, as well as fragments of secretin having secretin biological activity. As further used herein, the term "secretin biological activity" refers to activity that causes pancreatic secretion of bicarbonate and enzymes, and inhibits gastrin release from the stomach.

As used herein, "oxytocin" refers to oxytocin and analogues and derivatives thereof, including, for example, natural or synthetic functional variants which have oxytocin biological activity, as well as fragments of oxytocin having oxytocin biological activity. As further used herein, the term "oxytocin biological activity" refers to activity that causes contraction of myoepithelial cells, stimulation of uterine smooth muscle contraction at birth, or establishment of maternal behavior in mammals.

Methods of preparing secretin and its analogues and derivatives are well known in the art. Secretin, for example, is commercially available as SecreFlo® from RepliGen Corporation, 41 Seyon Street Building #1, Suite 100, Waltham, Mass. 02453. Likewise, oxytocin is commercially available from Fujisawa Healthcare, Inc., Three Parkway North, Deerfield, Ill. 60015-2548. Moreover, both secretin and oxytocin may be obtained in accordance with known biochemical procedures that are readily understood by those of skill in the art.

The protease inhibitors of the present invention include any substance capable of blocking or inhibiting the activity enzymes that degrade proteins by hydrolyzing peptide bonds between amino acid residues (proteases). Methods of preparing protease inhibitors are well known in the art. The protease inhibitor, Norvir® (ritonavir), for example, is commercially available from Abbott Laboratories, Abbott Park, Ill. Protease inhibitors which can be used in the present invention include, but are not necessarily limited to, Invirase® (saquinavir), Fortovase® (saquinavir), Norvir® (ritonavir), Crixivan® (indinavir), Viracept® (nelfinavir), Agenerase® (amprenavir), Keletra® (lopinavir+ritonavir), Reyataz® (atazanavir) and Lexiva® (fosamprenavir). The protease inhibitors are administered in amounts that are effective to treat or prevent a GI, CNS or autoimmune disorder or pain in the subject. These amounts may be readily determined by the skilled artisan.

The inventors have discovered localizations of secretin that overlap with those of other stress-regulatory neurohormones, especially oxytocin. Given secretin's expression by gut and brain cells, this finding indicates that secretin has an integrated peripheral and central stress-related function in maintaining homeostasis. These results suggest that secretin/glucagons/VIP peptide family members and other peptides such as oxytocin act together as part of a mind/brain/body stress communication and regulatory network. Accordingly, dysregulated behavior, including brain/gut disorders, may be ameliorated by multi-neuropeptide therapy.

In a method of the present invention, secretin is administered to a subject in need of treatment in combination with oxytocin, such that a synergistic therapeutic effect is produced. A "synergistic therapeutic effect" refers to a greater-than-additive therapeutic effect which is produced by a combination of two therapeutic agents, and which exceeds that which would otherwise result from individual administration of either therapeutic agent alone. For instance, administration of secretin in combination with oxytocin unexpectedly results in a synergistic therapeutic effect by providing greater efficacy than would result from use of either of the therapeutic agents alone.

In the method of the present invention, administration of secretin "in combination with" oxytocin refers to co-administration of the two therapeutic agents. Co-administration may occur concurrently, sequentially, or alternately. Concurrent co-administration refers to administration of both secretin and oxytocin at essentially the same time. For concurrent co-administration, the courses of treatment with the secretin and with the oxytocin may be run simultaneously. For example, a single, combined formulation, containing both an amount of secretin and an amount of oxytocin in physical association with one another, may be administered to the subject. The single, combined formulation may consist of an oral formulation, containing amounts of both secretin and oxytocin which may be orally administered to the subject, or a liquid mixture, containing amounts of both secretin and oxytocin, which may be injected into the subject.

It is also within the confines of the present invention that an amount of the secretin and an amount of the oxytocin may be administered concurrently to a subject, in separate, individual formulations. Accordingly, the method of the present invention is not limited to concurrent co-administration of the secretin and the oxytocin in physical association with one another.

In the method of the present invention, the secretin and the oxytocin also may be co-administered to a subject in separate, individual formulations that are spaced out over a period of time, so as to obtain the maximum efficacy of the combination. Administration of each therapeutic agent may range in duration from a brief, rapid administration to a continuous perfusion. When spaced out over a period of time, co-administration of the secretin and the oxytocin may be sequential or alternate. For sequential co-administration, one of the therapeutic agents is separately administered, followed by the other. For example, a full course of treatment with the secretin may be completed, and then may be followed by a full course of treatment with the oxytocin. Alternatively, for sequential co-administration, a full course of treatment with the oxytocin may be completed, then followed by a full course of treatment with the secretin. For alternate co-administration, partial courses of treatment with the secretin may be alternated with partial courses of treatment with the oxytocin, until a full treatment of each therapeutic agent has been administered.

The therapeutic agents of the present invention (i.e., the secretin and the oxytocin, either in separate, individual formulations, or in a single, combined formulation) may be administered to a human or animal subject by known procedures, including, but not limited to, oral administration, inhalation, sublingual administration, parenteral administration (e.g., intramuscular, intraperitoneal, intravascular, intravenous, intracerebroventricular, or subcutaneous administration), and transdermal administration. Preferably, the therapeutic agents of the present invention are administered orally, intravenously or intracerebroventricularly.

For oral administration, the formulations of the secretin either alone or in combination with the oxytocin may be presented as capsules, tablets, powders, granules, or as a suspension. The formulations may have conventional additives, such as lactose, mannitol, corn starch, or potato starch. The formulations also may be presented with binders, such as crystalline cellulose, cellulose derivatives, acacia, corn starch, or gelatins. Additionally, the formulations may be presented with disintegrators, such as corn starch, potato starch, or sodium carboxymethyl cellulose. The formulations also may be presented with dibasic calcium phosphate anhydrous or sodium starch glycolate. Finally, the formulations may be presented with lubricants, such as talc or magnesium stearate.

For parenteral administration, the formulations of the secretin either alone or in combination with the oxytocin may be combined with a sterile aqueous solution which is preferably isotonic with the blood of the subject. Such formulations may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. Moreover, the formulations may be delivered by any mode of injection, including, without limitation, epifascial, intracapsular, intracutaneous, intramuscular, intraorbital, intraperitoneal (particularly in the case of localized regional therapies), intraspinal, intrasternal, intravascular, intravenous, intracerebroventricular, parenchymatous, or subcutaneous.

For transdermal administration, the formulations of the secretin and the oxytocin (whether individual or combined) may be combined with skin penetration enhancers compatible with other ingredients of the pharmaceutical composition, such as propylene glycol, polyethylene glycol, isopropanol, ethanol, oleic acid, N-methylpyrrolidone, and the like, which increase the permeability of the skin to the therapeutic agent, and permit the therapeutic agent to penetrate through the skin and into the bloodstream. The therapeutic agent/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent such as methylene chloride, evaporated to the desired viscosity, and then applied to backing material to provide a patch.

The dose of the secretin and the oxytocin of the present invention may also be released or delivered from an osmotic mini-pump. The release rate from an elementary osmotic mini-pump may be modulated with a microporous, fast-response gel disposed in the release orifice. An osmotic mini-pump would be useful for controlling release, or targeting delivery, of the therapeutic agents.

It is within the confines of the present invention that the formulations of the secretin either alone or in combination with the oxytocin may be further associated with a pharmaceutically-acceptable carrier, thereby comprising a pharmaceutical composition. The pharmaceutically-acceptable carrier must be "acceptable" in the sense of being compatible with the other ingredients of the composition, and not deleterious to the recipient thereof. Examples of acceptable pharmaceutical carriers include, but are not limited to, carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may conveniently be presented in unit dosage.

The formulations of the present invention may be prepared by methods well-known in the pharmaceutical art. For example, the active compound may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the therapeutic agents of the present invention (i.e., the secretin and the oxytocin, and their analogues and derivatives, either in separate, individual formulations, or in a single, combined formulation) to a subject to treat a GI, CNS or autoimmune disorder. The therapeutic agents are provided in amounts that are effective to treat or prevent a GI, CNS or autoimmune disorder in the subject. These amounts may be readily determined by the skilled artisan.

In the synergistic combination of the present invention, the secretin and the oxytocin may be combined in a single formulation, such that the amount of the secretin is in physical association with the amount of the oxytocin. This single, combined formulation may consist of an oral formulation, containing amounts of both the secretin and the oxytocin, which may be orally administered to the subject, or a liquid mixture, containing amounts of both the secretin and the oxytocin, which may be injected into the subject.

Alternatively, in the synergistic combination of the present invention, a separate, individual formulation of the secretin may be combined with a separate, individual formulation of the oxytocin. For example, an amount of the secretin may be packaged in a vial or unit dose, and an amount of the oxytocin may be packaged in a separate vial or unit dose. A synergistic combination of the secretin and the oxytocin then may be produced by mixing the contents of the separate vials or unit doses in vitro. Additionally, a synergistic combination of the secretin and the oxytocin may be produced in vivo by co-administering to a subject the contents of the separate vials or unit doses, according to the methods described above. Accordingly, the synergistic combination of the present invention is not limited to a combination in which amounts of the secretin and the oxytocin are in physical association with one another in a single formulation.

In a preferred embodiment, the dosage of secretin is about 1 mg day to 100 mg/day. In one embodiment, secretin can be administered in a dosage of about 0.001 mg/day to about 1000 mg/day. Oxytocin also can be administered in a dosage of about 0.001 mg/day to about 1000 mg/day, and preferably, is administered in a dosage of about 1 mg day to 100 mg/day.

The appropriate effective therapeutic amounts of the secretin and the oxytocin within the listed ranges can be readily determined by the skilled artisan.

EXAMPLES

The following examples illustrate the present invention, and are set forth to aid in the understanding of the invention, and should not be construed to limit in any way the scope of the invention as defined in the claims which follow thereafter.

Example 1

In the following study, the inventors investigated whether central networks are involved in the presumptive behavioral and autonomic regulatory actions of secretin. The inventors discovered that secretin alters the activity of structures involved in behavioral conditioning of stress adaption and visceral reflex reactions.

Animals and Surgical Procedures

The inventors obtained data in eight adult male Sprague-Dawley rats weighing 250-450 g. The rats were obtained from Hilltop Lab Animals, Inc. (Scottdale, Pa.). Under ketamine-xylazine anesthesia, using sterile techniques, a stainless steel guide cannula was stereotaxically inserted into the lateral ventricle of each rat. Each cannula was affixed in place with dental cement secured to the skull. To prevent clogging, a removable 27 gauge wire was inserted into the guide cannula. The placement of the cannula with reference to bregma was 1.4-mm lateral, 0.5-mm caudal, and a depth of 2.5 mm from the surface of the skull. The rats were allowed to recover for 4-5 days before the injections. During this time, both experimental and control rats were administered 0.01 ml/kg buprinorphine hydrochloride every 6 h to reduce pain. Injections were made in the lateral ventricle 5 mm from the surface of the skull, via a premeasured cannula attached by polyethylene tubing (PE20) to a 25 ILL Hamilton syringe containing either phosphate buffered saline (PBS) at pH 7.4 (n=4) or 10 ILg (n=1, pilot study) or 30 ILg (n=3) of secretin (Sigma, St. Louis, Mo.) dissolved in 5-10 ILL PBS. Secretin injections were performed between 11:00 A.M. and 1:00 P.M.

The Immunocytochemical Detection of Fos

Three hours after the i.c.v. injection, rats were administered sodium pentobarbital and perfused transcardially with heparinized, physiological saline followed by a 4% solution of paraformaldehyde in sodium phosphate buffer, pH 7.4. Whole brains were removed and blocked. Identical procedures were followed in control (n=4) and experimental animals (n=4). Tissue blocks were postfixed for 2-3 h in individual glass vials containing 4% paraformaldehyde in 0.1 M phosphate buffer (PBS, pH 7.4) and cryoprotected overnight at 4° C. in a solution of 10% sucrose in 0.1 M PBS. Frozen sections were cut on a sliding microtome at 30 JLm in the transverse plane and every fourth section was processed immunocytochemically for c-fos protein. Tissues from control and experimental animals were processed simultaneously in the same solutions in order to control for potential variability in immunocytochemistry. All incubations were carried out in separate test wells on a Thomas rotator table. Tissues were collected in 0.1 M PBS (pH 7.4) in spot test wells and washed in Tris-buffered saline (TBS) between each step. Nonspecific binding sites were blocked by preincubating for 30 min in bovine serum albumin (BSA), diluted 1:30 in TBS. Thereafter, sections were incubated overnight in primary whole rabbit antiserum raised against Fos protein diluted 1:10,000 (Oncogene, Cambridge, Mass.). The antisera were diluted in TBS containing 0.1% BSA, to which 0.25% Triton X-100 was added to facilitate antibody penetration. Tissues were incubated for 1 h in biotinylated goat anti-rabbit IgG secondary antibody (1:200) and washed again, three times for 5 min each. Tissues were incubated for 45 min in avidin-biotin peroxidase complex (1:100) (Vector Labs, ABC Elite Kit). The bound peroxidase immunoreaction product was visualized by treating tissues with a substrate solution of the chromagen, diaminobenzidine (DAB), and hydrogen peroxide in TBS. Control sections were processed omitting incubation in primary antibody. Sections were washed, mounted, dehydrated, and coverslipped without counterstaining. Alternate sections were counterstained in thionin to reveal nuclear boundaries. Sections were examined by light microscopy and digital images obtained with a SPOT-RT slider Diagnostic Instruments camera mounted on a Nikon Microphot microscope.

Results

Fos immunoreactivity (IR) was confined to nuclei that varied in staining intensity. Comparisons were drawn between the numbers of labeled nuclei observed in experimental and control cases. Qualitative analyses revealed clear-cut topographic differences in immunolabeling patterns, as illustrated in the Figures. The striking distinctions between experimental and control animals were replicated for all pairs.

Figure 2:
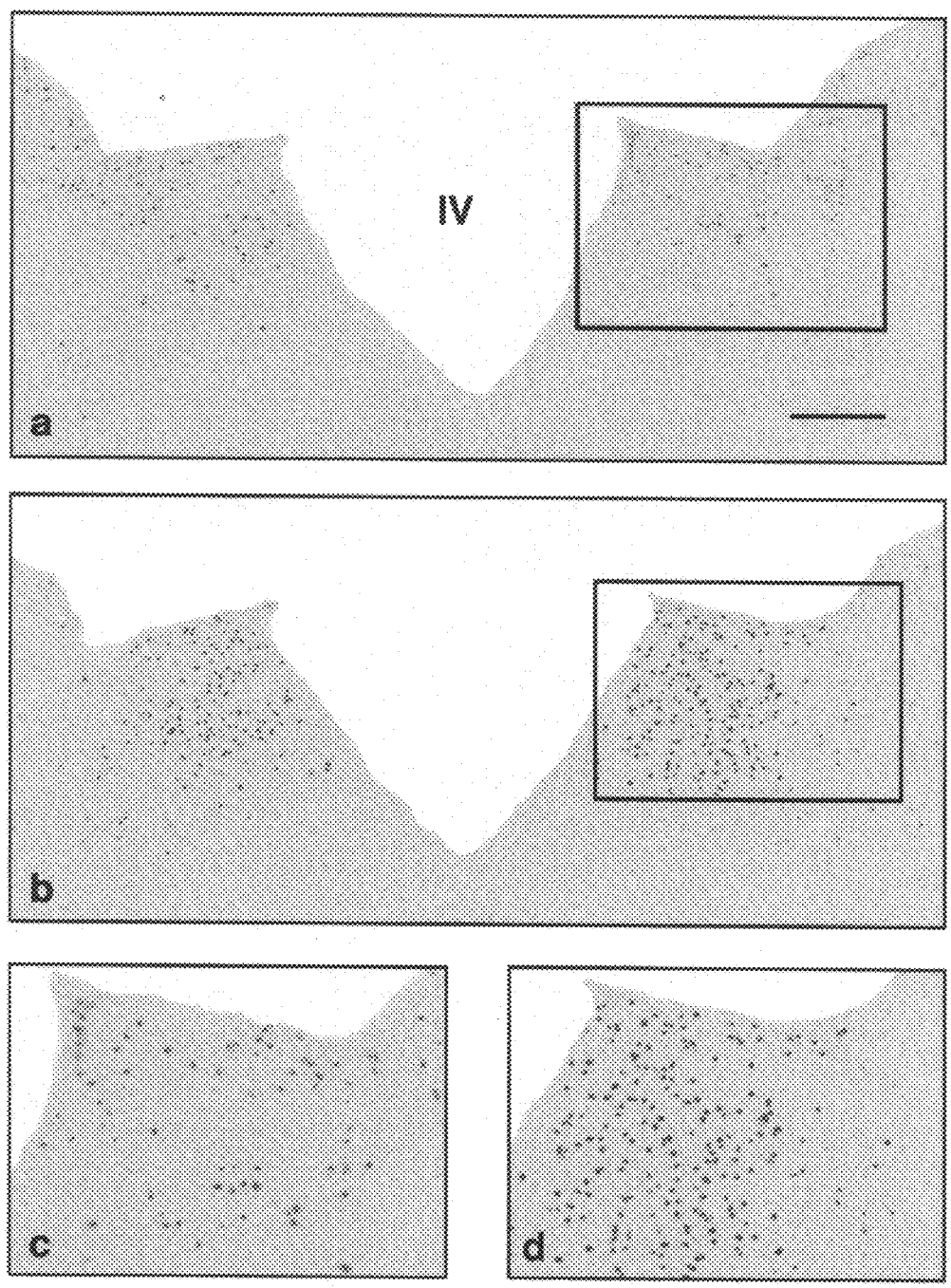
FIG. 2 shows secretin-induced c-fos expression in the nucleus of the solitary tract (NTS). Photomicrographs of Fos immunostained sections through the NTS in animals perfused 3 hours after treatment with PBS (a) versus secretin 10 μg q 15 min×3 (b). Enlargement of the right NTS in control (c) and experimental (d) animals. The activation patterns were limited to specific subnuclei of the general visceral afferent division. Secretin activated the NTS and its projection fields in the reticular formation, diffuse projection systems and the mesolimbic network, which is involved in motivated stress adaptation responses. The area postrema was also activated by secretin (not illustrated). This central visceral response pattern may be responsible for the regulatory effect of secretin in autistic children. Scale bar (a) and (b)=234 μm; Scale bar (c) and (d)=75 μm.
Figure 3:
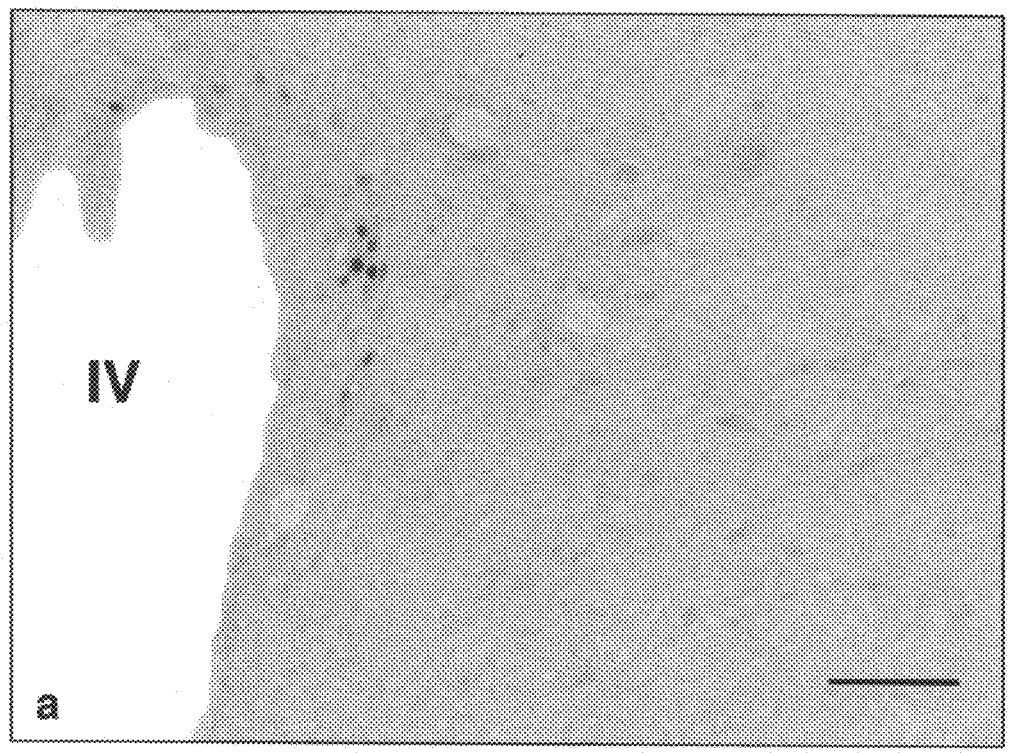
FIG. 3 depicts secretin induced c-fos expression in the locus ceruleus (LC). Photomicrographs of Fos immunostained sections through the LC in animals perfused 3 hours after treatment with PBS (a) versus secretin 10/μq 15 min×3 (b). The fourth ventricle (IV) served as a landmark. The LC is a key component of the central attentional network involved in triggering stress-adaptation responses. Its cortical and subcortical projection fields were also responsive to secretin. Secretin and vasoactive intestinal peptide activate tyrosine hydroxylase in sympathetic ganglia and visceral end-organs (Schwarzschild, et al., 1989), and as the data suggest, possibly, in the LC. The control LC demonstrates scant labeling. The LC is the major source of central norepinephrine transmission involved in coordinated behavioral arousal and sympathetic stress adaptation responses. Scale bar=75 μm.
Figure 3:
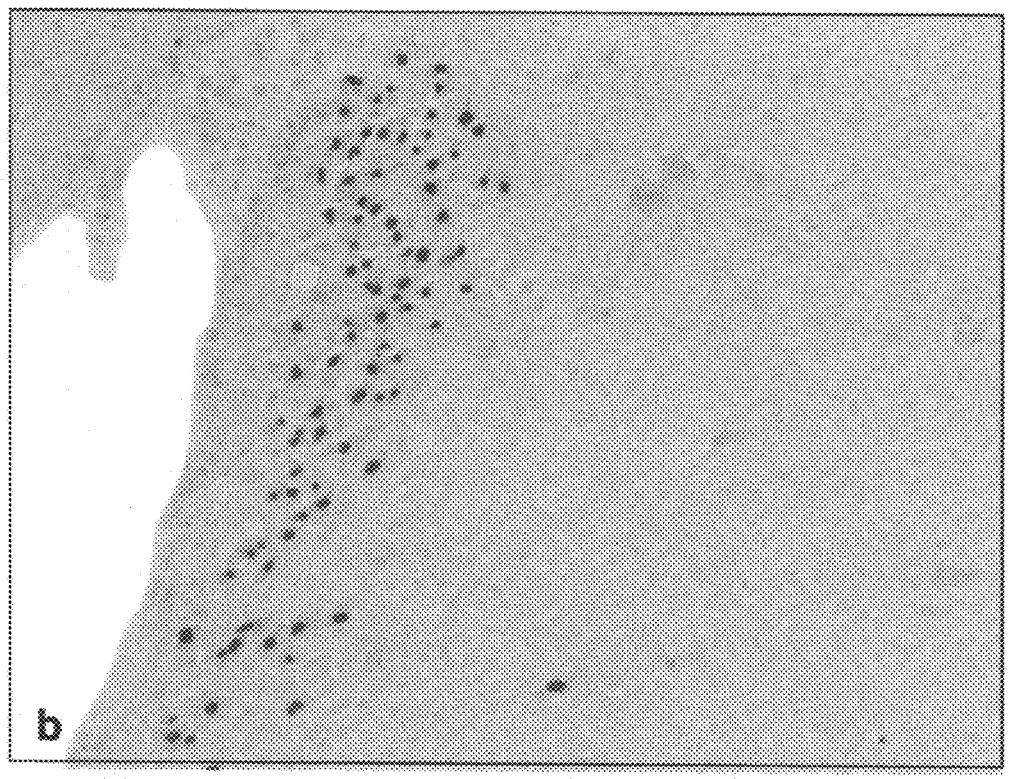
Figure 4:
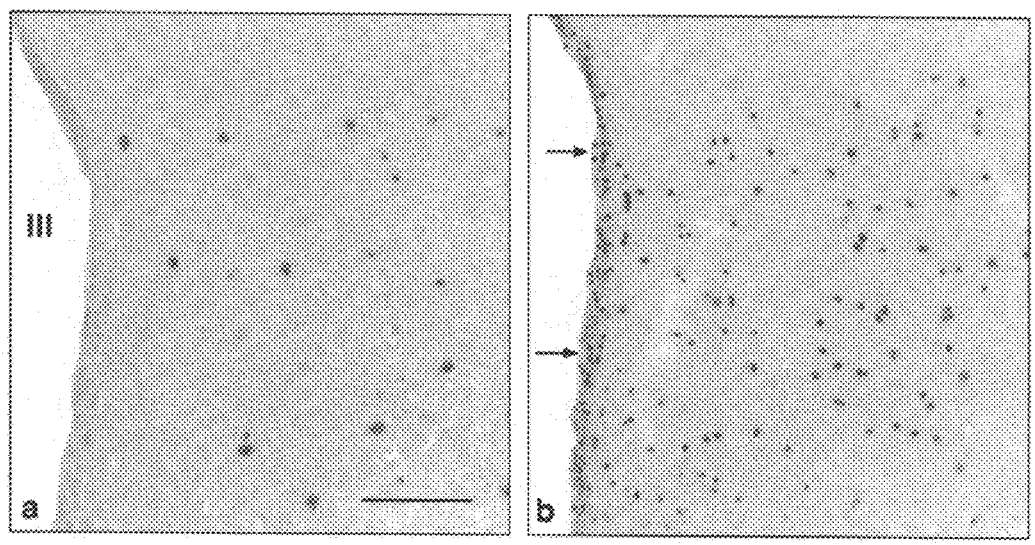
FIG. 4 shows secretin induced c-fos expression of ependymal (arrows) and subependymal cells lining the third ventricle (III). Photomicrographs of Fos immunostained sections through the tuberal region of the hypothalamus in animals perfused 3 hours after treatment with PBS (a) versus secretin 5 μg q15 min×3 (b). The third ventricle served as a landmark. The ependymal transport mechanism related to central actions of secretin is discussed in the text. Scale bar=75 μm.

Secretin-infused rats showed altered numbers of Fos immunoreactive nuclei, mainly in visceral and limbic areas of the brain (FIG. 1) in the pilot experiment and, more robustly, in the subsequent pairs administered higher doses of secretin. Secretin induced c-fos protein expression in the dorsal vagal complex, including the general afferent division of NTS and the dorsal motor nucleus (FIG. 2). Fos IR was concentrated throughout the area postrema and its subpostremal region of transition with the NTS and the commissural, medial parvicellular and periventricular subnuclei. Secretin activated c-fos expression in cells in the intermediate reticular region of the lateral tegmental field. Secretin induced c-fos expression in the locus ceruleus (FIG. 3), ventral periaqueductal gray, and the paraventricular thalamic nucleus, corresponding to the nondiscriminative, stress-reactive, visceral thalamus (Ruggiero, et al., 1998). In the hypothalamus, the predominant labeling mapped to the paraventricular hypothalamic nucleus, mainly its periventricular region and magnocellular subdivision. Secretin induced c-fos in the medial and central amygdala and the lateral septal complex. Tissues from secretin-pretreated animals in the study exhibited c-fos induction in ependymal and subependymal nuclei lining the third ventricle (FIG. 4). These cells were devoid of Fos immunoreactivity in controls.

Figure 5:
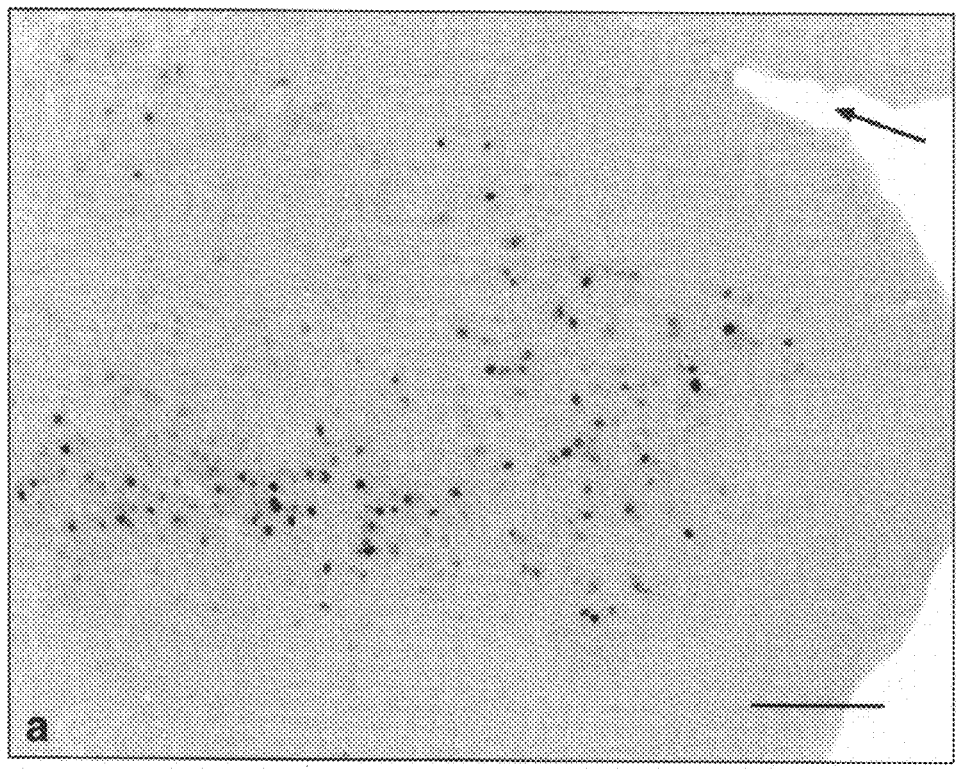
FIG. 5 shows secretin induced c-fos expression of the piriform cortex. Photomicrographs of Fos immunostained sections through the frontal pole in animals perfused 3 hours after treatment with PBS (a) versus secretin 10 μg q 15 min×3 (b). The rhinal fissure (arrow) serves as a landmark. Secretin administered into the lateral ventricle of freely moving rats altered their exploratory behavior (Charlton, et al., 1981), possibly by its modulation of olfactory and place memory. The labeling of piriform or primary olfactory cortex may relate to the possible action of secretin in influencing social recognition as suggested by the increase in eye contact and language after intravenous administration in autistic children (Horvath, et al., 1998). Scale bar=75 μm.
Figure 5:
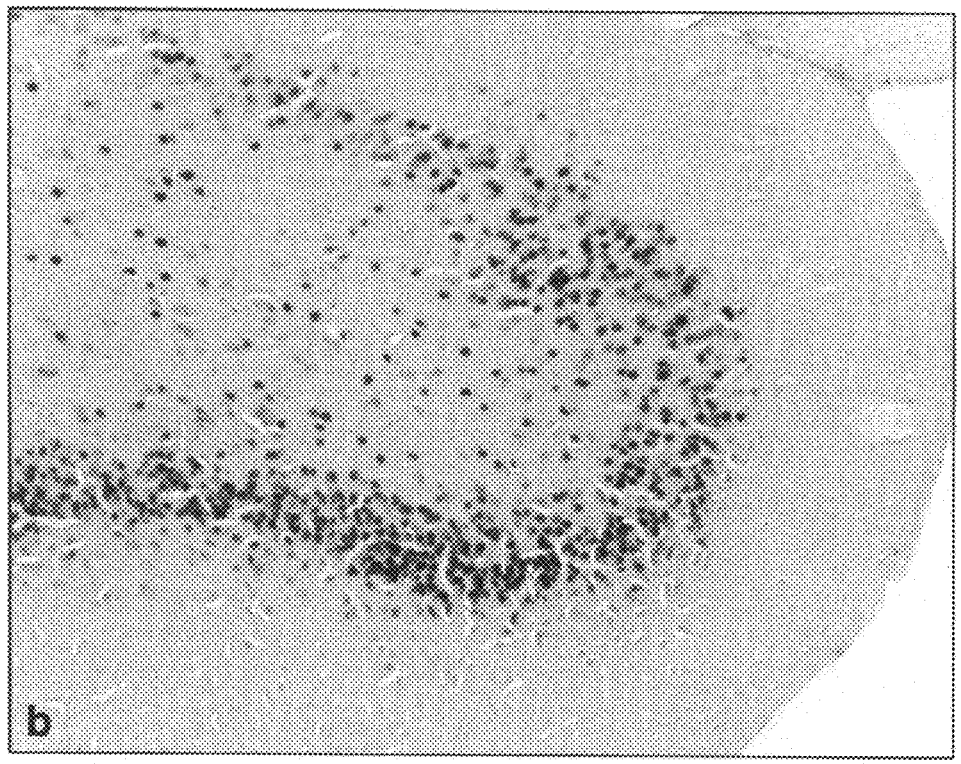
Figure 6:
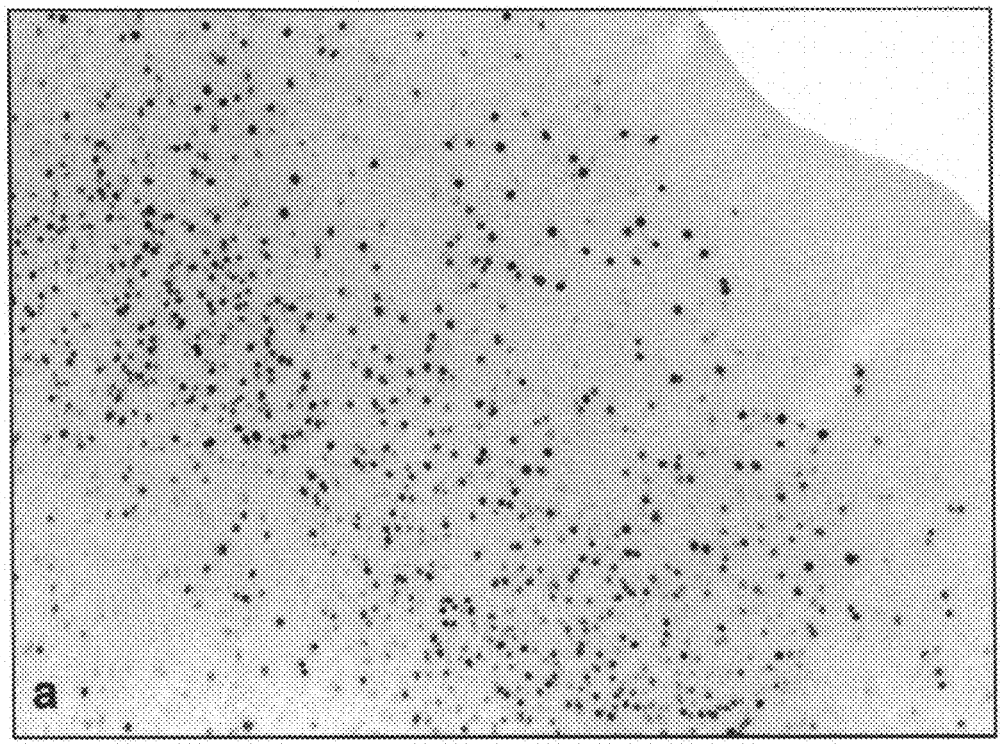
FIG. 6 shows secretin attenuated c-fos expression of the parietal cortex. Photomicrographs of Fos immunostained sections through the parietal cortex in animals perfused 3 hours after treatment with PBS (a) versus secretin 10 μg q 15 min×3 (b). Sensory and association areas of the parietal cortex are influenced by and implicated in the behavioral effects of i.c.v. secretin (Charlton, et al., 1981). Scale bar=75 μm.
Figure 6:
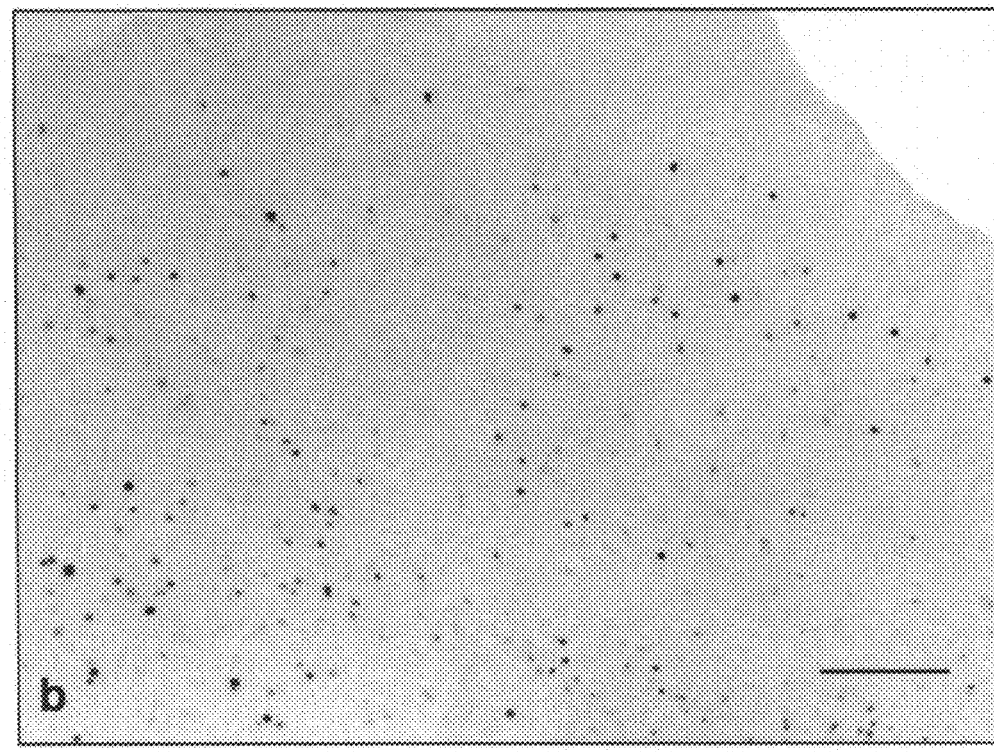

Specific areas of the cerebral hemispheres were heavily labeled in the secretin-treated rats as compared to controls. The nuclear immunoreaction product was most heavily concentrated along the medial bank of the prefrontal cortex, the orbitofrontal cortex, the anterior olfactory nucleus, and the piriform cortex (FIG. 5). Secretin attenuated Fos immunoreactivity in the dorsal periaqueductal gray, the intralamanar thalamus, the medial parvicellular hypothalamus, which synthesizes corticotrophin releasing hormone, the motor cortex, and the somatosensory and association areas of the parietal cortex (FIG. 6).

This study is the first systematic analysis of the central actions of secretin in the brain of the laboratory rat, using c-fos activation as a monitor of altered regional metabolism. The data support a functional neuroanatomical basis for a neuroregulatory role of secretin, corroborating prior evidence of inhibition of exploratory activity in rats by i.c.v. injections (Charlton, et al., 1981) and interactions with other neurotransmitter systems such as dopamine (Fuxe, et al., 1979). Moreover, secretin has an established capability to stimulate, in vitro, the accumulation of cyclic AMP (cAMP) in mouse brain cells (van Calker, et al., 1980).

Data in the present study predict that secretin of central and/or peripheral origin may activate behavioral and visceral reflex regulatory circuits (FIG. 1). The principal regions activated by i.c.v. secretin injection are areas of visceral representation, including the periventricular stress adaptation network. Especially striking activity patters were localized to areas of gastrointestinal and chemoreceptor representation in the medulla oblongata. Included were the nucleus of the solitary tract and its relay stations in the lateral tegmentum and the dorsal motor nucleus. These activated structures form a visceral sensorimotor reflex circuit that is involved in cardiorespiratory and parasympathetic reflex regulation of the subdiaphragmatic viscera (Li, et al., 1992; Lin, et al., 1998; Sica, et al., 2000a,b; Sved, et al., 1995), including vagal release of secretin-releasing peptide and secretin and involving adrenergic influences on the neurosecretory activity of intestinal secretin-producing S cells (Li, et al., 1995).

Functional (Charlton, et al., 1981) and structural data (Chang, et al., 1985) indicate that secretin influences behavior via its actions on visceral reflex regulatory circuits, including higher order areas of visceral representation such as areas of the prefrontal cortex, abnormal in autism (Haznedar, et al., 2000). These areas were activated in the study and are thought to be involved in perceptual encoding mechanisms and in modulating behavioral reactivity (Corbett, et al., 1983; van Honk, et al., 2002). The NTS (FIG. 2), which receives visceral metabolic input from the vagus (Ruggiero, et al., 1996; Ruggiero, et al., 1996; Sved, et al., 1995), was found to exhibit the highest binding to [$I^{125}$] secretin of any brain tissue (Nozaki, et al., 2002). The NTS projects, in humans, to regions of the lateral tegmental field involved in sensory processing and autonomic control (Ruggiero, et al., 2000). This visceral circuit forwards integrated signals from the internal and external milieu to the raphe, locus ceruleus, and the visceral thalamus (Ruggiero, et al., 1998) that serve as regulators of cerebral blood flow and as diffuse regulators of electrocortical and autonomic activity patterns (Aston-Jones, et al., 2000; Golanov, et al., 2000; Underwood, et al., 1999). The visceral or paraventricular thalamic nucleus, which was powerfully activated by secretin, may contribute to the behavioral regulatory actions of the hormone (Charlton, et al., 1981). This periventricular region of the thalamus projects to and is modulated by the prefrontal cortex and its meso striatal network (Groenewegen, et al., 1994, Otake, et al., 1994), which is thought to motivate goal-directed behaviors such as stress responses to homeostatic challenges (Brown, et al., 1992, Sica, et al., 2000a,b).

Secretin activated NTS projection fields in the hypothalamus, including paraventricular regions involved in coordinating behavioral, endocrine, and autonomic functions (Cole, et al., 2002). Bioactive neuroregulatory peptides are known to exert controls over the dorsal vagal complex (Ruggiero, et al., 1993), the paraventricular hypothalamus (Moga, et al., 1994), and over pituitary neurosecretory activity (Arima, et al., 2000). Secretin increases dopamine turnover in the median eminence and reduces dopamine turnover in the forebrain, a pattern of changes attributed to central actions of secretin (Fuxe, et al., 1979). The data from this study confirm and extend this hypothesis.

Such peptides may be secreted into the cerebral ventricles to act distally, influencing receptive regions via ependymal tanycytic transport mechanisms (Amat, et al., 1999; Bruni, 1998). Circulating peptides, such as peripherally infused pancreatic polypeptide, bind to specific receptors in the dorsal vagal complex and, via the area postrema, regulate components of the pancreatic control system (Deng, et al., 2001). The results reported in the present study suggest that secretin may act similarly. Among the sites expressing Fos were periventricular regions of the hypothalamus adjacent to the third ventricle lined by filament-bearing ependymal tanycytes involved in CSF/brain transport mechanisms (Flament-Durand, et al., 1985; Rodriguez, et al., 1979). Secretin induced c-fos activation in ependymal and subependymal cells in these regions bordering the third ventricle (see FIG. 4).

Secretin May Influence the Stress Arousal Response Patterns and Attention

Secretin activated the locus ceruleus (LC) (FIG. 3), which is a key periventricular component of the central attentional network involved in triggering stress-arousal responses and vigilance states (Aston-Jones, et al., 2000). In the human brain, the LC, raphe, and subependymal region are modulated by the neuropeptide corticotrophin-releasing hormone (CRH) (Ruggiero, et al., 1999), implicated in suppressing immune responses (Rassnick, et al., 1994). CRH is hypersecreted into the CSF under psychopathological conditions related to childhood trauma and to the neurobiology of mood and anxiety disorders (Heim, et al., 2001). The cortical projection fields of the LC were also responsive to secretin (FIGS. 5 and 6). Secretin and vasoactive intestinal peptide (VIP) induce tyrosine hydroxylase in sympathetic noradrenergic ganglia and visceral end-organs (Schwarzschild, et al., 1989) and, as the data suggest, possibly in the LC. The LC is the major source of central norepinephrine transmission involved in coordinated behavioral arousal and sympathetic stress adaptation responses (Aston-Jones, et al., 2000, Peyronnet, et al., 2002). Secretin and its family of peptides may regulate peripheral and central neurotransmitter metabolism (Schwarzchild, et al., 1989). An open question is whether the LC is dysregulated in autism. According to Segawa (1989), hypofunction of the LC results in the failure of extinction of acquired memory in mice, which they relate clinically to the unusual memory and resistance to change in autistic children.

Rat Brain Regions Activated by Secretin are Homologous to Those Dysregulated in Autistic Children Several studies using neuroimaging and neuropathological data have elucidated functional and anatomical abnormalities in autism (Blatt, et al., 2001; Haznedar, et al., 2000; Howard, et al., 2000; Raymond, et al., 1996). The frontal cortex is responsive to secretin and, via its subcortical connections, subserves adaptive responses to the environment, including initiation versus withholding, a common symptom in autism (Bradshaw, et al., 2000). c-fos activation was observed in the prefrontal cortex and subcortical outlets for emotional expression (Morgan, et al., 1993; Morgan, et al., 1999), areas demonstrating altered cerebrovascular perfusion in autistic subjects according to recent neuroimaging studies (Haznedar, et al., 2000, Ohnishi, et al., 2000). Secretin also activated the anterior olfactory nucleus, the piriform cortex, and the amygdala, the last of which is an established site of pathology in autism (Howard, et al., 2000, Sparks, et al., 2002, Sweeten, et al., 2002), and all three of which are important in social recognition and early environmental conditioning of neonatal behaviors (Ferguson, et al., 2001, Haxby, et al., 2002).

Secretin altered the metabolic activity of the parietal cortex, which is a recently verified site of pathology in autism based on reductions in nicotinic and muscarinic receptor binding, raising the question of whether this is an adaptation response to excess cholinergic stimulation. Cortical M(1) receptor binding was as much as "30% lower than normal in the autistic subjects, and the difference reached significance in the parietal cortex. In both the parietal and frontal cortices, differences in nicotinic receptors assessed by [(3)H]epibatidine binding were significant and extensive" (Perry, et al., 2001). Nicotinic receptor abnormalities were also found in the cerebellar cortex of autistics (Lee, et al., 2002). Since secretin attenuated c-fos expression in the parietal cortex, this area might be a site of action of secretin in treating the symptomatology of abnormal motor activity in autistic children.

Secretin's effects on the cerebellum have been examined by Yung, et al., who localized secretin mRNA in Purkinje cells. Their study demonstrated release of secretin from the somato-dendritic region and demonstrated facilitation of GABA transmission with secretin serving as a retrograde messenger in the cerebellum (Yung, et al., 2001). Of interest would be an examination of the effects of secretin on spatial working memory and cerebellar-neocortical networks that are abnormal in autism (Luna, et al., 2002). Abnormal serotonin metabolism and asymmetries of serotonin synthesis in the frontal cortex, thalamus, and cerebellum (Chugani, et al., 1997) may be involved. Few studies have examined the lower brainstem in autistics, although a scant database implicates developmental defects involving the medulla oblongata (Bauman, et al., 1985; Gaffney, et al., 1988; Hashimoto, et al., 1992, 1993) that may have their etiology in intrauterine or perinatal hypoxia; autism in case studies may be consequent to intrauterine exposure to vasoconstrictor agents such as cocaine that is often coabused with nicotine, another vasoconstrictor (Davis, et al., 1992). Secretin may interact centrally at visceral reflex centers, especially the norepinephrine regions of NTS, lateral reticular formation and LC, that protect against hypoxia (Peyronnet, et al., 2002) by regulating systemic and cerebral blood flow and behavioral flexibility and attention (Aston-Jones, et al., 2000).

Vagal Afferents Activated by Secretin

Secretin's effects on the brain are mediated by its peripheral as well as its central actions. Secretin's peripheral actions, such as gastric emptying and deacidification of the gut (Jin, et al., 1994), stimulation of hepatic bile flow (McGill, et al., 1994), increase of coronary blood flow (Gunnes, et al., 1983, 1985), and increased lipolysis during fasting and muscular exercise (Bell, et al., 1984), are communicated to the dorsal vagal complex via the vagus and spinal nerves (Ruggiero, et al., 1993, 1996b; Westlund, et al., 1996).

The NTS, or sensory component of the dorsal vagal complex, modulates physiological states via its projections to behavioral, autonomic, and endocrine areas, many of which are modulated by secretin. Vagal stimulators, which would activate cells in the dorsal vagal complex involved in the neuronal regulation of the release of secretin-releasing peptide and secretin (Li, et al., 1995), have been used in treating epilepsy (Patwardhan, et al., 2000). Neonatal seizures are linked to pre- and perinatal maternal risk factors (Arpino, et al., 2001). Seizures are a comorbidity in 11-30% of autistic children (Giovanardi, et al., 2000; Tuchman, et al., 1997), which might relate to prenatal hypoxic challenges that alter postnatal excitability of cortical neurons (Maresova, et al., 2001). This study's activation patterns of the frontal and parietal cortex, the LC, and visceral afferents raise the question as to whether secretin is modulating neuronal excitability of stress arousal systems. Secretin is known to act peripherally (McGill, et al., 1994; Pollack, et al., 1990; Schwarzschild, et al., 1989), altering vagal afferent input and controlling its release via beta-adrenergic receptors (Li, et al., 1995). Pediatric seizure disorders are associated with elevated CSF and serum levels of several bioactive neuropeptides, including VIP, a member of the secretin/glucagon receptor family (Ko, et al., 1991). The NTS and its terminal fields, including the periventricular thalamic stress axis (Otake, et al., 1995), were among the regions of greatest activation in this study. This activation pattern may relate to the anticonvulsive effects of vagal nerve stimulators on medial thalamic activity in patients with epilepsy (Ring, et al., 2000). These areas, as well as the seizure-prone olfactory areas (Ekstrand, et al., 2001) activated in this study, are exquisitely sensitive to chronic intermittent hypoxia (Sica, et al., 2000a,b) and, perhaps, influenced by the peripheral and central actions of secretin in protecting the postnatal homeostatic mechanisms against the long-term effects of intrauterine hypoxia (Peyronnet, et al., 2002).

Secretin-Activated Regions Involved in Central Autonomic Control are Essential in Protecting Visceral Homeostasis Secretin may influence behavior by peripheral and central mechanisms of actions that protect against visceral hypoxia. Both laboratory and clinical data cited above point to the hypothesis that neuropsychiatric and functional gastrointestinal abnormalities in autism, ameliorated by secretin, may be secondary to hypoxia. Friedman et al (1986) found that hypoxic gut epithelial cells were impaired in their ability to generate cAMP and that pharmacologic elevation of cAMP in hypoxic cells normalized both polymorphonuclear-induced permeability changes and restoration of barrier function. Such permeability changes have been found in autistic children (D'Eufemia, et al., 1996). Horvath, et al., (2002) found that secretin, which is known to elevate cAMP (Fremeau, et al., 1986), decreased intestinal permeability in 13 of 20 autistic children. Systematic postmortem and neuroimaging studies are required to test whether neurotransmitters and neuropeptides in the cardiovascular and gastrointestinal control regions of the medulla oblongata (Iadecola, et al., 1993; Ruggiero, et al., 1993, 1996; Talman, et al., 2001) are impaired in autism.

Potential Transport Mechanisms

In the seminal study by Horvath, et al., 1998), secretin was administered intravenously, altering the behavior of three autistic boys. Secretin administered in this fashion may have had a central effect via one or more of several mechanisms. Certain proteins are known to have specific transporters in the blood-brain barrier membrane that selectively transport them from blood to CSF (Banks, et al., 1996). According to Banks, et al., pituitary adenylate cyclase-activating polypeptide (PACAP), for example, a member of the secretin/glucagon/ vasointestinal peptide family, has been shown to have both saturable and nonsaturable transport systems. Their studies demonstrated that a secretin analog crossed the blood-brain barrier and the choroid plexus in amounts that, with other members of the secretin receptor complex family, produce central neural effects (Banks, et al., 1996). Endogenous or exogenous secretin may have a similar transport system.

A Third Ventricular Route

The finding that secretin activated c-fos in ependymal cells indicate that secretin may play a role in modulating functions of limbic nuclei related to the periventricular region. Limbic structures bordering the cerebral ventricles reveal neuropathological changes on postmortem analysis of autistics (Bauman, et al., 1985, 1993). Periventricular transmitter systems that are dysregulated in autistics, such as that of serotonin (Chugani, 2002), interact with supra- and subependymal plexuses. These nonneuronal interactions may coordinate cerebrospinal fluid and vasomotor activity and central signaling (Chan-Palay, 1976, Nguyen, et al., 2001). Serotonin and ATP cause opposite changes in beat frequency of ciliated ependymal cells, implying that these cells are actively involved in central neural signaling (Nguyen, et al., 2001). It is conceivable that transient perinatal hypoxia increases the vulnerability of ependymal function, as changing hydrostatic pressures can cause mild dilations of the ventricular system and untoward effects on the corpus callosum and hippocampus, that are abnormal in autism (Bauman, et al., 1985; Harden, et al., 2000; Sparks, et al., 2002). Secretin, as predicted by the early genetic response that determines late gene expression patterns, may compensate ependymal dysfunction. Thirty-eight out of 51 consecutive autopsies on neonates revealed focal defects of the ependyma of the lateral ventricles (Friede 1975). These autopsy studies warrant analysis of the periventricular zone of autistic brains.

Data indicate that secretin-stimulated c-fos activated brain regions and supports a functional neuroanatomical basis for a long-suspected behavioral regulatory role for secretin.

Secretin, like other neuropeptides, is released in response to a variety of stressors that are faced during the human perinatal brain growth spurt (Lucas, et al., 1980), a period that is characterized by surges of stress hormones and neuropeptide modulators (van Eerdenburg, et al., 1994). Since secretin has been found to be elevated in term and preterm infants (Lucas, et al., 1980), the question remains whether secretin might be inadequately upregulated in some autistic neonates. Secretin may be synthesized by the hypothalamus (Fuxe, et al., 1979; Welch, et al., submitted) and may be transiently upregulated to coordinate behavioral and autonomic responses to homeostatic challenges such as perinatal hypoxia, excess gastrointestinal HCl output, starvation, and excess somatomotor activity (Bell, et al., 1984; Lucas, et al., 1980). Since secretin is normally upregulated in neonates (Lucas, et al., 1980), exogenous secretin might act to modulate the dysregulated autistic stress adaptation axis (Tordjman, et al., 1997).

Given the likelihood of activation by tanycytic mechanisms (Flament-Durand and Brion, 1985; Rodriguez, et al., 1979), blood-brain barrier transport, or secondary activation via the vagus and related cranial nerves, secretin might have therapeutic effects if administered intravenously (Coniglio, et al., 2001; Horvath, et al., 1998; Lightdale, et al., 2001; Sandler, et al., 1999), subcutaneously (Harada Syuto 1993), or transdermally (Lamson, et al., 2001) according to a physiologic dosing schedule. If the efficacy of secretin therapy depends on the amount and timing of exogenous secretin reaching brain tissues, then recent successful strategies for developing chimeric protein vectors to deliver peptides to the brain (Bickel, et al., 2001) may offer increased promise for the therapeutic use of secretin in autism.

Secretin alters the activity of structures involved in behavioral conditioning of stress adaptation and visceral reflex reactions. A possible cellular mechanism, activation of third ventricular ependymal and subependymal cells, was demonstrated by this study, providing evidence in support of central regulatory actions of secretin, possibly explaining some of its behavioral effects in autistic children. Mature ependyma may regulate the transport of small bioactive molecules, as well as water and ions, between the cerebrospinal fluid and neuropil (Bruni, 1998). Secretin regulates metabolism of peripheral (Schwarzschild, et al., 1989) and central catecholamine metabolism (Fuxe, et al., 1979). The present study extends these findings by demonstrating activation of catecholamine-modulated periventricular structures such as the NTS, area postrema, LC, periventricular thalamic and hypothalamic nuclei, and cerebral cortex, as well as the ependyma of the third ventricle. The physiological effects of secretin on behavioral, endocrine, autonomic, and sensory neuronal activation patterns all contribute to central c-fos activation. Together, the existence of a central secretin receptor complex (Nozaki, et al., 2002) and the known effects of secretin on behavior (Charlton, et al., 1981) and on peripheral neurotransmitter metabolism (Schwarzschild, et al., 1989), combined with the clinical effects observed in autistic children (Horvath, et al., 1998), mandate further investigation of secretin as a brain/gut stress regulatory hormone.

Example 2

In the following study, the inventors sought to determine whether secretin is synthesized centrally, specifically by the hypothalamic-pituitary-adrenal (HPA) axis. The inventors demonstrated secretinergic immunoreactivity in the hypothalamus of a rat. The inventors also demonstrated that secretin levels were up-regulated by colchicine, an exemplar of homeostatic stressors, as compared with low constitutive expression in untreated rats.

Methods

Experiments were performed on 12 male Sprague-Dawley rats (250-300 grams) maintained in a thermally controlled, light-cycled environment with lab chow and water ad libitum.

Colchicine pretreatment was necessary to identify secretin immunoreactivity product in neurons expressing constitutively low basal secretin immunolabeling as shown in pilot studies of untreated animals (n=6). Colchicine, a metabolic stressor, acts by disrupting the microtubule network and by blocking axonal transport leading to a buildup of cytoplasmic peptide content in quantities adequate for immunocytochemical detection (Aguado, et al., 1999). Colchicine was injected into the lateral ventricle and two days later, brain tissues sections were immunocytochemically processed to detect secretin. Rats were deeply anesthetized by intraperitoneal (i.p.) administration of ketamine/xylazine, and 10 J.l.1 of colchicine solution (15 µg/µl 0.9% saline) was slowly microinjected unilaterally into the right lateral ventricle through a glass pipette inserted via a burr hole in the skull. Age-matched controls were administered equal volumes of physiological saline. Wounds were closed and animals were returned to their cages. After 48 hours, animals were deeply re-anesthetized with ketamine/xylazine i.p. and perfused transcardially with heparinized, physiological saline followed by a fixative containing 4% paraformaldehyde in 0.1 M phosphate buffer (pH 7.4). The forebrain was blocked and removed from each animal, postfixed for 1 h in the same fixative and cryoprotected overnight at 4° C. in 0.1 M phosphate buffered saline (pBS, pH 7.4) containing 10% sucrose. Frozen tissues were sectioned in the transverse plane at 30 microns on a sledge microtome and collected in phosphate buffer. Free-floating serial sections were incubated for 18-24 h in commercially available, highly specific polyclonal rabbit antibodies raised against secretin (Chemicon International, Inc., Temecula, Calif.), vasoactive intestinal peptide (VIP), pituitary adenylate cyclase-activating polypeptide (PACAP), or glucagon (phoenix Pharmaceuticals, Inc., Belmont, Calif.). The antisera were diluted (1:10,000) in tris-buffered saline (TBS) containing 0.1% bovine serum albumin to which 0.25% Triton X-100 was added to facilitate tissue penetration. Alternate tissue sections were rinsed in TBS (3×15 min), incubated (1 h) in 1% BSA in TBS and processed immunohistochemically, using an immunoperoxidase ABC technique. Tissues were sequentially incubated in biotinylated goat anti-rabbit immunoglobulin (IgG) secondary antibody (1:200, 60 min) and avidin-biotin peroxidase complex (1:100, 60 min) (Vector, Burlingame, Calif.). Immunocytochemically processed sections were washed in Tris (3×15 minutes), and treated with 0.05% diaminobenzidine hydrochloride in dilute phosphate buffer containing 0.003% hydrogen peroxide to develop the reaction. Sections were mounted on 1% gelatin-coated slides, air-dried, and coverslipped without counterstaining. A set of adjacent sections were Nissl stained to delineate nuclear borders. Sections were examined by light microscopy and digitized images were obtained with a Diagnostic Instruments SPOT-RT Slider camera mounted on a Nikon Microphot microscope. Forebrain nuclei were identified by reference to Nissl stained sections and stereotaxic atlases of the rat brain (Paxinos, et al. 1998; Swanson 1998).

Controls

The specificity of the secretin staining pattern was determined by internal controls comparing the distribution patterns of secretin, VIP, P ACAP and glucagon. Controls for the specificity of the antibodies included 1) omission of the primary antibodies or 2) substitution of normal rabbit serum for the primary antiserum and preincubation of the secretin antibody by pre-adsorption with secretin peptide (Sigma) or VIP, or P ACAP peptide (Phoenix Pharmaceuticals). Working solution containing each of the peptides in 0.1 TBS/1% bovine serum albumin, pH 7.55, was incubated on a slow shaker table at 4° C. overnight, with the primary secretin antibody (dilution 1:10,000). Incubation of the conjugate, 1:10 ratio of secretin Ab/peptide (secretin, VIP, or P ACAP) was carried out and the reaction was allowed to proceed for 24 hours, followed by ten minutes centrifugation. The tissue sections were incubated in the resulting supernatant overnight at room temperature, followed by standard immunocytochemical methods.

Results

Figure 7:
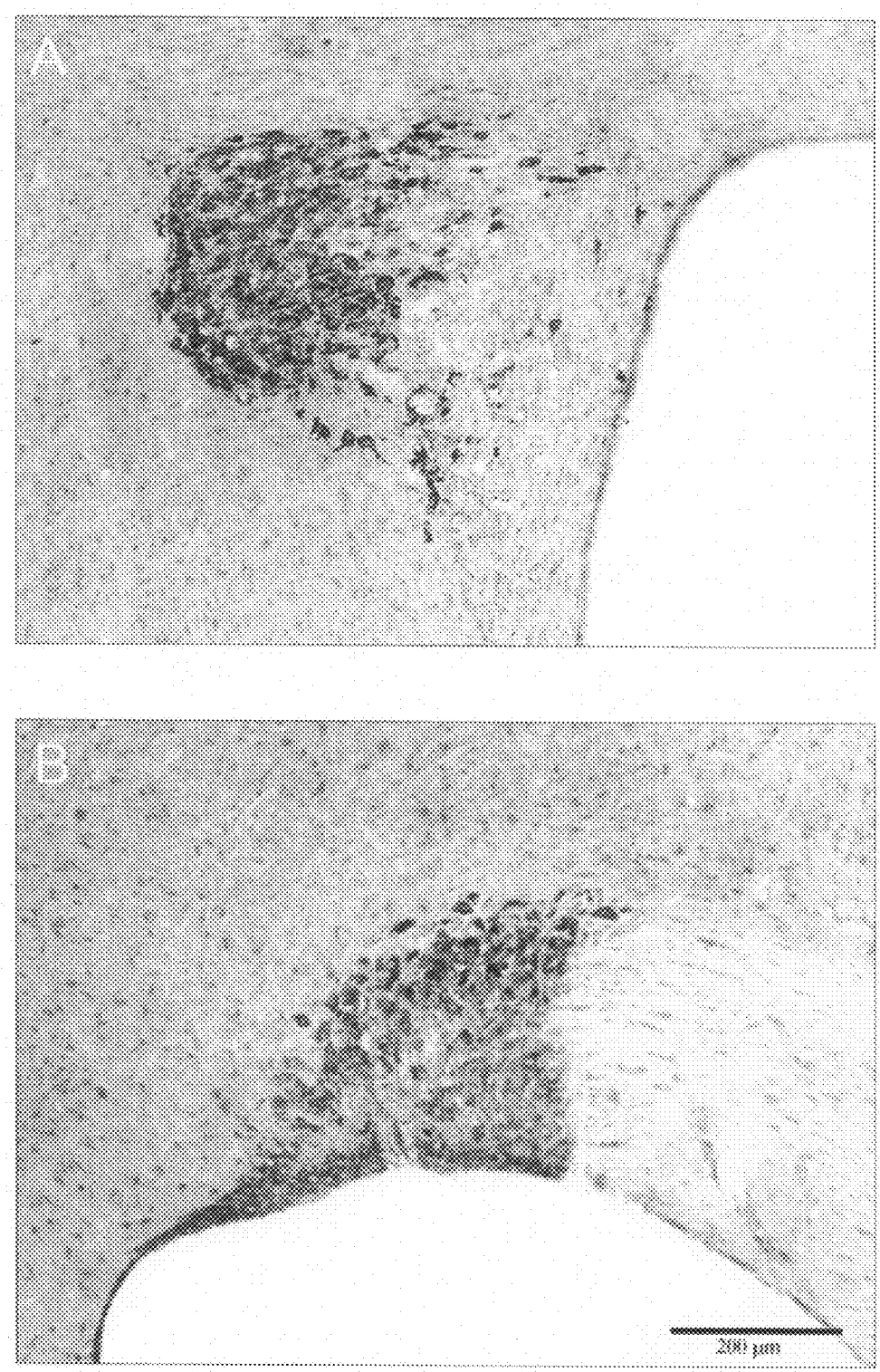
FIG. 7 depicts presumptive secretinergic neurons in the hypothalamic (A) paraventricular nucleus (PVN), and (B) supraoptic nucleus (SON) of a colchicines treated rat. Note the topographic distribution of neuronal cell bodies and the dense labeling of the neuropil representing neuronal processes. The ependyma bordering the third ventrical demonstrate moderate labeling.
Figure 8:
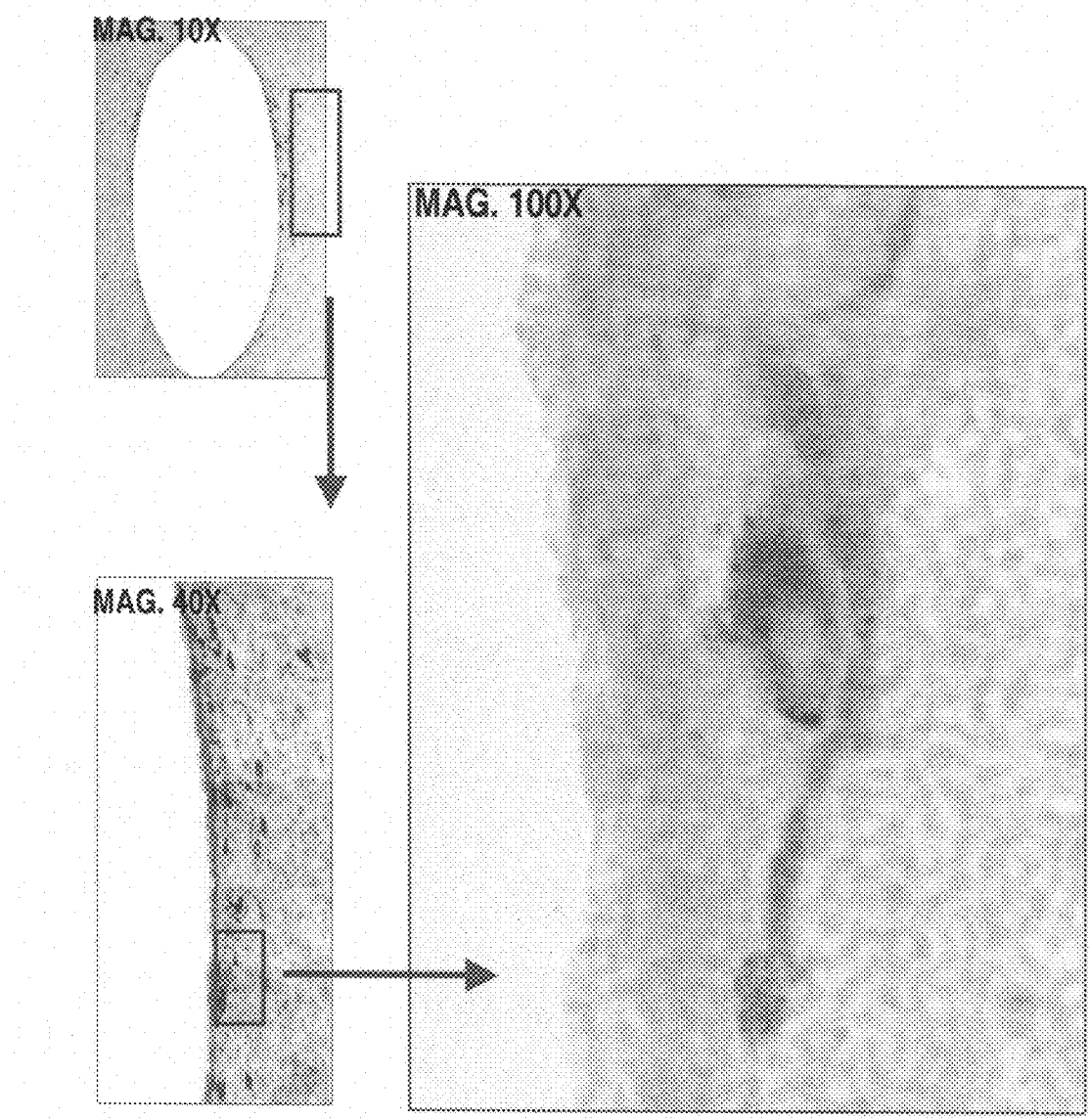
FIG. 8 shows evidence suggestive of secretin exchange across the CSF/ependymal interface of the third ventricle. A secretinergic neuron in the rat periventricular gray in proximity to the ependyma is characterized by diffuse cytoplasmic immunoreactivity. Preadsorption controls verified the labeling of neuronal cells. Theoretically, secretin may be secreted into, or extracted from, the CSF. The peptide is up-regulated on demand and secreted into the CSF and the blood stream, and released by terminals of hypothalamic/pituitary/bulbar/spinal projections. Suspected interactions may occur with classical neurotransmitter systems, such as serotonin and dopamine and other stress regulatory peptides, such as CRH, AVP and OT.

Secretinergic neurons were heavily labeled in colchicine-treated rats, as compared with the untreated group, which showed light to undetectable labeling. Secretin immunoreactivity was cytoplasmic and restricted to neurons of the anterior and middle regions of the hypothalamus and adjoining periventricular gray. The hindbrain, cerebellum and spinal cord were not examined in this study. Presumptive secretinergic neurons were concentrated in precise loci within the paraventricular/supraoptic and intercalated regions of the hypothalamus (FIG. 7). Secretinergic S cells were heavily concentrated and intensely stained in both the peripheral and central core of the paraventricular nucleus magnocellularis, and labeled in its medial extensions into the parvicellular and peri ventricular divisions. S cells in the supraoptic nucleus (SON) were concentrated dorsally and extended medially arching over the optic tract. Small numbers of cells were scattered among a heavily labeled neuropil in the ventral region of the SON. Arrays of cells were diagonally organized in the nucleus intercalatus. High power optics revealed secretinergic neurons with subependymal processes in the peri ventricular gray deep to the ependyma that contained homogeneous granular reaction product (FIG. 8).

Controls: Preadsorption

Figure 9:
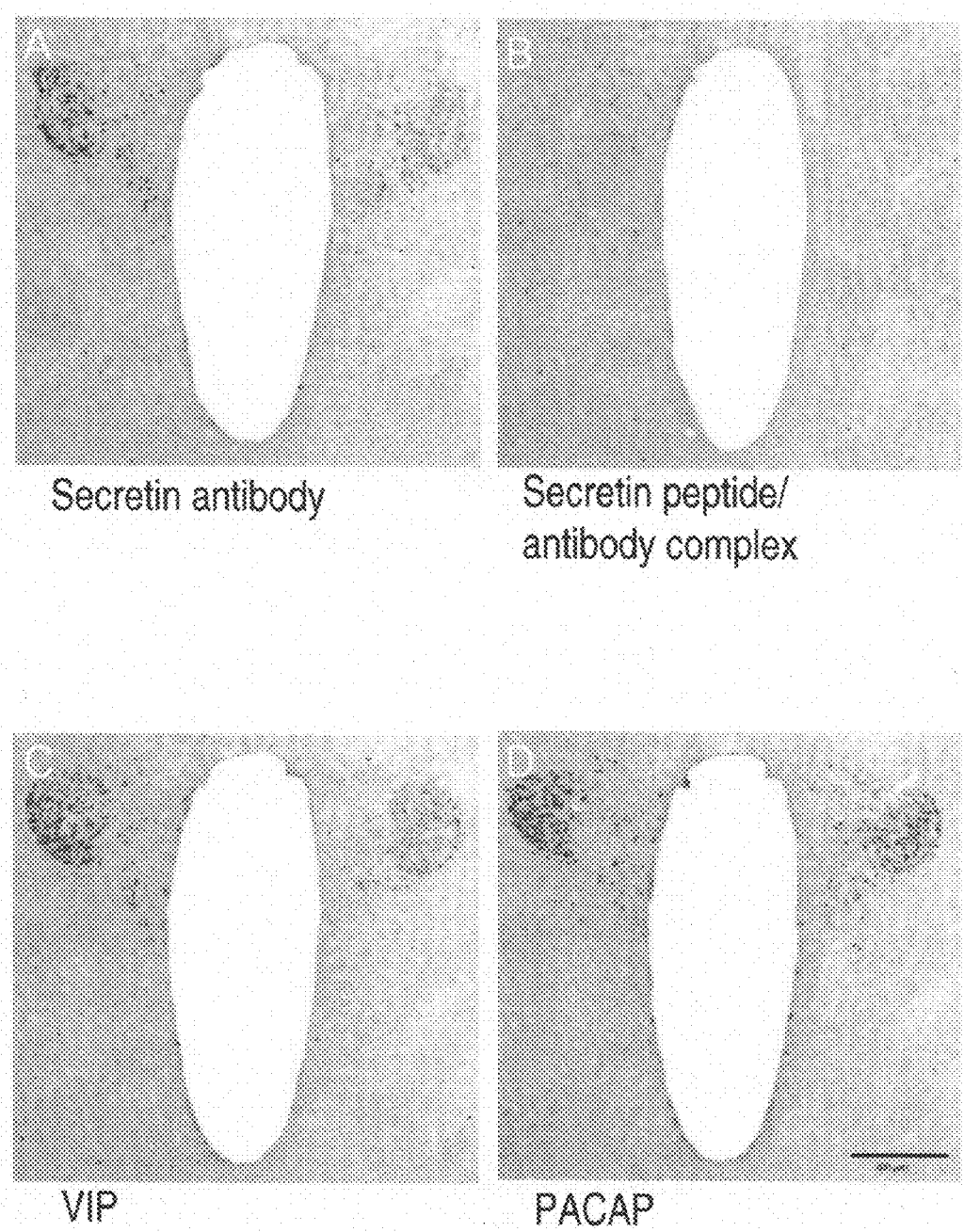
FIG. 9 depicts preadsorption study in paraventricular hypothalamus (PVN). (A) Secretinergic neurons in PVN on cross-sectioned tissue incubated in secretin antibody. Specificity was verified by absence of immunoreactivity on tissue incubated in the (B) secretin peptide/antibody complex, and the robust labeling of secretinergic hypothalamic neurons on tissues incubated in antibody preadsorbed with (C) VIP or (D) PACAP.
Figure 10:
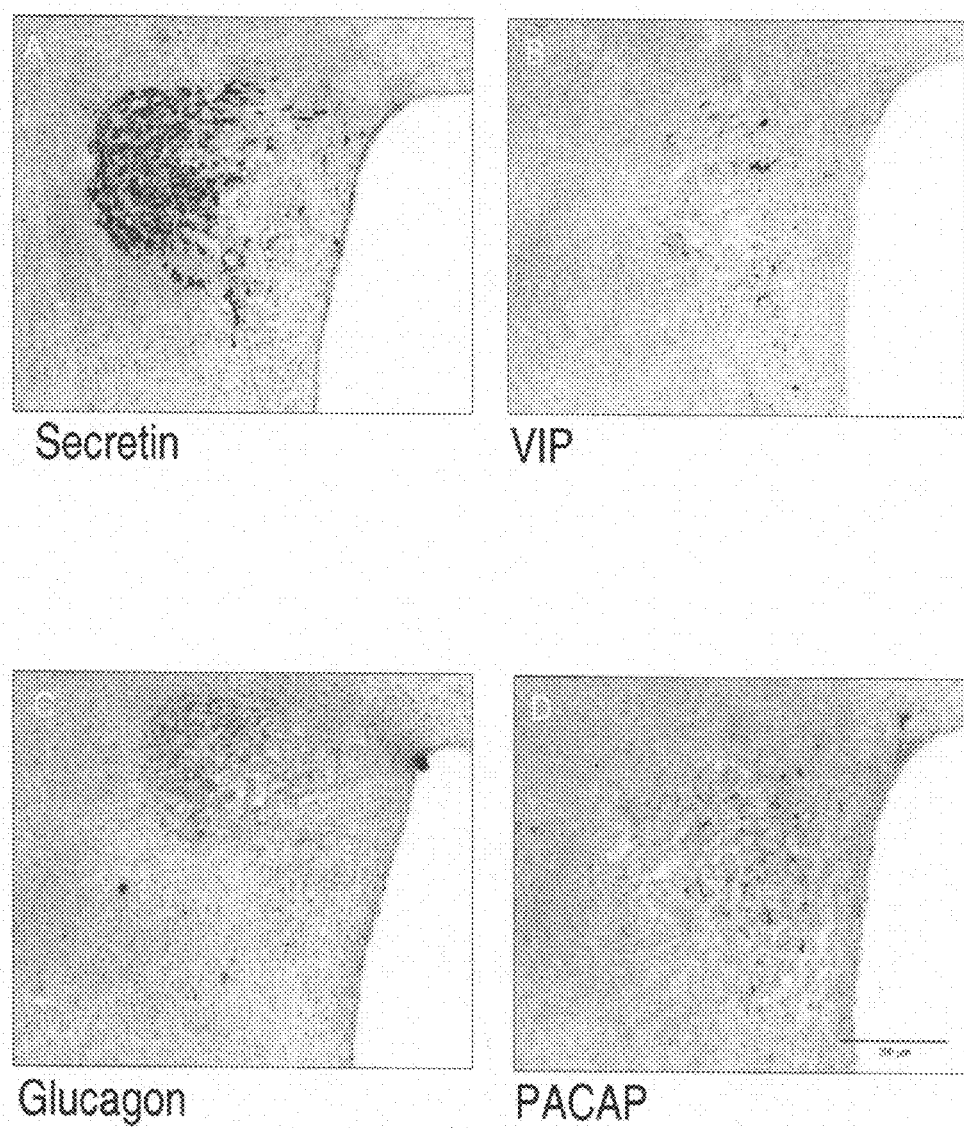
FIG. 10 shows distribution patterns of the secretin peptide family in the paraventricular nucleus (PVN) of colchicines treated rat. Secretinergic neurons in the hypothalamus on tissues were incubated in a rabbit polyclonal antibody raised against: (A) secretin, (B) VIP, (C) glucagons and (D) PACAP. They were characterized by different distributional and density patterns. Specificity of the antibody was verified by the cross-comparisons of the secretin family of peptides and by internal controls.

The specificity of secretin immunoreaction product was verified: secretin immunoreactivity was not detected on tissue sections that were incubated in secretin antibody that was preadsorbed with the secretin peptide as shown in the PVN (FIG. 9). Secretinergic neurons and ependyma were immunolabeled on alternate tissues that were incubated in secretin antibody preadsorbed with another member of the secretin peptide family: VIP or PACAP.

Controls: Cross Comparisons

Figure 11:
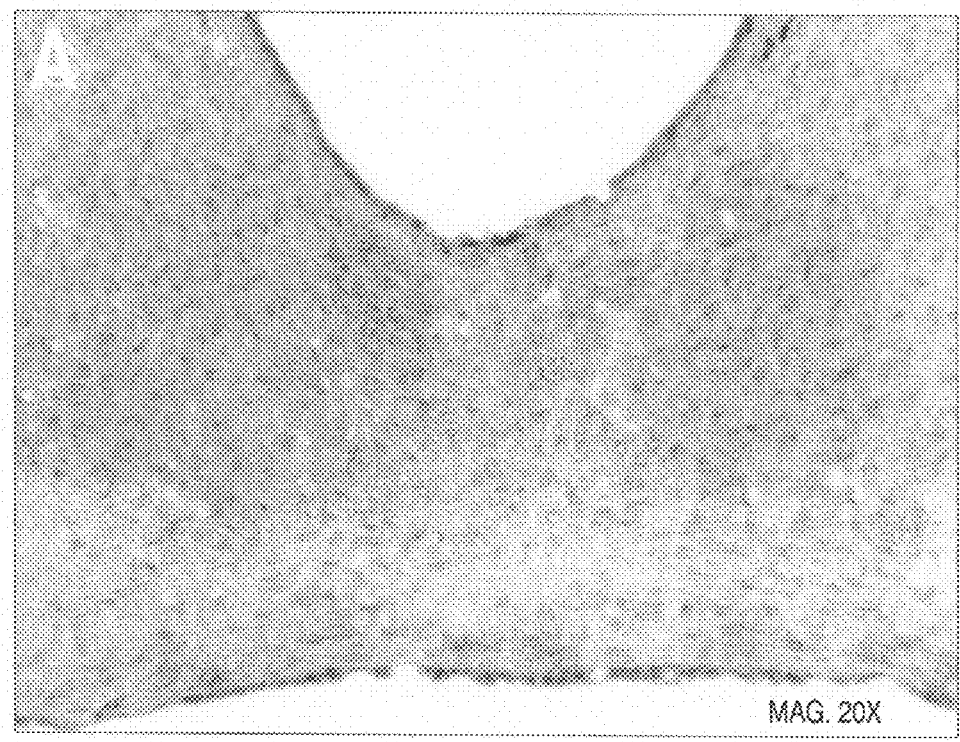
FIG. 11 shows photomicrographs of Fos immunostained sections of the IL10−/− mouse suprachiasmatic nuclear (SCN) in the medial basal hypothalamus (A) Compare the patterns of c-fos distribution in the animal with IL 10−/− genetic IBD following placebo treatment with physiological saline infusions with those administered bioactive hormone therapy. Note that the bed nucleus of the stria terminalis is devoid of c-fos protein immunolabeling pattern; (B) Note the striking bilateral activation of the SCN of an IL10−/− mouse with Secretin/Oxytocin peptide therapy. Note that the activation extended rostrally into the preoptic suprachiasmatic pole. Note the dramatic increase in c-fos reactivity of the bed nucleus of the stria terminalis in an animal with confirmed resolution of IL10−/− colitis after treatment with 7 days of I.P. infusion of peptides.
Figure 11:
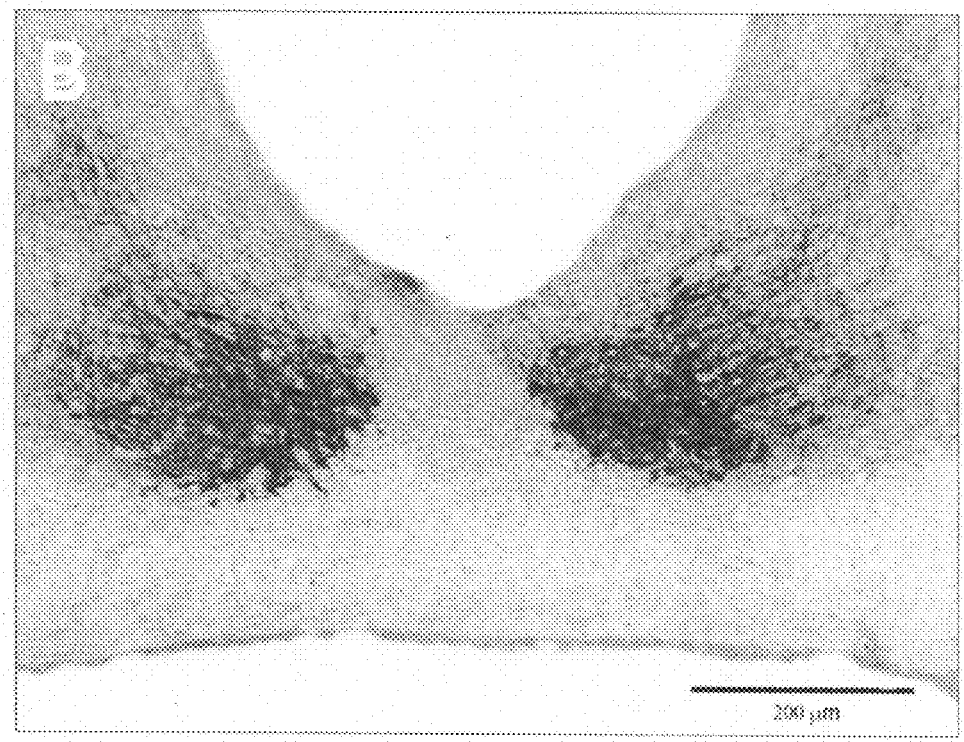
Figure 12:
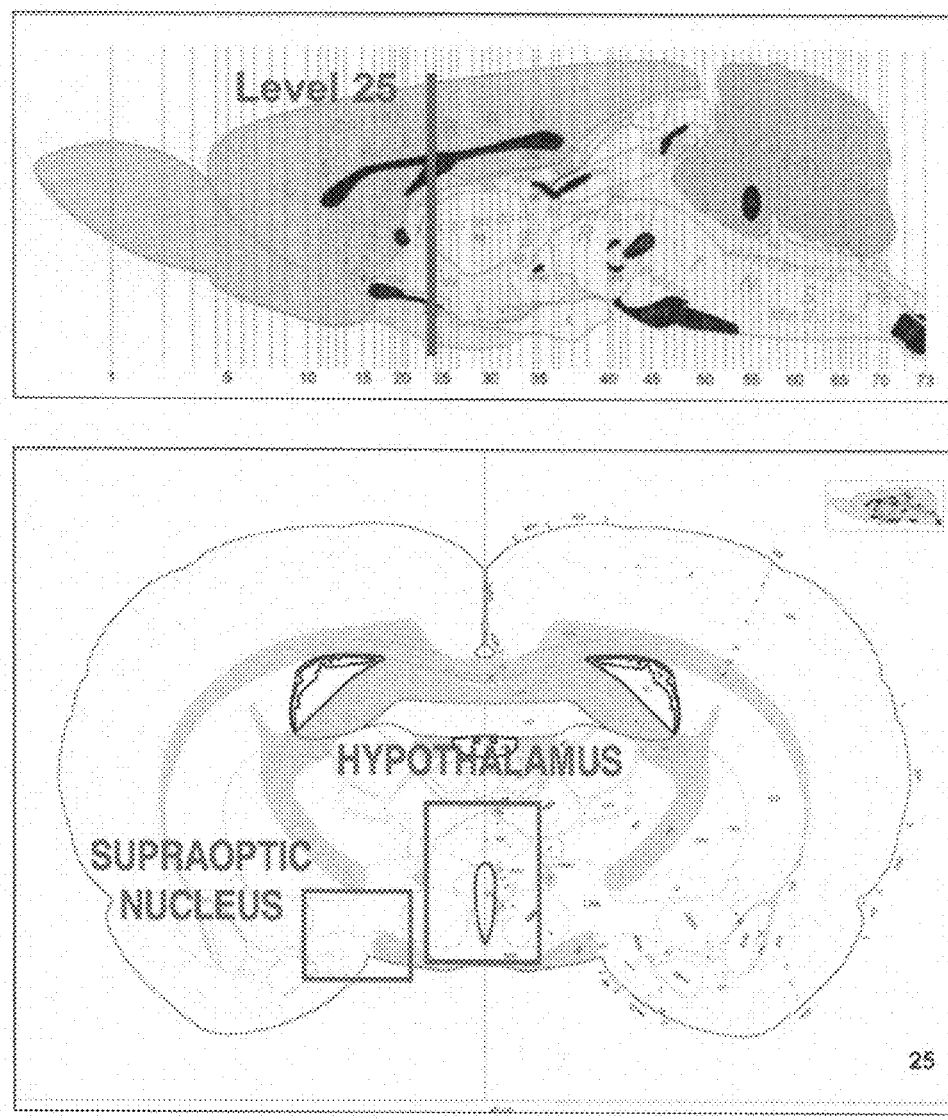
FIG. 12 depicts Swanson Brain Maps: Schematic Level 25. Secretinergic neurons shown in previous Figures were localized to the paraventricular (PVN) and supraoptic (SON) hypothalamic subnuclei depicted the forebrain level.

Distribution patterns of secretin immunoreactive neurons were distinct from the distribution patterns on tissues incubated in antibodies raised against the other members of the peptide family (FIG. 11). These dramatic differences in topographic distribution and density served as an internal control in colchicine-treated animals. Their locations differed from the distributions of other members of the secretin/VIP/glucagon/PACAP family, as delineated on serially sectioned alternate tissues processed with respective antibodies raised against each peptide. Secretinergic neurons in PVN and SON far outnumbered cells staining for the other peptides, including VIP.

VIP labeling was expressed in superficial and deep layers of the cerebral cortex and striatum with a distinct distribution in the anterior cingulate and contiguous medial prefrontal cortex and lateral prefrontal cortex. VIP staining was light and diffuse in the supraoptic nucleus and weak in the PVN with the exception of intensely stained cells and neuropil in the hypothalamic suprachiasmatic nucleus (SCN) (FIG. 11). The caudate and putamen demonstrated small spindle-shaped cells that resembled interneurons.

Glucagon appeared in the retrochiasmatic nucleus and extended dorsally into the, subparaventricular zone of the hypothalamus and in plexuses of the internal and external lamina of the median eminence, the neuropil of PVN, SON, caudate and putamen. Further contrasting secretin-staining patterns was heavy labeling of the basolateral amygdala.

PACAP staining was dramatically different from the secretin patterns, exhibiting high concentrations in processes of the basolateral and lateral amygdala and lighter labeling in the central nucleus. P ACAP was present in PVN cells but skewed medially in the parvicellular region. Scattered labeling in the SON was concentrated ventrally where the bulk of the labeling appeared to be in the neuropil.

Secretinergic cells were not detected in regions containing moderate to high concentrations of glucagon, VIP or P ACAP. These other peptides had distinctive distribution patterns and were localized to regions devoid of secretin or, where there was overlap, were characterized by low levels of immunoreactivity. Loci enriched in secretin immunoreactivity were devoid of or characterized by low levels of glucagon or P ACAP immunoreaction products.

This study provides the first single-cell immunocytochemical demonstration of secretinergic immunoreactivity in the hypothalamus of a rat, extending earlier data obtained using less sensitive techniques (Mutt 1979; Charlton, et al., 1981; O'Donohue, et al., 1981; Samson, et al., 1984; Chang, et al., 1985). Based upon observations made in this study, a novel concept for the neurobiological basis of secretin's role in autism is created by synthesizing previous medical and experimental literature with these findings.

Secretin is Synthesized by Neurons in the Hypothalamus

Secretin-like neuronal immunoreaction product is restricted to the hypothalamus and adjoining periventricular gray. Secretin immunolabeling in this study was neuronal and was restricted to precise loci within the paraventricular/supraoptic nuclei and adjoining periventricular gray (FIG. 7). Control studies support specificity of secretin immunoreactivity. Dramatic differences in topographic distribution and density of secretinergic neurons from the distribution patterns of other members of the secretinNIP/glucagonIP ACAP family extend evidence of the existence of a secretinergic brain/gut stress regulatory system. The number of cells staining for secretin far outnumbered those staining for VIP, glucagon and PACAP. Yet another related peptide, hypocretin, shares substantial amino acid identities with secretin. However, hypocretin, in contrast to secretin, localizes to neuronal cell bodies in the dorsal posterior hypothalamus and amygdala (deLecea, et al., 1998; Ciriello, et al., 2003).

Previous studies using immunocytochemical techniques failed to find secretin in the hypothalamus (Koves, et al., 2002; Ng, et al., 2002). The data from this study, however, which were supported by extensive control experiments, support earlier studies that found hypothalamic secretin expression (Fuxe, et al., 1979). Secretin precursor protein is abundant in the hypothalamus and hippocampus (Itoh, et al., 1991), sites of pathology in autism (Bauman, et al., 1985). These data indicate that secretin may serve as a bioactive stress regulatory peptide in the rat brain, specifically along the HPA stress axis. The fact that the hypothalamus plays a key role in regulating brain/body functions indicates that secretin in related to various homeostatic functions.

Secretin Regulates Stress Centrally as Well as Peripherally

Secretin has been predicted to be a stress regulatory peptide (Fuxe, et al., 1979; Itoh, et al., 1991). Secretin's role as a peripheral stress-regulatory hormone and central neuromodulator of stress-adaptation responses has been suggested by earlier structural and functional studies (Mutt, et al., 1979; Charleton, et al., 1981; O'Donohue, et al., 1981; Samson, et al., 1984; Chang, et al., 1985). Since secretin is expressed along the HPA stress axis, the inventors postulate that the neurohormone receptor expression and its interactions with other transmitter/modulators should be studied in relationship to homeostasis. In particular, the fact that secretin was up-regulated by colchicine provides evidence of secretin's central expression. In this study, secretin staining in the brain was scant in intact rats, reflecting the fact that under normal physiological conditions the level of central secretin in the adult rat may be low. However, in this study the experimental rats were exposed to colchicine, which acts as a powerful oxidative stressor. In cases of toxicity, it has been shown to cause respiratory and renal failure in the treatment of gout, impairments of cognition, learning and memory (VeerendraKumar, et al., 2002), and even death in humans (Jones, et al., 2002). Secretin levels are elevated in other conditions of stress, such as severe dynamic exercise (Oektedalen, et al., 1982; Bell 1984) and restraint stress/hypoxia (Lauterbach, et al., 1980). This indicates that secretin may have been upregulated by colchicine because it is a physiological stressor.

Stress-Related Dyregulation of Brain/Gut Peptides in Autism

No study to date has measured bioactive peptide production levels in the autistic brain. Colchicine up-regulation of secretin, as well as oxytocin (Bojanowska, et al., 1999), may replicate the effects of stress on brain/gut peptides in autistics. Clinical evidence suggests dysregulation of peripheral VIP in neonates later diagnosed as autistic (Nelson, et al., 2001). This raises the question whether other stress regulatory peptides are dysregulated in autism. If so, this dysregulation could explain the reported effectiveness of hormone replacement therapies, such as secretin (Horvath, et al., 1998) and oxytocin (Hollander, et al., 2003b), in ameliorating autistic symptoms. Autism, along with other developmental disorders, has long been linked to adverse intrauterine environmental conditions, such as hypoxic/ischemic insult (Davis, et al., 1992). Such insults have been causally related to brain/gut pathology (Barlow, et al., 1975). Since hypoxia stimulates secretin release (Lauterbach, et al., 1980), it is possible that the failure of autistic infants to communicate and affiliate is in part a consequence of visceral disorders (Horvath, et al., 1999), including abnormalities of secretinergic systems (Gershon 2003 personal communication). In such cases, adverse visceral environmental conditioning of brain/gut response patterns may be related to the pathophysiology in autism, such as perceptual, social and intellectual impairments, and stress-related symptomatology.

It is well established that cognitive and emotional networks are dysregulated in autism (Rumsey, et al., 2000), and that these networks control visceral reflex function at the ventral and dorsal vagal complex (Ruggiero, et al., 1985; Loewy 1991). Moreover, the HPA stress axis and the sympathetic projections to the viscera are hyperdriven by high unremitting stress (Steptoe, et al., 1999; McEwen 2001). Secretin S cells may be similar to epinephrine neurons, which exert powerful influence over behavioral and visceral reflex functions (Sved, et al., 1994). Both are exquisitely sensitive to chronic homeostatic perturbations, such as hypoxia, and are upregulated by colchicine (Ruggiero, et al., 1985, 2003).

Stress-related hyperproduction of secretin might remodel the secretin receptor complex. The endocytic process of secretin receptor internalization, identified by Walker (Walker, et al., 1999), could be compromised over time by such remodeling, which in turn could compromise secretinergic function. Some recent research on secretin-mediated gene delivery supports this concept (McKay, et al., 2002).

Stress-Related Dysregulation of the GI Tract in Autism

Under conditions of unremitting stress, or in response to chronic homeostatic perturbations, the secretin S cells, like epinephrine cells, may be activated on demand (Sved, et al., 1994) and thus driven to depletion or apoptosis through overuse. Indeed, Gershon found markedly fewer S cells in the upper gastrointestinal tracts of autistics, as well as fewer cells co-localizing secretin and serotonin (Gershon 2003 personal communication). In addition, secretin levels are elevated in diseases such as cystic fibrosis, hyaline membrane disease (Boccia, et al., 2001) and Crohn's disease (Teufel, et al., 1986), all of which are associated with gastrointestinal abnormalities. Friedman found that hypoxic gut epithelial cells were impaired in their ability to generate cAMP, and that pharmacologic elevation of cAMP in hypoxic cells both normalized polymorphonuclear-induced permeability changes and restored barrier function (Friedman, et al., 1998). Such permeability changes have been found in autistic children (D'Eufemia, et al., 1996). Horvath found that secretin, which has been shown to elevate cAMP (Fremeau, et al., 1986), decreased intestinal permeability in 13 of 20 autistic children (Horvath, et al., 2002).

Clinical Support of the Hypothesis that Secretin is Synthesized on Demand in Response to Stressors Secretin-releasing peptide and secretin are secreted as part of unified, vagally mediated behavioral and reflex response patterns (Chey, et al. 2001). These peptides are triggered by stress-related increases in gastrin and gastric acid output (Li, et al., 1998). Interestingly, this reflex response pattern is viscerally conditioned by components of maternal nurturing, such as breast-feeding and vocalization, which condition a child to alternated between swallowing and breathing, or to alternate between talking and listening (Porges 1995). Stimuli, such as sucking, feeding and tactile vicerosomatic stimulation, activate periventricular/tegmental pathways which are predictably involved in the development and differentiation of visceral memory. Behavioral, endocrine and autonomic networks that are assembled postnatally (Rinaman, et al., 2000) were found to respond to secretin (Welch, et al., 2002a,b). These findings indicate that these networks could have been dysregulated as the result of stress and by visceral disorders.

Synthesis and secretion of secretin on demand may be operative in amelioration of perinatal stress (Rogers, et al., 1975, Lucas, et al., 1983) via two mechanisms of action: as a vasodilator (Gandhi, et al., 2002), and as a gastric protective hormone (Bayliss, et al. 1902). Brain-stem tegmental pathways vasodilate cerebral blood vessels (Golanov, et al., 2000). Human neonates exhibit excessive gastric acid and secretin output, as assayed in two-day old neonates, whereas secretin hyper-expression reaches the mature pattern by the second postnatal week in healthy pre-term infants (Lucas, et al., 1980). Sick infants with hyaline membrane disease exhibit sustained up-regulation of secretin secondary to both starvation (Lucas, et al., 1980) and respiratory stress, as induced by colchicine (Jones, et al., 2002).

Secretin is secreted in response to milk ingestion (Mineo, et al., 1990). The colostrum content of breast milk during the immediate post-partum period is an even more powerful stimulus to secretin than milk (Guilloteau, et al., 1992). There is a relationship between maternal withdrawal from breast-feeding and autism; studies on infantile autism revealed lower incidence of breastfeeding (Tanoue, et al., 1989). Brain/gut peptides involving a behaviorally-modulated vagal reflex are released in response to breastfeeding (Eriksson, et al., 1994). Consequently, brain-gut peptides are implicated in the acute and long-term effects of breastfeeding. These findings suggest that early weaning may contribute to the etiology of autism. Further, they suggest that restoration of components of maternal nurturing (Tinbergen, et al., 1983; Welch, et al., 1983a,b, 1987, 1988, 1989) and/or peptide therapy (Welch, et al., 2003b) might replicate the protective effects of holding and/or breastfeeding, as found in Barlow's studies (Barlow, et al., 1975). The combined therapies of reinstatement of components of maternal nurturing and peptide hormones should be evaluated by neuroimaging and assays of brain/gut peptide levels in both mother and autistic child.

Secretin Interactions with Other QeQtides and Neurotransmitters

Contemporary research investigates the function of visceral reflex circuits responsible for homeostasis (Agassandian, et al., 2002; Talman, et al., 1993; Wasserman, et al., 2002). Signaling molecules interact in the regulation of homeostasis and the stress response, notably via the paraventricular hypothalamus (Leong, et al., 2002). Such interactions between classical neurotransmitters and peptides include: dopamine and secretin, norepinephrine and secretin (Fuxe, et al., 1979), angiotensin and secretin (Walker, et al., 1999), epinephrine, norepinephrine and angiotensin (Li, et al., 1996; Jezova, et al., 1999), norepinephrine, serotonin and oxytocin (Vacher, et al., 2002) and oxytocin and atrial natriuretic peptide (Chirguer, et al., 2001).

An example relevant to gastrointestinal disorders is the relationship between angiotensin and secretin receptors. Angiotensin II AT(1) receptors and secretin receptors are co-localized in endocytic vesicles (Walker, et al., 1999). Angiotensin II AT(1) receptors are linked to social isolation stress (Armando, et al., 2001). Antagonizing AT(1) receptors restores modulation of HPA stress axis function (Armando, et al., 2001) and prevents gastric mucosal injury (Bregonzio, et al., 2003). Social isolation stress is a causal factor in hemorrhagic stress ulcers and hippocampal formation pathology among insubordinate vervets (Uno, et al., 1989). Autistic children and insubordinate vervets both experience social isolation and share non-compliance behaviors (Breiner, et al., 1984). The cingulate/hippocampal stress adaptation network is also a major site of pathology for both autistic children and vervets (Bauman, et al. 1985, Uno, et al., 1989). This network is implicated in the adverse conditioning of both gastrointestinal functions (Uno, et al., 1989; Gabry, et al., 2002) and behavioral functions (Jones, et al., 2001; Freeman, et al., 1997). Secretin, which activates the cingulate/hippocampal stress adaptation network (Welch, et al., 2003a), has been effective in ameliorating both gut and behavioral abnormalities of autistic children (Horvath, et al., 1998; Lamson 2001; Horvath, et al., 2002). Still to be investigated is whether secretin levels are altered by the social isolation of autistics, and whether secretin might be therapeutic in Uno's insubordinate primate stress-ulcer model (Uno, et al., 1989).

Taken together, these findings suggest that secretin, a vasodilator (Gandhi, et al., 2002), could be modulating the effect of angiotensin II AT(1), a vasoconstrictor (Helou, et al., 2003). This modulation may take place, as Leong suggests, by "cross-talk" (interaction) of peptides at the level of the hypothalamus (Leong, et al., 2002). If secretin is modulating AT(1) receptors, this interaction may explain why secretin ameliorates both GI pathology (Horvath, et al., 2002; Welch, et al., 2003b) and symptoms of autism (Horvath, et al., 1998). These findings also support the theory that autistic symptomatology is related to a dysregulation of a single, unified mind/brain/body stress axis, one that is normally conditioned by peptide/peptide and peptide/neurotransmitter interactions. If secretin is dysregulated, then its central and peripheral networks and transmitter interactions, such as with norepinephrine, dopamine (Fuxe, et al., 1979), angiotensin (Walker, et al., 1999) and serotonin (Gershon 2003 personal communication), could be dysregulated as well.

This study provides the first direct immunocytochemical demonstration of secretinergic immunoreactivity in the forebrain, and provides strong evidence that the hypothalamus, like the gut, is capable of synthesizing secretin. Since secretin is expressed along the HPA stress axis, the neurohormone receptor expression and its interactions with other transmitters/modulators deserve study in relationship to homeostasis.

The medical and experimental literatures, taken together with this data, suggest that secretin, along with other neuropeptides, plays a role in conditioning stress adaptation patterns. These findings lend support for the existence of a neuroregulatory functional interdependence (synchronization) of the central/peripheral stress-response systems. This study demonstrated localizations of secretin that overlap with those of other stress-regulatory neurohormones, especially oxytocin (Vacher, et al., 2002, Welch unpublished data). Given secretin's expression by gut and brain cells, secretin may have an integrated peripheral and central stress-related function in maintaining homeostasis. Colchicine, an oxidative stressor, induces up-regulation of secretin. Therefore, it can be concluded that secretin may be synthesized on demand in response to homeostatic challenges. If secretin up-regulates in response to visceral stressors, this finding would shed new light on an important potential mechanism of action in autism.

Though the etiology of autism is poorly understood, as is the link between autism and gastrointestinal abnormalities (Horvath, et al., 2002, Torrente, et al., 2002, Gershon 2003 personal communication), these findings suggest that secretin may in some cases ameliorate dysregulated gastrointestinal function in autism by acting upon or influencing the brain and visceral processing networks simultaneously as a single unit.

Example 3

In this study, the inventors evaluated the efficacy of maternal intervention, including the reinstatement of specific components of maternal nurturing and establishment of synchronous attunement in cases of serious childhood behavioral disorders, including symptom complexes meeting criteria for oppositional defiant disorder. The inventors also evaluated implications of this study for neuropeptide thearpy. The inventors discovered that maternal intervention that includes reinstatement of specific components of maternal nurturing, including the establishment of synchronous attunement between mother and child, and/or treatments that replicate these effects pharmacologically, can be effective in ameliorating severe behavioral symptomology.

Study Group

Subjects were from an unselected group of children diagnosed prior to referral with two or more of the following disorders: conduct disorder, oppositional defiant disorder, reactive attachment disorder, attention deficit disorder, and attention deficit-hyperactivity disorder. All subjects were included whose parents had signed permission to publish the data, who had completed a CBCL questionnaire prior to the intervention, and who had completed one or more CBCL questionnaires after the intervention. To the extent possible, medications were discontinued prior to treatment for the duration of the two day intervention. Participating families were told to expect follow up phone calls checking their progress. Each family received calls from the staff member who had coordinated their admission to the treatment group; calls were made at intervals of 10, 30, 60, 90, 180 days, and every six months thereafter in order to monitor progress.

Personnel

The team of facilitators assisting the subjects' parents with the intervention consisted of therapists and helpers. The therapists included social workers, psychologists, and licensed professional counselors, all supervised by the senior author, a psychiatrist. Among the helpers were both young people and adults, most of whom were members of "helper families" who had previously experienced an intensive intervention of this type, and who volunteered to help bring the benefits of restored nurturing to others. Older children from the helper families served as peer mentors for subjects in their age group, encouraging them to accept their parents' efforts at greater attachment. Parent helpers affirmed to the subjects' parents that the intervention would ameliorate their disorders, and that the results of the treatment would lead to a more harmonious family life. The group setting was designed to provide the highest possible level of emotional support for the subjects' families as they expressed and sought to resolve past traumas and interpersonal difficulties.

Intervention

The intervention under study lasts eight hours per day on two consecutive days, usually a weekend. The sessions are conducted in a facility that provides a single space large enough to accommodate 6-8 families and therapists participating simultaneously, with adjacent kitchen and restroom facilities. Most of the families stay overnight in a nearby hotel.

The first day of therapy begins with a group discussion circle, during which each family member introduces him/herself and describes the presenting problems. After the group circle, families join their therapists on floor mats. All families are treated separately, within the context of the group, with specific therapists assigned to a given family. In each family, mother and child engage in an intense physical embrace, which is maintained through the full range of emotions from fear, anger and hurt to synchronous attunement and reciprocal hugging, kissing, and caressing. The initial interaction may be limited to nonverbal communication if the child has lost or has not yet developed the expressive language skills to convey his feelings, or lacks the ability to control negative behavior when in close proximity to the mother.

The therapeutic intervention is based upon restoration of components of maternal nurturing, an intervention that has been shown to reverse hippocampal deficits in animal models of maternal deprivation syndromes (Meaney, et al., 1988, 1991, Anisman, et al., 1998). As the dyad begins the holding phase of the intervention, the child typically exhibits rejection of the mother's efforts at closeness, and even aversion to the mother's physical presence. Mothers are instructed to express their hurt and anger in response to this rejection. At this point, the mothers initiate licking, nurturing, and sometimes feeding. In nearly every case, maternal licking proves to be the most powerful tool for breaking through the child's resistance to closeness and emotional regulation.

When the mother expresses her hurt and anger at being rejected by her child, the interaction typically evokes empathy in the child, even in children who never exhibited empathy prior to the intervention. Such a transition occurs best when the mother reaches a state of open expression of deep feeling, such as by sobbing or wailing uncontrollably. As the child faces the mother's deep feelings, his or her empathy leads to reciprocal soothing. Sometimes, rather than rejecting the mother, the child immediately expresses hurt, evoking the mother's empathy. In this case, the pair enters a synchronous state without the rejection phase of the interaction.

Mother and child first begin to reach synchronous attunement at the level of negative affect; subsequently, they do so in a climate of more positive affect. The transition to positive affect occurs when the child begins to feel the mother's devastation and vice versa. Once a state of attunement has been reached, verbal discussion occurs naturally and in a reciprocal manner. At this time, children often voluntarily describe past events that proved upsetting and become open to sharing their thoughts, concerns, and fears with the mother. In the state of reciprocity that comes with synchrony, the mother is able to empathize with her child's feelings, perhaps for the first time.

A complete reparative experience includes the following synchronous components of maternal nurturing: breathing in unison, deep mutual gaze, relaxation, reciprocal pleasure in each other's embrace, and open verbal and nonverbal communication. For adoptive mothers, such a resolution is often the first experience of attunement with this child. For biological mothers, and for adoptive mothers who have experienced childbirth and/or breastfeeding previously, a successful intervention is described as being similar to giving birth, or to nursing the child. In all cases, including nulliparous adoptive mothers, the experience is accompanied by deep feelings of connection with the child.

Throughout all phases of the intervention, close physical contact must be maintained. Direct expressions of feelings, such as fear, anger, or sadness, are encouraged. If verbal discussion or narrative becomes a distraction, it is discouraged, as it can hinder progress toward emotional and biological synchrony. Therapists do not interpose themselves between family members or interfere with the dyadic interaction and emotional rapprochement. Instead, therapists play a facilitative role, helping the family to identify or express emotions, encouraging direct communication of emotional content. Helpers assist the therapists and provide emotional support and encouragement to the subject families throughout the intensive family session.

In addition to mother-child sessions, other dyads, including mother-father, father-child, and parent-grandparent pairs, experience a similar process. In choosing the order of the dyads for treatment, priority is given to any relationship barriers that might be hindering the attunement process between mother and child. The focus and emphasis, though, remain on the mother-child dyad, as emphasized previously by Welch and Chaput. Other dyads are engaged as needed to strengthen the mother's feelings of confidence and security, to reach the resistant child, and to stabilize emotional support, communication and limit-setting systems within the family.

On the second day of treatment, each family discusses emotional and attunement barriers with the assigned therapists and resumes dyadic engagements until family members reach resolution. At the end of third day, a course of action is developed for each family, to be followed at home, and follow-up therapy is discussed as needed. Another group circle is held at the conclusion of the event; each person describes what he/she has experienced and what changes are felt to have occurred.

Following the initial two-day intensive family session, the family is directed to continue restoring specific components of maternal nurturing at home, as learned in the therapy sessions. Families are also instructed in parenting behaviors that reinforce and maintain family connections, encourage empathy and reciprocal behavior, and obviate the need for forms of punishment. Actions that increase attunement are recommended; actions that cause distance, alienation, or separation are discouraged.

Measurement of Effect

For each participating child, a parent was asked to complete the Achenbach Child Behavior Checklist (CBCL) before and after treatment. The CBCL has syndrome scales that measure social adjustment, levels of anxiety and depression, somaticization, and delinquent and aggressive behavior. A Total Problems score of 60 is the bottom of the clinical range. The mean baseline Total Problems score for this cohort was 72. The scores are based on percentiles for the normative sample derived from normative data drawn from a subset of non-handicapped subjects in a national US sample. Research on this instrument reported excellent test-retest reliability, interparent agreement, and construct validity.

The pretreatment questionnaire was administered immediately before the initial intervention, and the post-questionnaire was administered an average of eleven months later. The CBCLs were received via telephone, mail or facsimile. Pre- and post-test scores were compared using paired-sample t-tests.

Results

Of 95 children whose parents completed a baseline CBCL, 41 had parents who completed one or more post-treatment questionnaires. The 41 children (18 female, 23 male) ranged in age from 5 to 18 years. 31 children were adopted. Table 1 presents the groups' demographic and clinical characteristics. The pre-intervention CBCL assessment was completed 1-3 days prior to the initial therapy session. The post-intervention CBCL was completed a mean of 43 (SD=34) weeks later. Table 2 presents the pre- and post-test score for Total Problems and the other syndrome scales. FIG. 1 illustrates the medians, ranges, and interquartile values of the pre and post-treatment Total Problems score. The parents of 16 patients also completed more than two CBCL assessments. The improvement trend remained stable over these additional measures.

Of the 41 children in this study, 20 children (49%) were receiving a total of 54 medications at baseline, dropping to 14 after the two day intervention (74% decrease). Of those 20 children on medication, ten permanently discontinued medication (50%). Of the ten who remain on medication (50%), only one is currently receiving more than one medication; this child's regimen includes seizure medications.

A Sample Patient from the Study

A 10-year-old girl was adopted by a single mother. The mother was worried about her ability to care for the child, who was carrying diagnoses of RAD, CD, ODD, LD, and ADHD, after the child fatally stabbed her pet dog in the heart. The child claimed that her intention had been to "hurt" the dog, not to "kill" him. The family intervention included the child, the mother and the maternal grandmother. An attempt was made by the mother on the first day to establish a regulatory bond with her child by reinstating specific components of maternal nurturing. This attempt was not successful and ended with the child running away and hiding for two hours. After the staff and family found the child, intervention between mother and grandmother ended in a successful resolution of conflict and synchronous attunement. On the second day, intervention resumed between mother and child. This resulted in a complete resolution of conflict, with synchronous attunement achieved between mother and child, and again between mother and grandmother. The child's CBCL Total Problems score, which was 136 before the treatment, was measured to be 50 at 12 months and 13 at 24 months. According to both the mother and the referring therapist, the child and her mother have maintained a high degree of attunement and enjoyment of each other's company. The child, who was overweight before treatment, lost 45 pounds subsequently. She is reported to be acting kindly to others and is responsibly caring for the family animals. According to the mother, the child has developed a loyalty to her, and has shown a fine sense of humor not evident before treatment.

TABLE 1

Demographic characteristics of participating children

|  | Males N = 23 | Females N = 18 |
|---|---|---|
| Mean age (SD) | 11.04 (3.27) | 10.83 (3.37) |
| Race/ethnicity |  |  |
| Caucasian, born in USA | 18 | 10 |
| Caucasian, born in Russia | 3 | 1 |
| Biracial-Black/Caucasian American | 4 | 1 |
| Asian | 1 | 1 |
| Hispanic | 0 | 1 |
| Hawaiian American | 0 | 1 |
| Number adopted (%) | 17 (73) | 16 (88.9) |
| Geographical area |  |  |
| Northeast | 6 | 3 |
| Southeast | 3 | 1 |
| Midwest | 10 | 10 |
| West |  |  |

TABLE 2

Mean (SD) CBCL variable scores by Measure

| Variable | Baseline | First Measure | P-Value |
| --- | --- | --- | --- |
| Withdrawn | 5.90 (4.55) | 2.63 (2.97) | 0.003 |
| Somatic | 2.10 (2.59) | 1.15 (1.93) | 0.052 |
| Anxious/depressed | 10.44 (6.40) | 4.93 (4.53) | 0.009 |
| Social problems | 6.37 (3.83) | 2.98 (2.65) | 0.005 |
| Thought problems | 2.37 (3.12) | 1.29 (1.78) | 0.005 |
| Attention problems | 9.34 (5.03) | 4.56 (3.27) | 0.005 |
| Delinquent behavior | 6.78 (4.40) | 2.51 (3.01) | 0.031 |
| Aggressive problems | 19.71 (10.87) | 8.83 (7.04) | 0.001 |
| Sex problems | 41.8 (48.75) | 55.88 (49.36) | 0.561 |
| Number of problems | 48.37 (20.37) | 27.59 (19.21) | 0.423 |
| Total Problems | 72.37 (36.28) | 32.85 (24.27) | 0.001 |
| Internalizing | 17.51 (11.13) | 8.34 (7.86) | 0.002 |
| Externalizing | 26.49 (14.35) | 11.34 (9.62) | 0.005 |

In each figure graph, boxes represent interquartile ranges which contain 50% of values. The whiskers extend from the box to the highest and lowest values, excluding outliers. A line across the box indicates the median.

Figure 13:
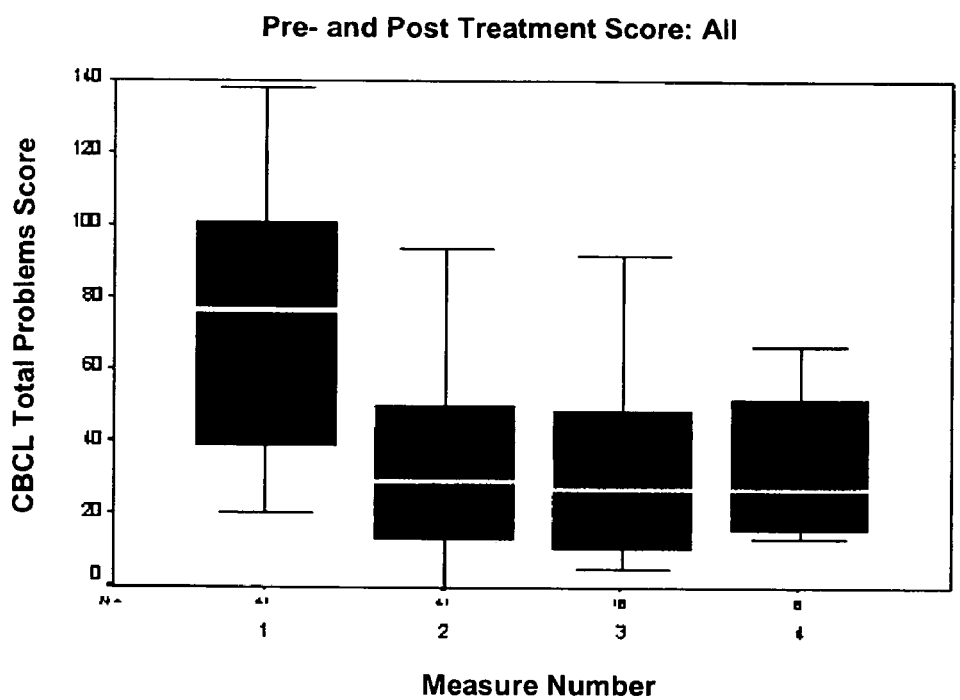
FIG. 13 shows the pre- and post-treatment score for all subjects.
Figure 14:
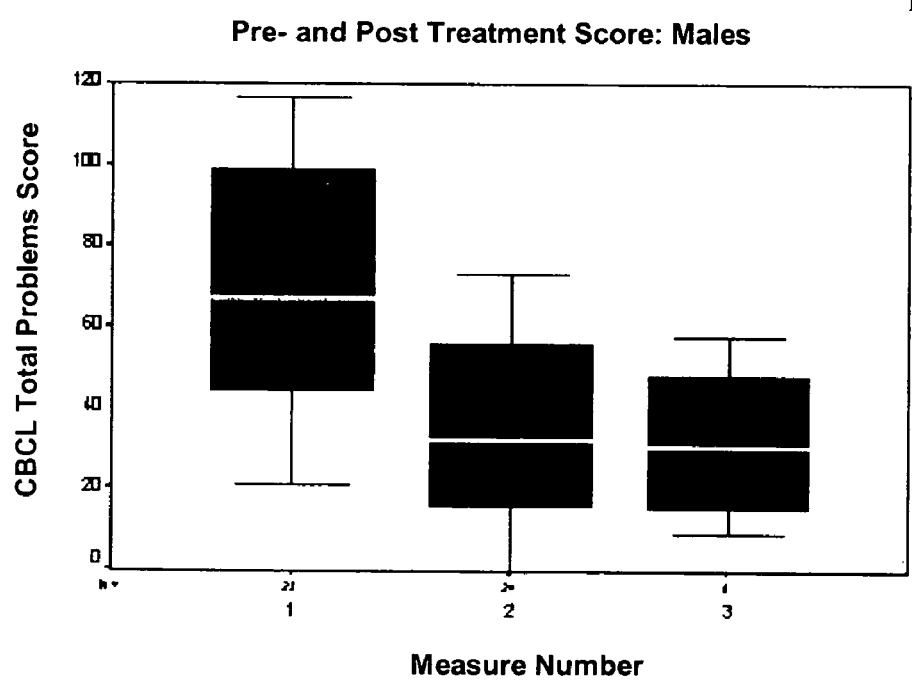
FIG. 14 shows the pre- and post-treatment score for male subjects.
Figure 15:
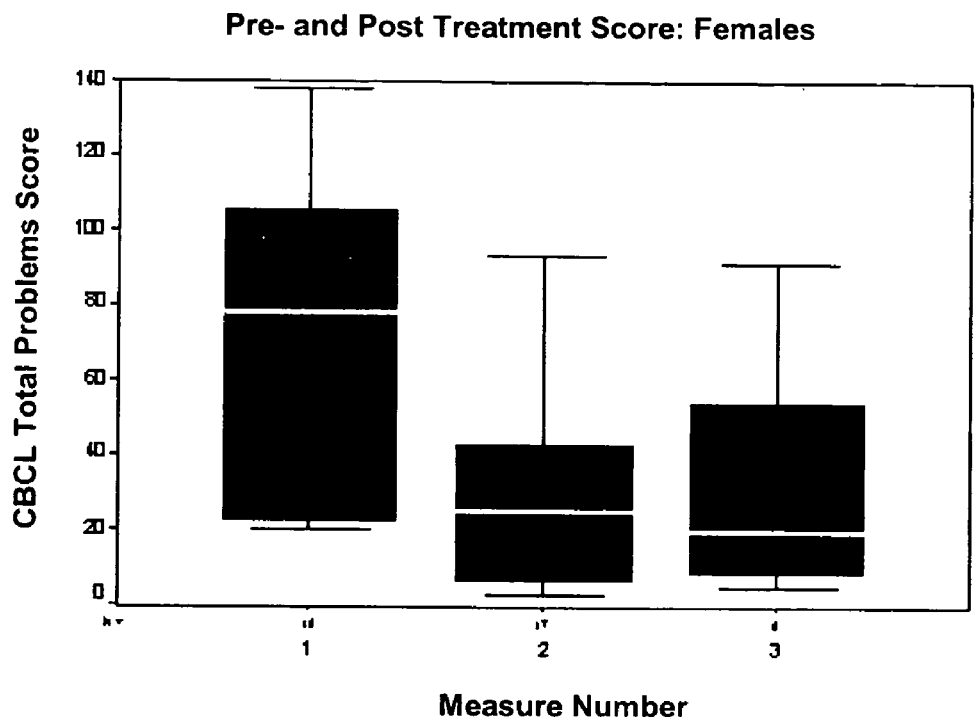
FIG. 15 shows the pre- and post-treatment score for female subjects.
Figure 16:
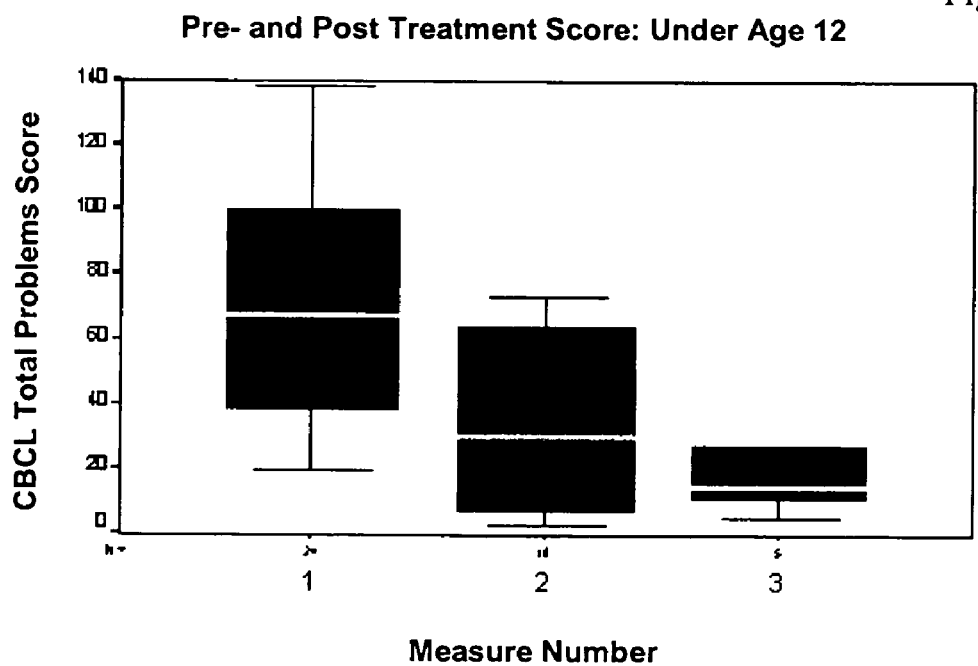
FIG. 16 shows the pre- and post-treatment score for subjects under age 12.
Figure 17:
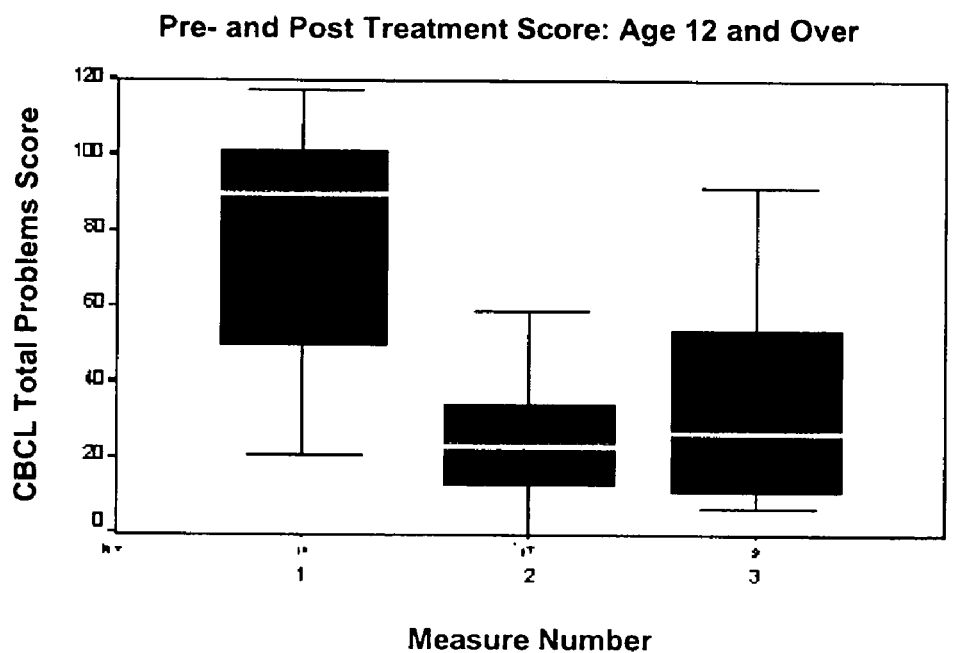
FIG. 17 shows the pre- and post-treatment score for subjects age 12 and above.
Figure 18:
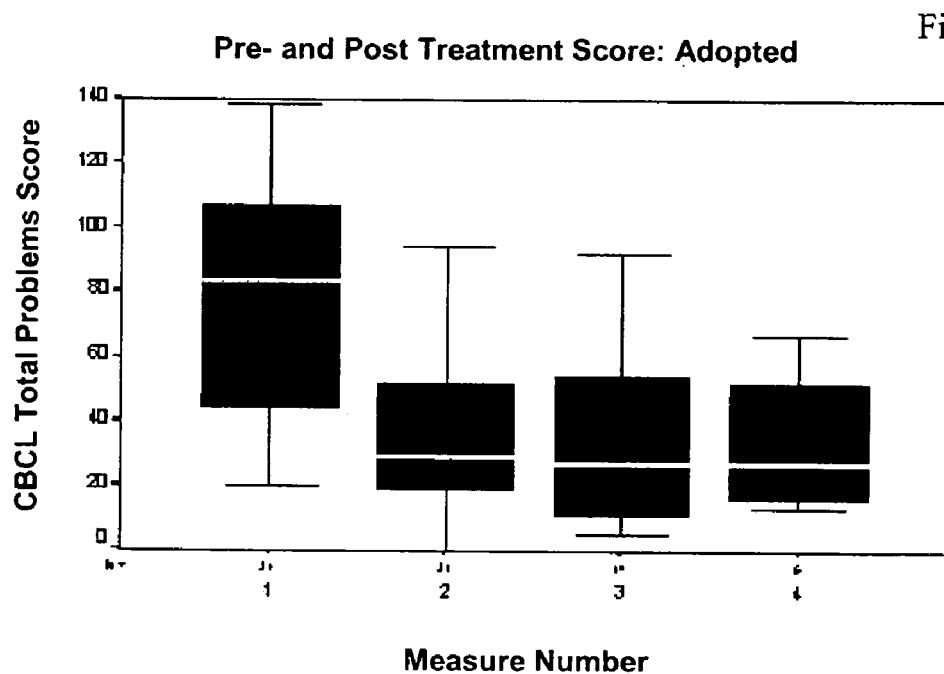
FIG. 18 shows the pre- and post-treatment score for adopted subjects.

The Figures show changes in the Total Problem scale score over time for the study participants: as a whole (FIG. 13), separately for males and females (FIGS. 14 and 15), separately for children younger than age 12 years and ages 12 and above (FIGS. 16 and 17), separately for the adopted group (FIG. 6). The declines in the Total Problem scale scores were statistically significant (p<0.001) in all the groups. The median dropped from about 90 at baseline to less than 30 at the two follow-up assessments among the older children.

This study is the first report of a case series of behaviorally dysregulated children treated with a two-day treatment involving reinstatement of specific components of maternal nurturing. A statistically significant decline in CBCL scores from the clinical to the non-clinical range among behaviorally dysregulated children and adolescents following treatment was observed. The change occurred across a range of CBCL scale scores and was greater than those observed in studies of other non-pharmacological interventions. The intervention appears to have a wider range of effects than pharmacological interventions, and does not appear to have deleterious side effects.

In Somatic Complaints and Sex Problems scale scores, which were not generally in the clinical range prior to treatment, no significant change was observed. The state of calm arousal that results from normal effective maternal nurturing, and that has been shown to be optimal for attentiveness to stimuli and emotional learning, is very similar to the state achieved by the children at the end of the two-day therapy sessions in this study. This therapy teaches both the mother and child the comfort of each other's embrace. This in turn stabilizes and calms the relationship and encourages an emotional climate of openness and receptivity. The calmness that results from the therapy appears to generate and focus the child's energy for information processing and associated memory storage.

Intervention based on reinstatement of specific components of maternal nurturing appears to replicate the survival value of the physiological sequelae of pair bonding, which includes stress modulation. The therapy appears also to facilitate family members' interaction such that recognition and subsequent fulfillment of one another's basic emotional needs are adequately fulfilled.

The patients studied were a non-selected group. The symptom reduction was not associated with race, age group, or gender and persisted over time. Although this study did not select patients, patients were referred to this therapy by other psychiatrists, social workers, and other families. Participants were members of families who could spend a weekend in the initial therapy session, and the therapy required the participation of the entire family.

The subjects described in this paper were only those whose parents completed two or more CBCL's and who gave permission to use the data. Parents who discerned improvement in the child may have been more apt to fill out a second CBCL. Parents with more than one participating child may have been less likely to fill out a CBCL for each individual child than those with single children. The 41 participating children came from 31 families. Parents were also asked to complete a shorter instrument, the Randolph Attachment Disorder Questionnaire, 45 and 52 children with a baseline CBCL and no follow-up CBCL had a preliminary and at least one follow-up RADQ. Though instructed to complete both instruments, parents may have opted to complete the shorter instrument, as opposed to the lengthier CBCL. Some children may require more graded stimulation than a two-day session. These data indicate that reinstatement of specific components of effective maternal nurturing played a causal role in the observed improvement.

Implications for Neuropeptide Therapy

Inasmuch as the symptomatology of behavioral disorders has been found to resolve after a therapy involving mother-child holding, feeding and licking, the results indicate that this treatment shares the mechanisms of action in animal studies of restoration of components of maternal nurturing which measure the reversal of brain deficits caused by maternal separation (Meaney, et al.; Anisman, et al.). These studies, taken together with the inventors' laboratory findings of reversal of gut and brain changes in animals with IBD after peptide therapy (Welch, et al., 2003b), suggest that maternal nurturing, as well as interventions that effectively replicate it, involve ameliorative mechanisms that stimulate neuropeptide release.

Reinstatement of effective maternal nurturing may confer its effects via neurohormonal mechanisms, thus enabling the mother, whether biological or adoptive, to replicate the physiological/emotional modulation that results from normal early maternal nurturing and breast feeding. The profound and sustained changes observed in both the mother and child after restoration of specific components of maternal nurturing indicates that neurohormones were responsible, because 1) the mother's description of feelings of attunement were identical to those reportedly evoked by childbirth, nursing and holding of her infant, and 2) The effects were sustained: Neuropeptides lack the reuptake mechanisms of classical neurotransmitters and thus have long-lasting actions (Kandel). 3) Restoration of specific components of maternal nurturing reverses cognitive and emotional dysfunction, perhaps similar to the way in which it reverses brain deficits secondary to maternal separation in animals. The effects of maternal separation in the animal studies cited above are highly similar to the effects of social isolation in autistic children and maternally deprived orphans.

Accordingly, two candidate neuropeptides that believed to be involved in mother-infant behavior modulation: oxytocin, because of its known actions in maternal-infant bonding; secretin, because it is known to be up-regulated by restraint (Lauterbach), and because maternal-infant holding is suspected to be a type of secure restraint, were selected. Preliminary studies have shown that secretin and oxytocin reverse both visceral inflammation and its concomitant brain activation patterns in both induced rat model colitis and genetic mouse model colitis (Welch et al 2003b). This indicates that the dramatic and long-lasting changes in the patient population treated with an intervention that restores specific components of maternal nurturing has as its underlying mechanism the powerful release of regulatory neuropeptides. This intervention, and/or an intervention that reproduces its effects pharmacologically, can offer an effective therapy to reverse the symptomatology of childhood behavioral disorders.

Example 4

In this experiment, the inventors examined the therapeutic effects of combined peptide therapy in a animal model of Irritable Bowel Syndrome, and determined mechanisms underlining the therapy. Specifically, the inventors tested whether: 1) Secretin is up-regulated in gut/brain axis of colchicine-treated adult rat and in untreated neonatal piglet and rat; and 2) Secretin/oxytocin treatment reverses abnormal brain/gut activity in animal models of inflammatory bowel disease (IBD).

Combined immunocytochemcical techniques (Welch, et al., 2003, 2004) were used to examine gut and cerebral metabolic activity and for neurochemical characterization.

The inventors found that secretin immunoreactivity in the hypothalamus of adult rats was restricted to paraventricular, supraoptic, intercalated hypothalamic nuclei, and ependymal/subependymal cells. Secretinergic neurons were labeled in newborn piglet and rat without colchicine pretreatment. Secretin was present in the neuropil and processes within regions of visceral and emotional processing. Secretin infusion into the fourth ventricle activated comparable brain regions; viscerothalamic and HPA stress axes, amygdala, and ependyma. Central activation and gut inflamation in acquired and genetic IBD models were resolved by secretin/oxytocin peptide infusion.

These results indicate that stress-regulatory neuropeptides condition the brain/gut axis, accounting for their role in behavioral regulation, gastrointestinal function and dysfunction, and potential amelioration of autistic symptoms, which may be linked to visceral dysregulation.

Example 5

In this experiment, the inventors tested whether peptide therapy will resolve cerebral metabolic activity patterns in an animal model of inflammatory bowel disease (IBD), and whether peptide therapy will simultaneously resolve gut/brain dysfunction in an animal model of visceral dysregulation. The inventors discovered that combined secretin/oxytocin therapy resolved colon inflammation in animal models of IBD. Additionally, the inventors discovered that central regions including periventricular grey, reticular core, HPA stress axis-PVN, non-discriminative midline/intralamanar thalamus, and cortical areas including medial pre-frontal (PFC)/Cingulate, insula, orbito-frontal (OF), piriform cortical regions and amygdaloid complex were activated by irritable bowel disease and attenuated by infusion of secretin in combination with oxytocin. These results indicate that visceral stress is processed centrally and that central areas that process visceral stress respond to peptide treatment. These results also indicate that peptide therapy, particularly therapy involving co-administration of secretin and oxytocin, resolves gut inflammation and affected central areas simultaneously. This study demonstrates that multi-neuropeptide therapy may be effectively used to treat many chronic disorders of development including IBD and autism.

Methods

An acquired IBD model was created by inducing Colitis in male Sprague-Dawley rats (n=10) with trinitrobenzene sulfonic acid (TNBS) enema. A genetic IBD model was also created using IL-10 mutant mice. IBD criteria was confirmed in both groups by analyzing numbers of lymphocytes and epithelial destruction, and concomitant cerebral metabolic activity patterns comparing regional induction of c-fos gene expression. Control rats (n=11) and control mice (n=5) were also maintained.

Both the acquired IBD (rat) and genetic IBD (mouse) groups were treated with a combined peptide therapy consisting of co-administration of secretin and oxytocin. The acquired IBD subjects were administered a combination of secretin and oxytocin (40 µg/100 µl i.v.×7-20 days two weeks after disease induction). The genetic IBD subjects were administered a combination of secretin and oxytocin (40 µg/100 µl i.v.×7-20 days at age 18 weeks).

Results

Untreated animals from both genetic and acquired IBD groups showed marked inflammation of the colon. Inflammation of the colon was significantly reduced in treated animals. There was partial resolution of colon inflammation after treatment with secretin alone in the mutant mice. There was a marked resolution in both rat and mouse with combined secretin and oxytocin therapy. Further, central regions activated by IBD and attenuated by secretin/oxytocin infusion therapy include: periventricular grey, reticular core, HPA stress axis-PVN, non-discriminative midline/intralamanar thalamus, and cortical areas including medial pre-frontal (PFC)/Cingulate, insula, orbito-frontal (OF), piriform cortical regions and amygdaloid complex.

These data indicate that visceral stress is a potent dysregulator of cognitive and emotional brain regions/brain states, and that visceral stress and cognitive/emotional distress are inseparable. The data also show that peptide therapy, particularly therapy utilizing co-administration of secretin and oxytocin, provides a simultaneous resolution of gut and brain disorders. Gut and brain areas affected in this study overlap those affected in autism, including: thalamus amygdale, HF, Cingulate orbital frontal insula, and PFC. Accordingly, peptide therapy may be used to effectively treat autism, autistic spectrum disorders and a wide range of other dysregulated behaviors.

Example 6

In this experiment, the inventors investigate whether peptide therapy will resolve cerebral metabolic activity patterns in an animal model of primary biliary cirrhosis and whether peptide therapy will simultaneously resolve gut/brain dysfunction in an animal model of visceral dysregulation. Combined secretin/oxytocin therapy should resolve bile duct distress in animal models of primary biliary cirrhosis. Central regions activated by primary biliary cirrhosis should also be attenuated by infusion of secretin in combination with oxytocin. These results indicate that visceral stress is processed centrally and that central areas that process visceral stress respond to peptide treatment. These results also indicate that peptide therapy, particularly therapy involving co-administration of secretin and oxytocin, resolves visceral stress and affected central areas simultaneously. This study will demonstrate that multi-neuropeptide therapy may be effectively used to treat a range of autoimmune disorders including primary biliary cirrhosis.

Methods

An animal model of primary biliary cirrhosis is created by using Sprague-Dawley rats. Primary biliary cirrhosis criteria was confirmed in both groups by analyzing numbers of lymphocytes and epithelial destruction, and concomitant cerebral metabolic activity patterns comparing regional induction of c-fos gene expression. Control rats are also maintained.

The rats are treated with a combined peptide therapy consisting of co-administration of secretin and oxytocin. The subjects are administered a combination of secretin and oxytocin (40 µg/100 µl i.v.×7-20 days two weeks after disease induction).

Results

It is expected that untreated animals will show marked bile duct distress and that bile duct distress will be significantly reduced in treated animals. Further, central regions activated by primary biliary cirrhosis will overlap with those attenuated by secretin/oxytocin infusion therapy.

These data indicate that visceral stress is a potent dysregulator of cognitive and emotional brain regions/brain states, and that visceral stress and cognitive/emotional distress are inseparable. The data also show that peptide therapy, particularly therapy utilizing co-administration of secretin and oxytocin, provides a simultaneous resolution of visceral and brain disorders. Accordingly, peptide therapy may be used to effectively treat a wide range of autoimmune disorders.

Example 7

In the following study, the inventors examined brain effects of gastrointestinal inflammation in a rat model of acquired inflammatory bowel disease (IBD) and in a genetic mouse model of IBD with the goal of: (1) comparing brain areas affected by IBD with brain areas known to be abnormal in autism; (2) testing whether the inflammatory changes in the gut are resolved by combined (S/OT) peptide treatment; and (3) determining whether systemic peptide treatment will resolve cerebral metabolic activity patterns in animal models of visceral inflammation. The inventors discovered that brain regions activated by IBD and attenuated by S/OT infusion included the HPA/visceral thalamic stress axes and cortical domains, and septal/preoptic/amygdale. Hematoxylin/eosin-stained gut section in controls showed marked inflammation, while S/OT-treated animals had dramatically reduced infiltrates. The inventors concluded that visceral inflammation and concomitant activation of brain areas often abnormal in autism may be resolved simultaneously through neuropeptide therapy.

Methods

Data were obtained in 21 adult male Sprague-Dawley rats weighing 250-450 g and in 14 C57B6 IL-10-/- mice. Rats were obtained from Hilltop Lab Animals, Inc. (Scottdale, Pa.) and housed at the New York State Psychiatric Institute Housing Facility. Mice were obtained from Jackson Laboratory (Bar Harbor, Me.) and housed at the Eye Institute Annex of Columbia University.

Sprague-Dawley rats (n=10) were anesthetized with ketamine and xylazine and administered a solution of trinitrobenzene sulfonic acid (TNBS). 0.5 ml of TNBS solution (100 µl TNBS 5% solution; 150 µl PBS; 250 µl 100% ethanol) per day×5 days was administered intrarectally (Dohi T, et al., '00). Control rats (n=11) were injected with phosphate buffered saline (PBS) solution alone. On days 0, 3 and 7, the TNBS enema was administered via a glass microsyringe equipped with a gastric intubation needle. The animals were treated at the following time intervals: 3-4 days after the TNBS treatment in the Sprague-Dawley rats and at 18 weeks of age in the IL-10-/- mice.

Animals were anesthetized with xylazine (7-10 mg/kg I.P.) and ketamine (60 mg/kg I.P.) prior to implantation of an Alzet pump (model #2002). To implant the pump used to deliver the peptides vs. saline vehicle control, a surgical incision was made in the peritoneum of an anesthetized animal. Bacitracin was employed as a topical antiseptic jelly. Wounds were sutured, anesthesia was discontinued and animals were returned to individual cages for care and observation during the post-operative period. The peptide or saline contents of the implanted pump were delivered either I.V. or I.P. in rat or mouse, respectively. The pump was installed in both experimental and control animals to assess possible long-term effects of acute tissue injury on basal expression levels of the c-fos gene product, though such effects were not expected.

Peptide treatments or control vehicle were infused via Alzet pump over a period of 7-20 days (endpoint) in the following doses:

| Oxytocin | Secretin | OT/S | VIP | OT/VIP | S/AVP |
| --- | --- | --- | --- | --- | --- |
| VIP 40 µg/100 ml. saline × 7 days or 100 µg/ 250 µl saline × 20 days | 40 µg/100 ml.saline × 7 days or 100 µg/250 µl saline × 20 d. | 40 µg each peptide/100 ml.saline × 7 d or 100 µg OT and 100 µg S/250 µl saline × 20 d | 100 µg/ 250 µl saline | 100 µg OT and 100 µg VIP per 250 µl saline | 100 µg S and 100 µg AVP per 250 µl saline |

KEY:
Oxytocin (OT)
Secretin (S)
Vasoactive intestinal peptide (VIP)
Vasopressin (AVP)

Animals were euthanized at the treatment end point by rapid intraperitoneal injection of xylazine and ketamine, followed by transcardial perfusion, sequentially with physiological heparinized saline and a 4% solution of paraformaldehyde in sodium phosphate buffer, pH 7.4. Whole brains were removed and blocked. The forebrain was blocked from the frontal pole to the mesodiencephalic junction. Identical procedures were followed in control and experimental animals.

Tissue blocks were post-fixed for 2-3 h in individual glass vials containing 4% paraformaldehyde in 0.1 M PBS (pH 7.4) and cryoprotected overnight at 4° C. in a solution of 10% sucrose in 0.1 M PBS. Frozen sections were cut on a sliding microtome at 30 µm in the transverse plane and every fourth section was processed immunocytochemically for c-fos protein. Tissues from control and experimental animals were processed simultaneously in the same solutions in order to control for potential variability in immunocytochemistry. All incubations were carried out in separate test wells on a Thomas rotator table. Tissues were collected in 0.1 M PBS (pH 7.4) in spot test wells and washed in Tris-buffered saline (TBS) between each of the steps.

Non-specific binding sites were blocked by pre-incubating for 30 min in 1% bovine serum albumin (BSA), diluted 1:30 in TBS. Thereafter, tissue sections were incubated overnight at Room temperature in primary rabbit anti-Fos protein diluted 1:10,000 (Oncogene, Cambridge, Mass.) in TBS containing 0.1% BSA, to which 0.25% Triton X-100 was added to facilitate antibody penetration. Sections were washed in TBS for 10 minutes×3 in biotinylated goat anti-rabbit IgG secondary antibody (1:200) for one hour. The sections were then washed for 10 minutes×3 and incubated for 45 minutes in avidin-biotin peroxidase complex (1:100) (Vector Labs, ABC Elite Kit) and subjected to standard chromagen reaction. In 21 Sprague-Dawley rats and 14 IL-10−/− mice, topographic distribution and density patterns of immunocytochemically labeled neurons were mapped, qualitatively, by light microscopy. Brain activity patterns were evaluated by computerized imaging of experimental and control animals. Gene induction patterns were demonstrated in regions where constitutive expression of encoded phosphoprotein is low or absent under resting conditions, or in response to control deposits of vehicle.

Inflammation of intestinal mucosae was identified in experimental animals by histological analysis postmortem via staining with hematoxylin/eosin staining. Portions of the terminal ileum and colon were removed, blocked, sectioned histologically and examined for fibroid plaques and granulocyte infiltrates. Both gut and brain sections were examined using light microscopy; digital images were obtained with a SPOT-RT slider Diagnostic Instruments camera mounted on a Nikon Microphot microscope.

Results

Gut inflammation & regional brain activation patterns were comparable in genetic and acquired models of IBD. In both mouse and rat models, animals experiencing visceral inflammation displayed comparable IBD-related cerebral activity patterns. Case studies revealed consistent and clear-cut differences between distribution and density patterns of immunoreactive cells in treated animals and those in untreated animals. Systemic administration of combined Secretin and Oxytocin (S/OT) was effective in resolving regional gut inflammation and regional cerebral metabolic response.

Figure 19:
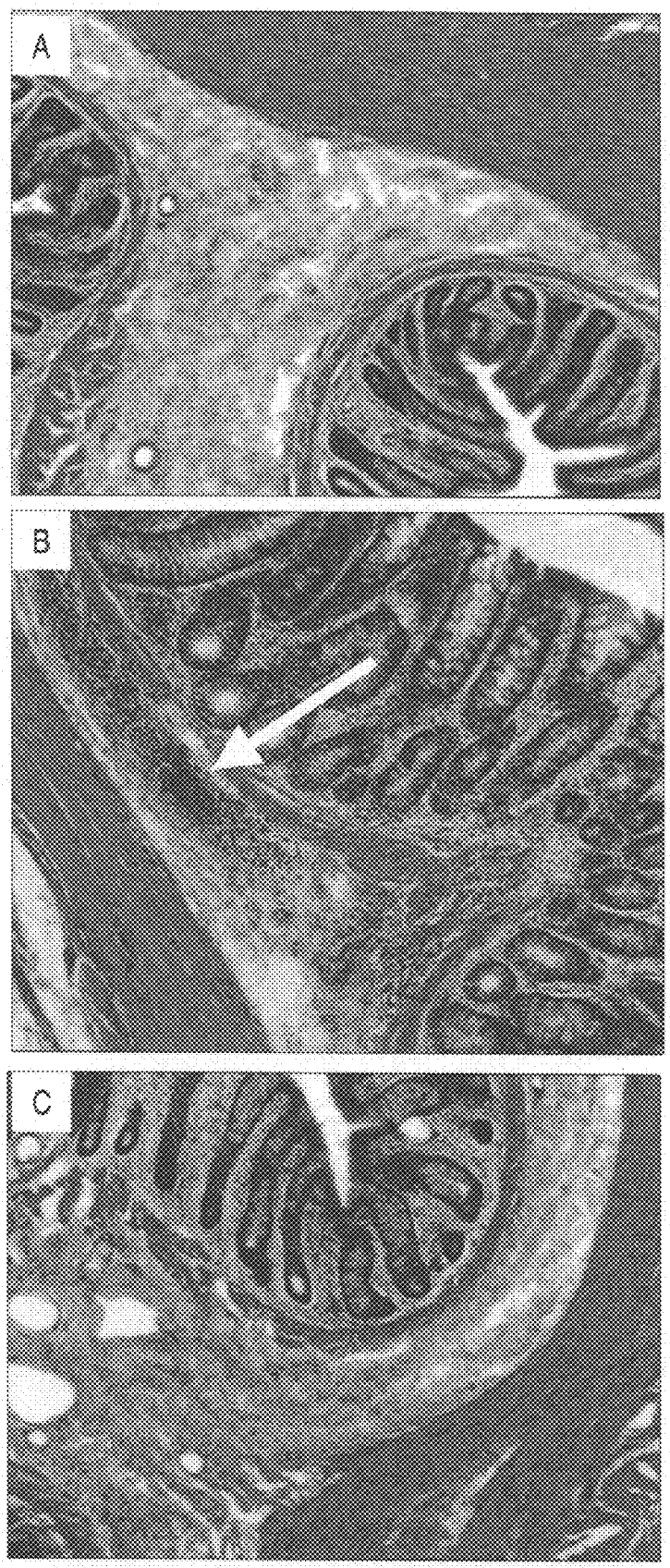
FIG. 19 depicts photomicrographs of hematoxylin and eosin stained colon in the TNBS-induced IBD model (A) shows normal colon in control rat (No IBD saline treated); (B) shows TNBS-induced colitis in colon of IBD untreated rat. The arrow indicates inflammatory infiltrate; (C) shows colon of a TNBS-induced inflammatory bowel disease (colitis) rat treated with systemic infusions of Secretin/Oxytocin peptides (40 μg each peptide/100 ml. I.V. in 7 days or 100 μg/250 ml. in 20 days) delivered over a 7-20 day period. Colitis was induced by a standard procedure of TNBS induction and a 10-day post-induction time period. Note the dramatic increase in inflammatory infiltrate in B (arrow) and resolution in C of inflammation after treatment with 7-20 days of I.V. infusion with Secretin/Oxytocin peptides. Findings are representative data obtained in 21 rats.

Dramatic inflammatory infiltrates were observed in the colon of an experimental (colitis) rat. In untreated TNBS-induced IBD, hematoxylin & eosin-stained gut sections showed marked inflammation characterized by neutrophilic infiltration into the colonic mucosa and submucosa, and associated thickening of the colon wall. Peptide-treated animals had dramatically reduced infiltrates with restoration of the histologic appearance of the mucosal and submucosal layers. The TNBS-induced infiltrates in the IBD colon were resolved by I.V. infusion of S/OT. Administration of S/OT improved histologic scores, which dropped from 4 to 0-1 (range 0-5). (See FIG. 19.)

Figure 22:
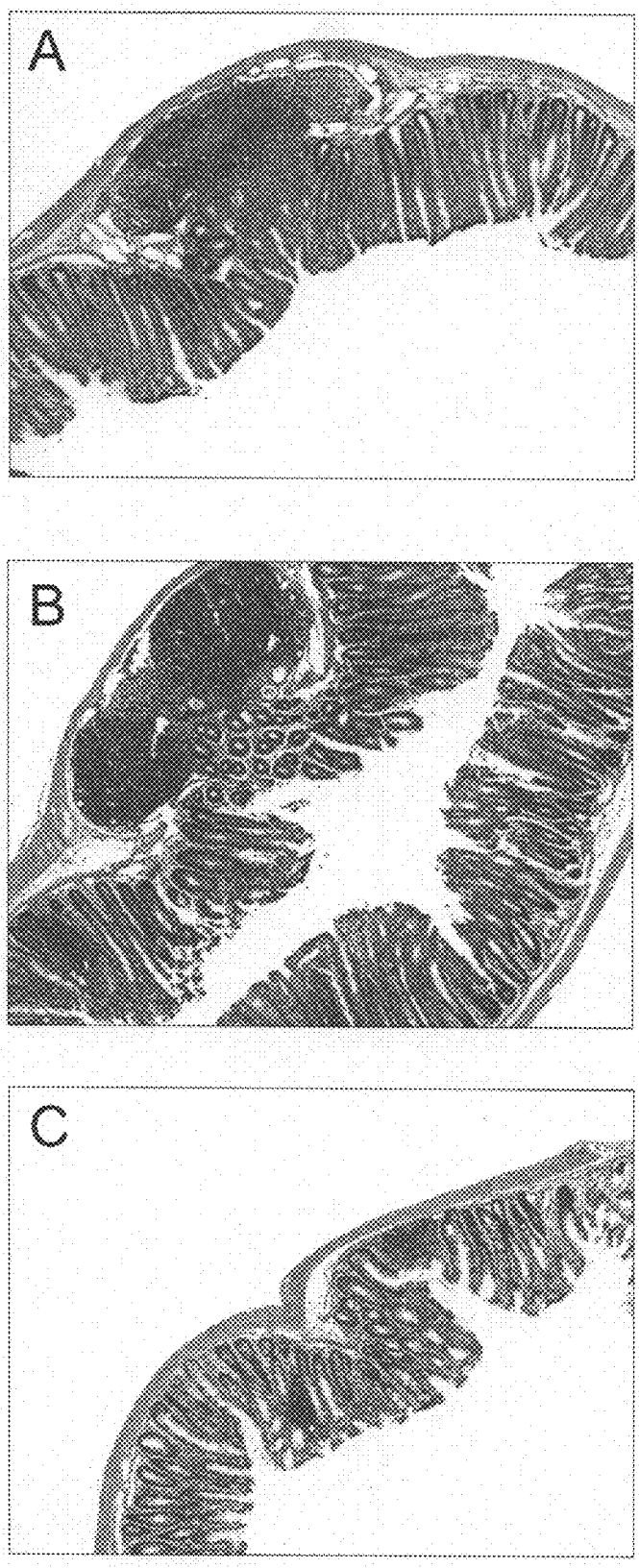
FIG. 22 shows photomicrographs demonstrating colitis in a genetic IL10 mutant mouse colitis model of IBD. (Hematoxylin and eosin stain). (A) Saline treated IL10−/− colon; (B) Colon of IL10−/− after treatment with systemic (I.P.) infusions of Secretin only; (C) Colon of IL10−/− after treatment with systemic (I.P.) infusions of Secretin/Oxytocin peptides (40 μg each peptide/100 ml) delivered by Alzet pump over a 7-day period. Note the dramatic increase in inflammatory infiltrate in (A) in the saline treated animal and (B) in the Secretin (only) treated mouse and resolution of inflammation in (C) after peptide treatment. Findings are representative data obtained in 14 IL10−/− mice. Colitis-induced changes in regional cerebral metabolism localized to structures that are sensitive to stress and to S infusion by I.V. or I.C.V. (Welch et al 2003 Cell and Mol Neurobiol Vol. 23 #5/6). Concomitant cerebral metabolic activity patterns were compared by examining the regional distribution of c-fos gene protein expression. Representative data are illustrated in Example 6 below.

Mouse: In the IL 10 knockout mouse model, there was also neutrophilic infiltration into the colonic mucosa and submucosa associated with thickening of the colon wall, as well as ulcerations and loss of cells. There was a partial resolution of inflammation in the IL10−/− mouse after I.P. infusion of S and an almost complete resolution of inflammation with combined S/OT peptide therapy. The few remaining lesions in S/OT treated IL10−/− mice were markedly smaller than those in animals treated either with saline or with secretin alone. The restoration of the mucosa and submucosa after dual peptide treatment was similar to that in the rat; the mouse model's histologic scores dropped from 4 to 1. Neighboring regions of colon examined in the S/OT treated mice were free of infiltrates. (See FIG. 22).

Regulatory regions attenuated by S/OT treatment were comparable in acquired and genetic models. Comparisons were made between c-fos expression by neurons in rats and mice with symptoms of IBD and animals treated with the S/OT preparation. Atlases of the rat brain by Swanson (Swanson (2003) Brain Maps: Structure of the Rat Brain, Second Edition, Elsevier, Amsterdam) and by Paxinos and Watson (Paxinos, et al., The Rat Brain in Stereotaxic Coordinates, Academic Press, San Diego), an atlas of the mouse brain by Sidman (Sidman, et al. (1971) Atlas of the Mouse Brain and Spinal Cord, Harvard University Press, Cambridge), and the inventors' previous mapping studies of dopamine cell systems in different mouse strains (Baker, et al., Variations in number of dopamine neurons and tyrosine hydroxylase activity in hypothalamus of two mouse strains, *J. Neurosci.*, 1983 3(4):832-43) were used as guides for identifying nuclear boundaries in the rodent brain.

Figure 25:
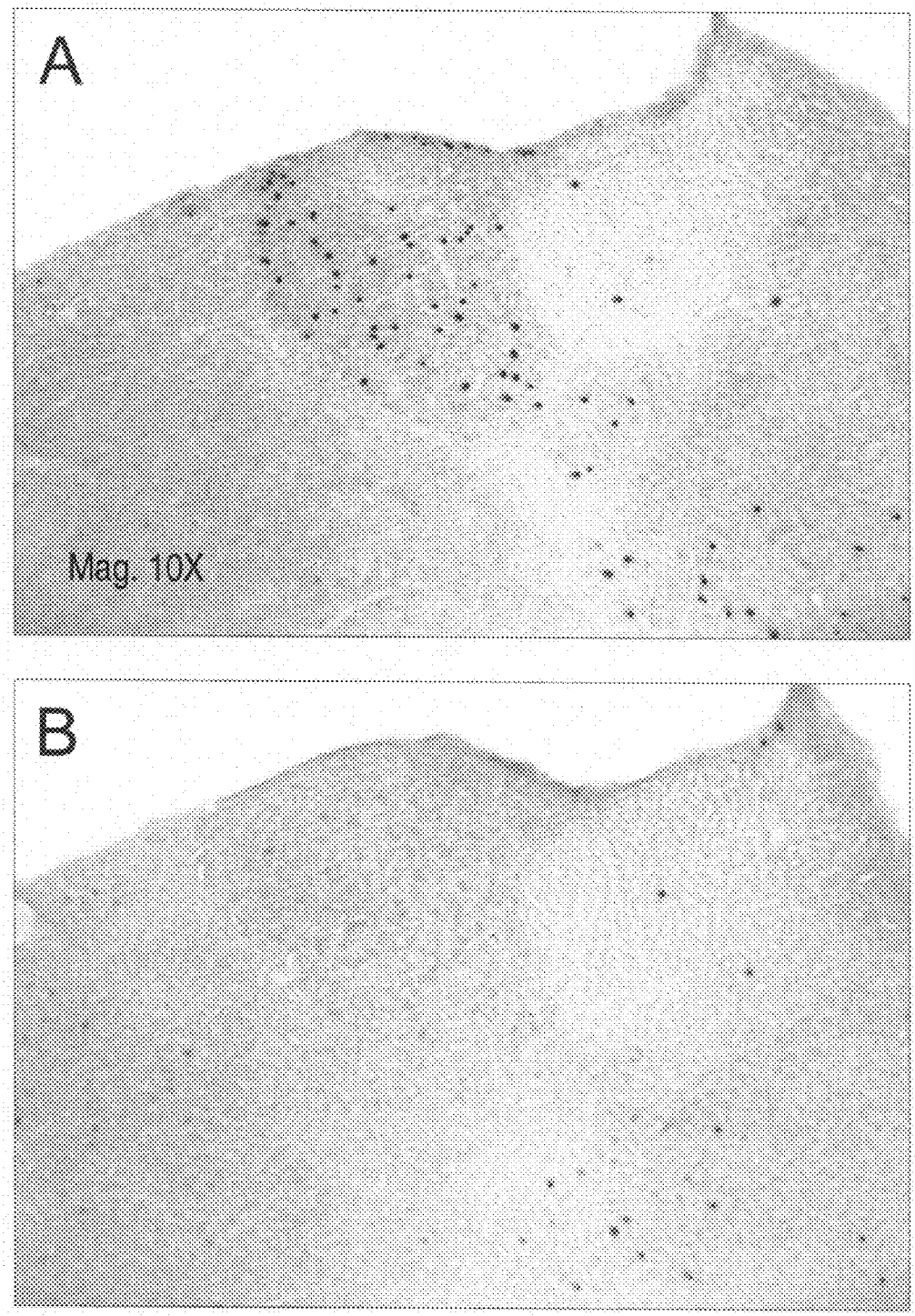
FIG. 25 depicts photomicrographs of Fos immunostained sections of the IL10−/− mouse Habenula, a dopaminergic region involved in learning, conditioning and sensitization. (A) The habenula of IL10−/− mouse treated by physiological saline infusions. Note colitis-induced stress reaction of the habenula monitored by dramatic c-fos gene expression; (B) Habenula of IL10−/− mouse treated with Secretin/Oxytocin. Note the dramatic decrease in habenular reactivity in an animal with resolution of IL10−/− colitis after I.P. infusion with Secretin/Oxytocin peptide therapy.

The epithalamus demonstrated clear-cut IBD-related activation. High concentrations of immunoreactive cells were observed in the lateral habenular nucleus of saline-treated rodents, as well as those with untreated IBD. In contrast, most of the medial division was devoid of nuclear immunoreactivity. Forebrain regions attenuated by S/OT infusion included the epithalamus, the habenula, and its projection fields. (See FIG. 25.)

Figure 26:
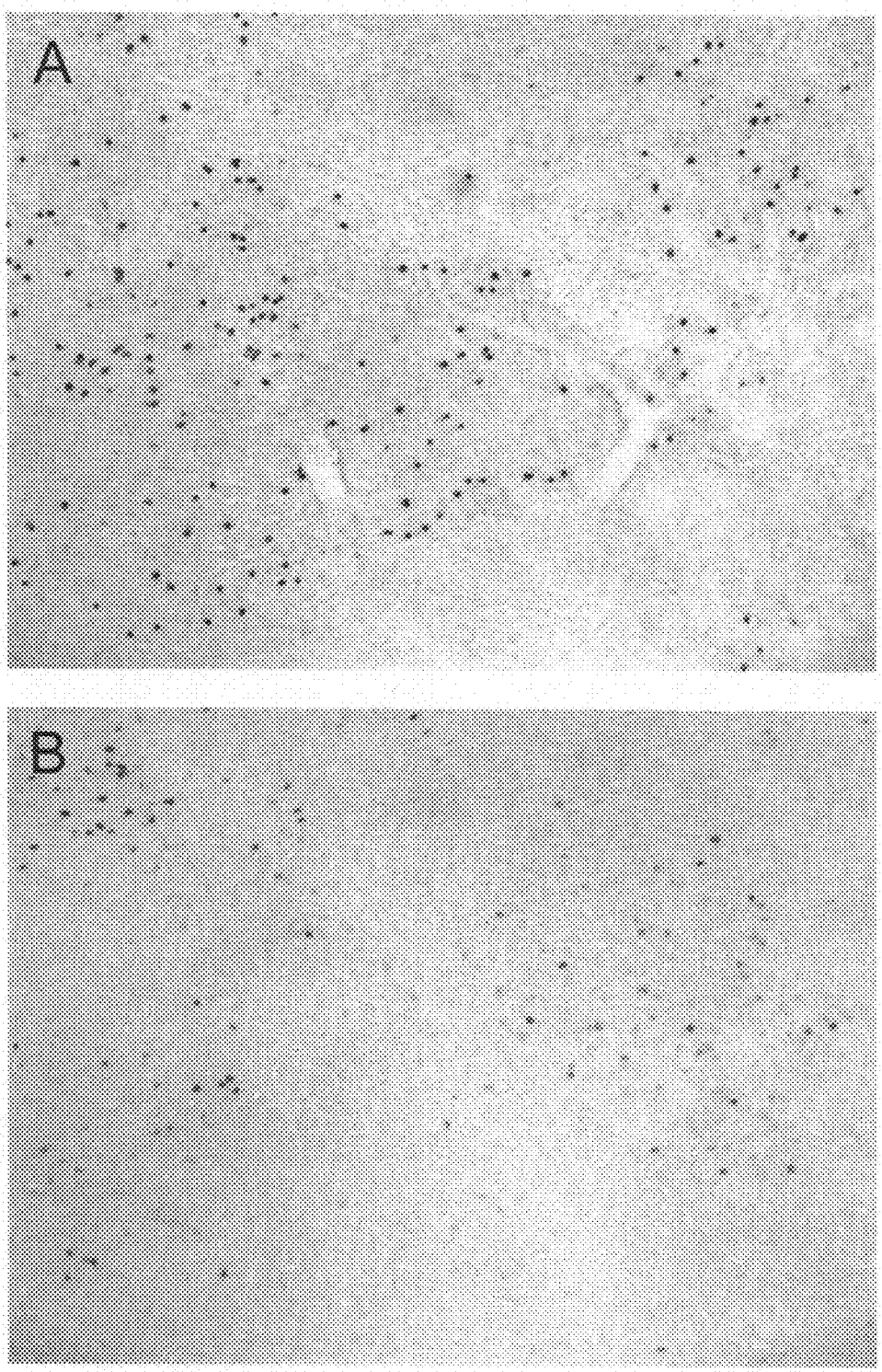
FIG. 26 shows photomicrographs of Fos immunostained sections of the IL10−/− mouse intralamanar thalamus. The intralamanar thalamus perceptually encodes state of internal milieu. It is reciprocally connected with PFC to modulate behavioral reactivity and motivate goal-directed behavior in response to homeostatic challenge. (A) The thalamus of IL10−/− mouse treated by physiological saline infusions. Note colitis-induced stress reaction of the intralamanar thalamus monitored by high concentrations of cells expressing Fos-like immunoreactivity; (B) Intralamanar thalamus of a Secretin/Oxytocin treated IL10−/− mouse. Note the dramatic decrease in thalamic reactivity in an animal with resolution of IL10−/− colitis after I.P. Secretin/Oxytocin peptide infusion.
Figure 27:
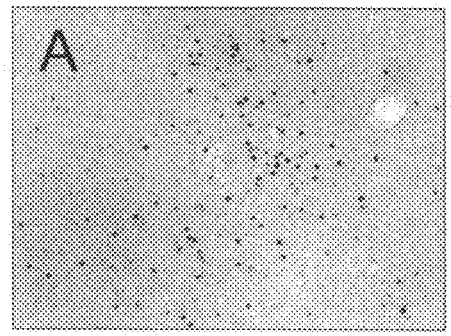
FIG. 27 shows photomicrographs of Fos immunostained sections of TNBS-induced IBD rat comparing 20-day saline treatment vs. systemic VIP/OT treatment (A) depicts the central amygdale (10×)—IBD Untreated rat; (B) shows the central amygdala (10×)—IBD VIP & oxytocin treated rat; (C) depicts the somatosensory area (4×)—IBD untreated rat; (D) depicts the somatosensory area (4×)—IBD VIP and oxytocin treated rat; (E) shows the paraventricular hypothalamus (10×)—IBD untreated rat; and (F) shows the paraventricular hypothalamus (10×)—IBD VIP and oxytocin treated rat. Note the robust activation in the saline treated IBD rats and the attenuation in the S/OT treated TNBS-induced IBD animals.
Figure 27:
Figure 27:
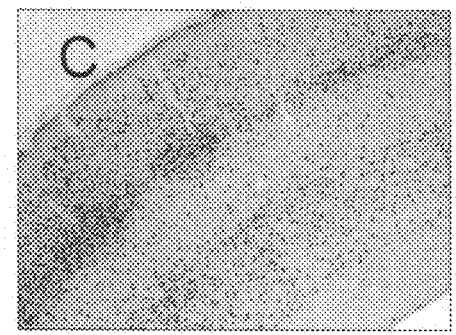
Figure 27:
Figure 27:
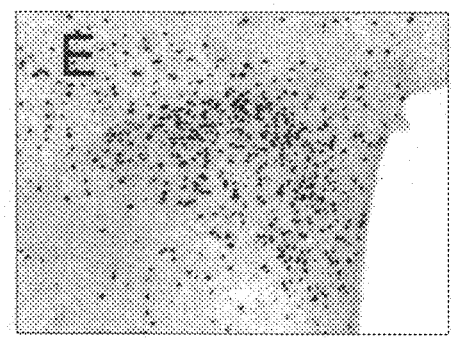
Figure 27:
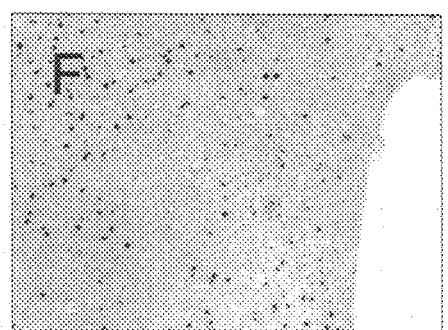

In the thalamus, the midline intralamanar complex demonstrated robust activity, principally of the stress-sensitive paraventricular visceral thalamic nucleus. The intermediodorsal thalamus and paracentral nucleus of the thalamus were also very heavily labeled in saline-treated and IBD rodents. By contrast, dorsal, medial and ventral tier and reticular shell compartments were not activated in IBD or saline-treated animals. After treatment, the midline intralamanar complex consistently showed attenuation (See FIG. 26), whereas the anterior nucleus of the paraventricular thalamus retained levels of immunoreaction product comparable to those in controls. The posterior compartment showed attenuation, a predictable finding given evidence of early stress reactivity in this region.

Figure 21:
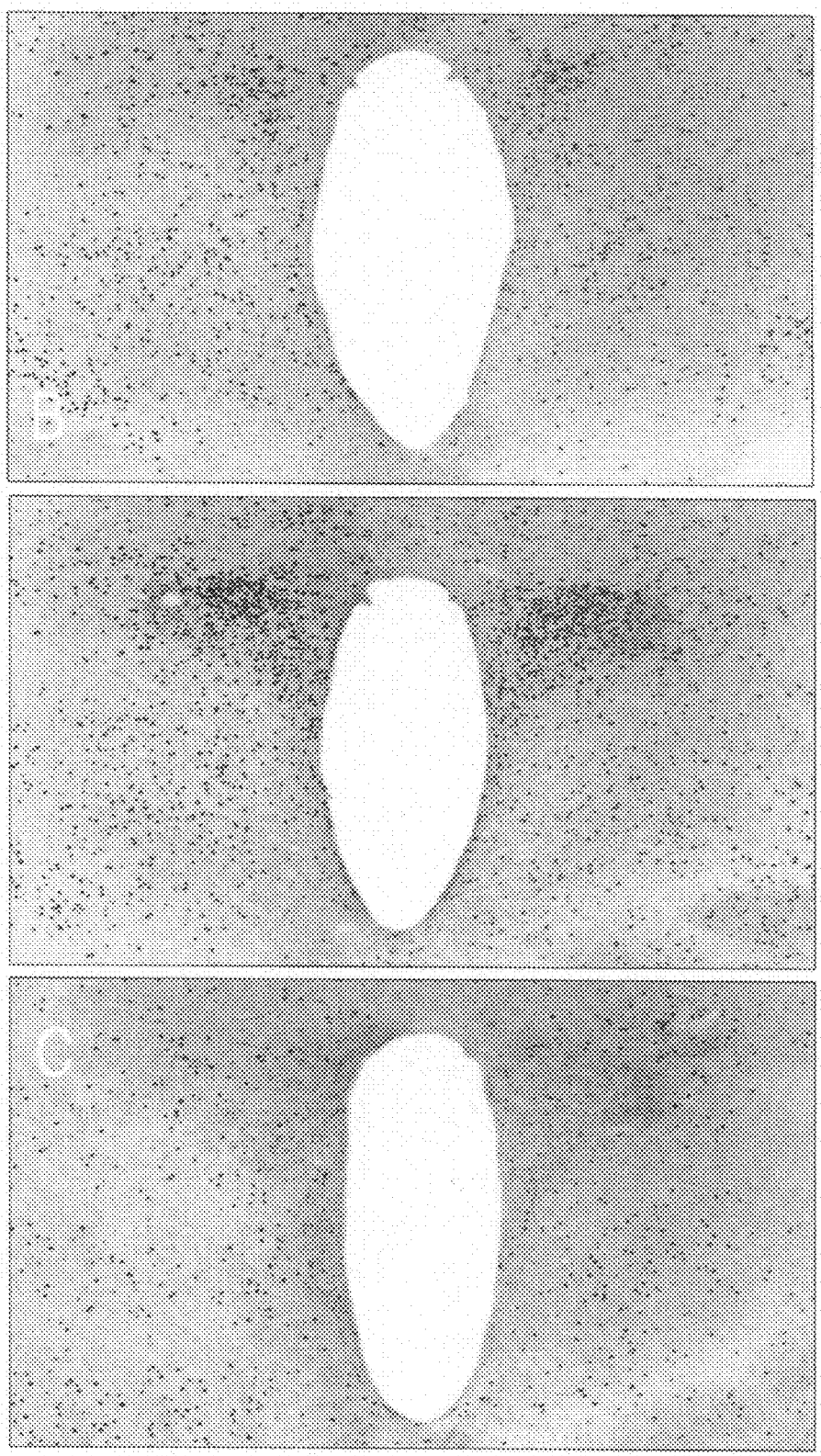
FIG. 21 shows photomicrograph of Fos immunostained sections of the rat paraventricular hypothalamus (PVN). The hypothalamus controls homeostatic balance. (A) Note the PVN of control rat administered physiological saline infusions in lieu of TNBS. The control animals were treated with saline I.V. infusions in lieu of peptide therapy; (B) TNBS-induced colitis. Note colitis-induced stress reaction of PVN demonstrated by c-fos gene expression; (C) Note the dramatic decrease in PVN reactivity in an animal with resolution of TNBS-induced colitis after I.V. infusion with Secretin/Oxytocin peptide therapy.

In the preoptic hypothalamic nuclear continuum, IBD activation patterns were restricted to specific hypothalamic nuclear regions: IBD untreated and saline-treated rats and mice demonstrated functional activation of specific lateral and medial hypothalamic cell columns. The paraventricular hypothalamic nucleus contained high concentrations of immunolabeled cells localized to anterior, medial and lateral parvicellular subnuclei. (See FIG. 21). Cerebral activation patterns in IBD untreated and saline-treated rodents encompassed regions defined by the aforementioned neurochemical mapping studies of dopamine cell systems in different rodent strains.

Figure 28:
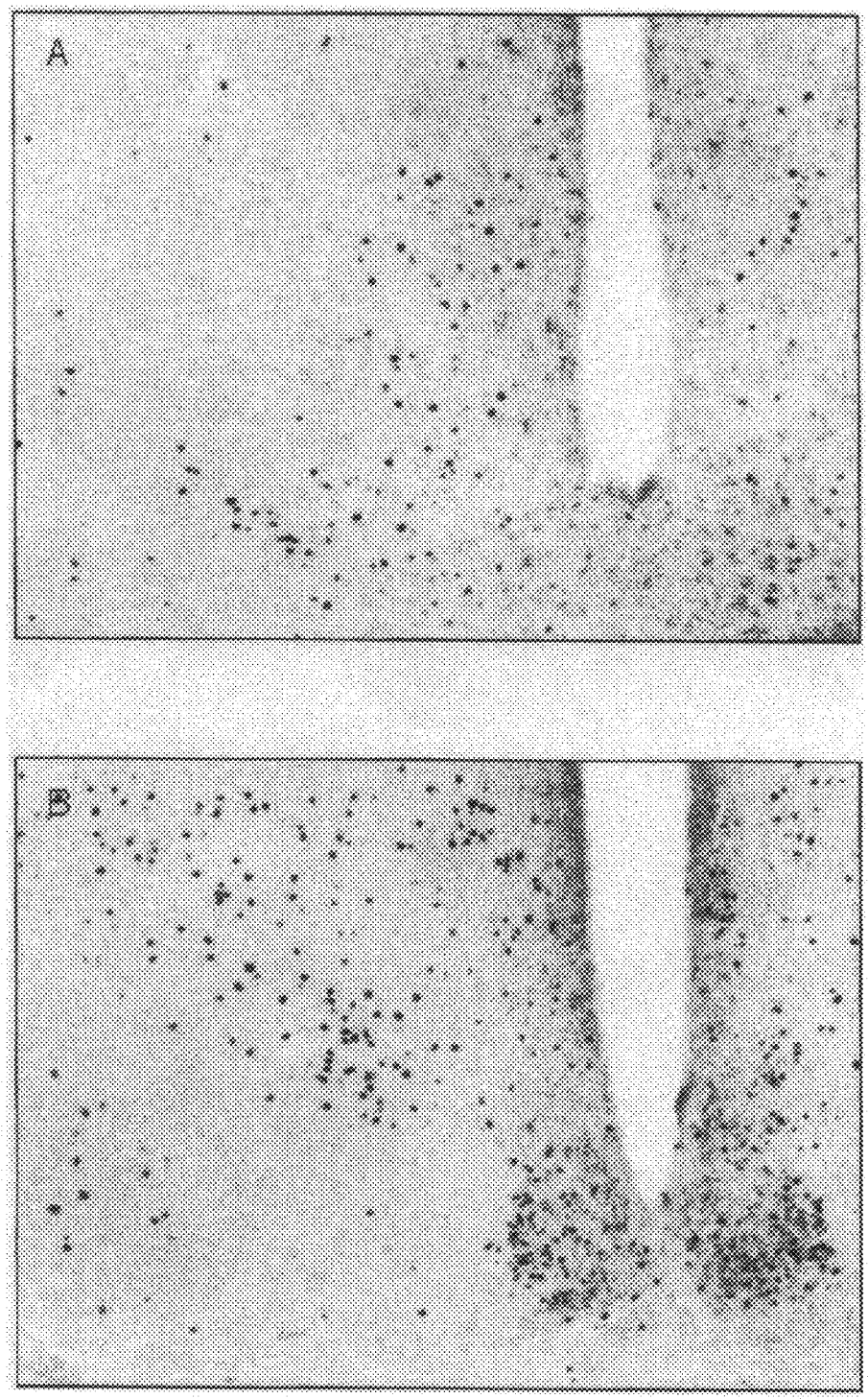
FIG. 28 shows photomicrograph of Fos immunostained section of the IL10−/− mouse hypothalamus. (A) Note the reaction pattern in the colitis-induced stress model monitored by the absence of c-fos gene expression of Fos-like immunoreactivity in the preoptic suprachiasmatic region of an IL 10−/−mouse treated with physiologic saline infusions; (B) Note the robust activation patterns of this region after a systemic infusion of Secretin/Oxytocin peptide combination.

After dual-peptide treatment, the previously mentioned areas of the hypothalamus activated by IBD were attenuated, and the preoptic area was robustly activated. The preoptic suprachiasmatic region, zona inserta, and tuberal nucleus were activated in treated animals (see FIG. 28).

Medial prefrontal, cingular and lateral insular/orbitofrontal cortical areas disclosed activation of layers II & III in saline-treated and IBD untreated animals. The piriform cortex demonstrated the most profound reaction to IBD, which activated neurons concentrated in granular layer II. The secondary motor area was circumscribed by high concentrations of immunoreactive cells, contrasting with the absence of labeling in the primary motor cortex. Other areas showed no consistent cerebral metabolic response patterns.

Figure 24:
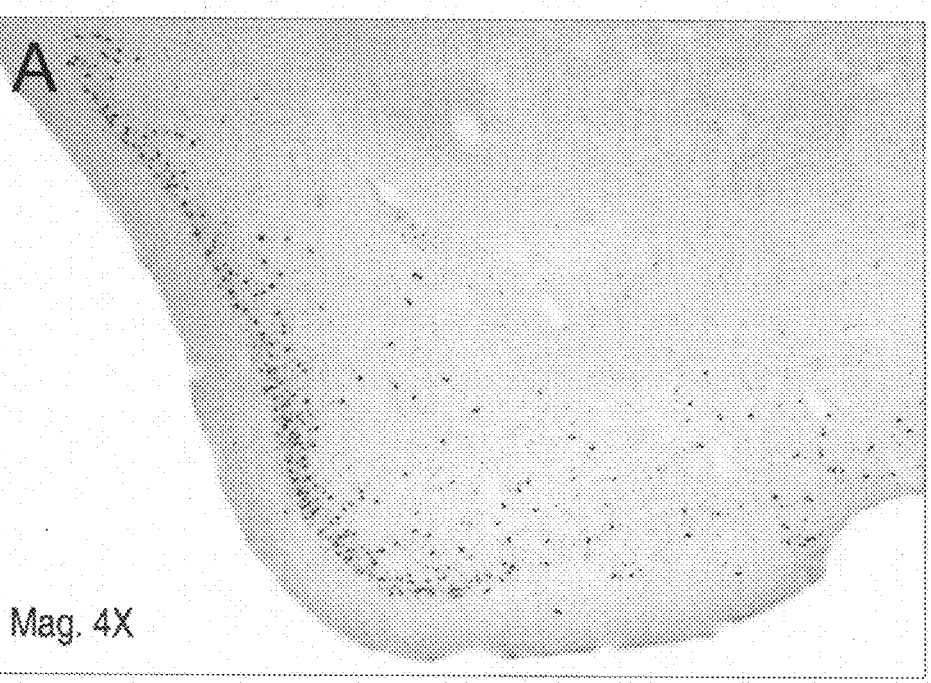
FIG. 24 shows photomicrographs of Fos immunostained sections of the IL10−/− mouse piriform cortex. The piriform cortex is involved in early environmental conditioning. (A) The piriform cortex of IL10−/− mouse treated by physiological saline infusions in lieu of peptide therapy. Note colitis-induced stress reaction of the piriform cortex monitored by dramatic c-fos gene expression of Fos-like immunoreactivity in layer II; (B) A treated IL10−/− colon Note the dramatic decrease in piriform reactivity in an animal with resolution of IL10−/− colitis after I.P. infusion with Secretin/Oxytocin peptide therapy.
Figure 24:

In cortical regions of treated animals, the most striking attenuation was found in the piriform cortex, granular layer II. (See FIG. 24). The secondary motor area was also attenuated, as judged by a consistent lack of immunoreaction product.

Figure 20:
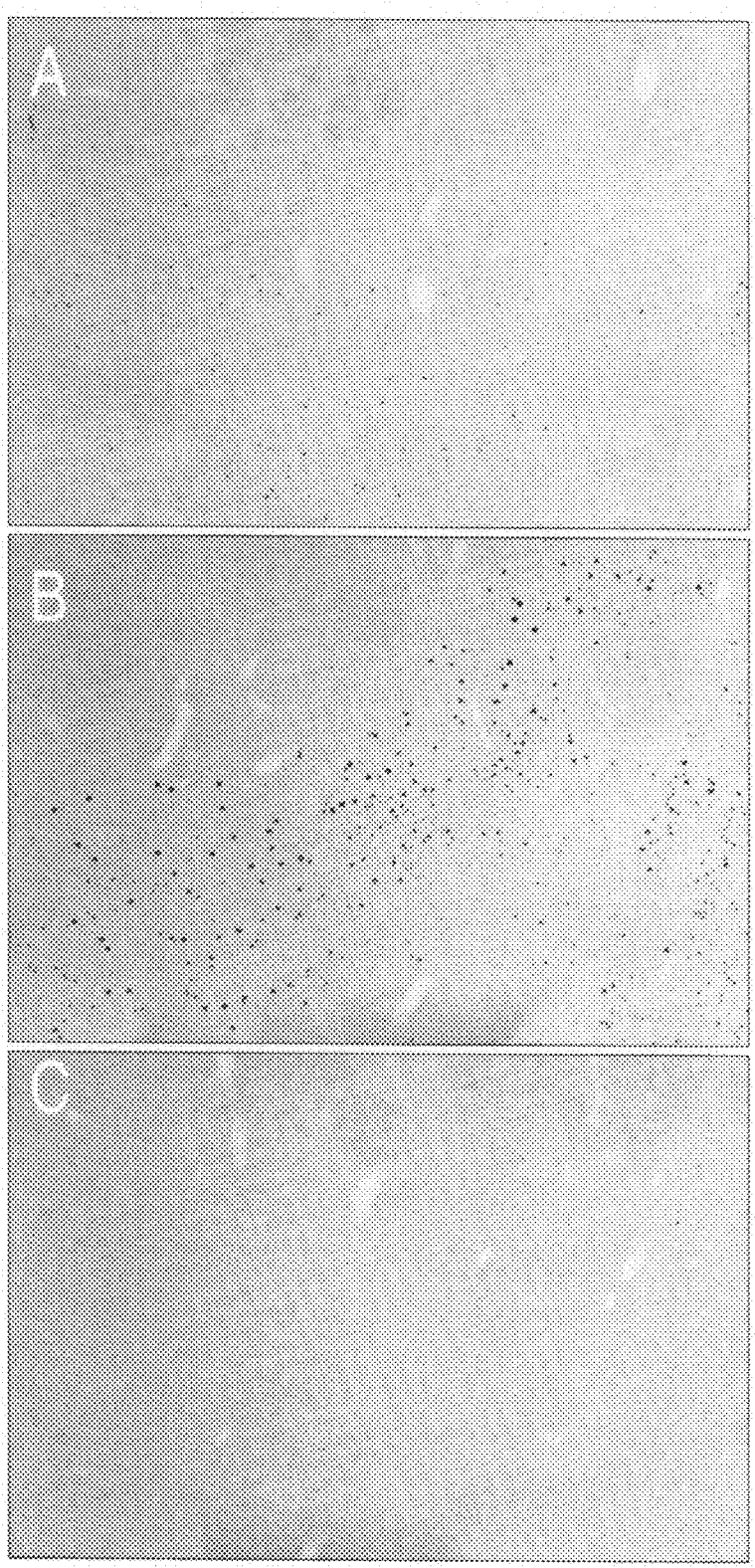
FIG. 20 shows Photomicrographs of Fos immunostained sections of the rat central amygdala. (A) Note the central amygdaloidal nucleus of a control rat given physiological saline enemas in lieu of TNBS. The figure shows the anxiogenic center-implicated in adverse conditioning of pre-cognitive, cognitive, reflexive and peripheral organ response patterns; (B) TNBS-induced colitis. Note colitis-induced stress reaction of amygdala monitored by dramatic c-fos gene expression of Fos-like immunoreactivity concentrated in the central amygdaloidal nucleus; (C) Note the dramatic decrease in amygdalar reactivity in an animal with resolution of TNBS induced colitis after treatment with 7-20 days of I.V. infusion with Secretin/Oxytocin peptide therapy.
Figure 23:
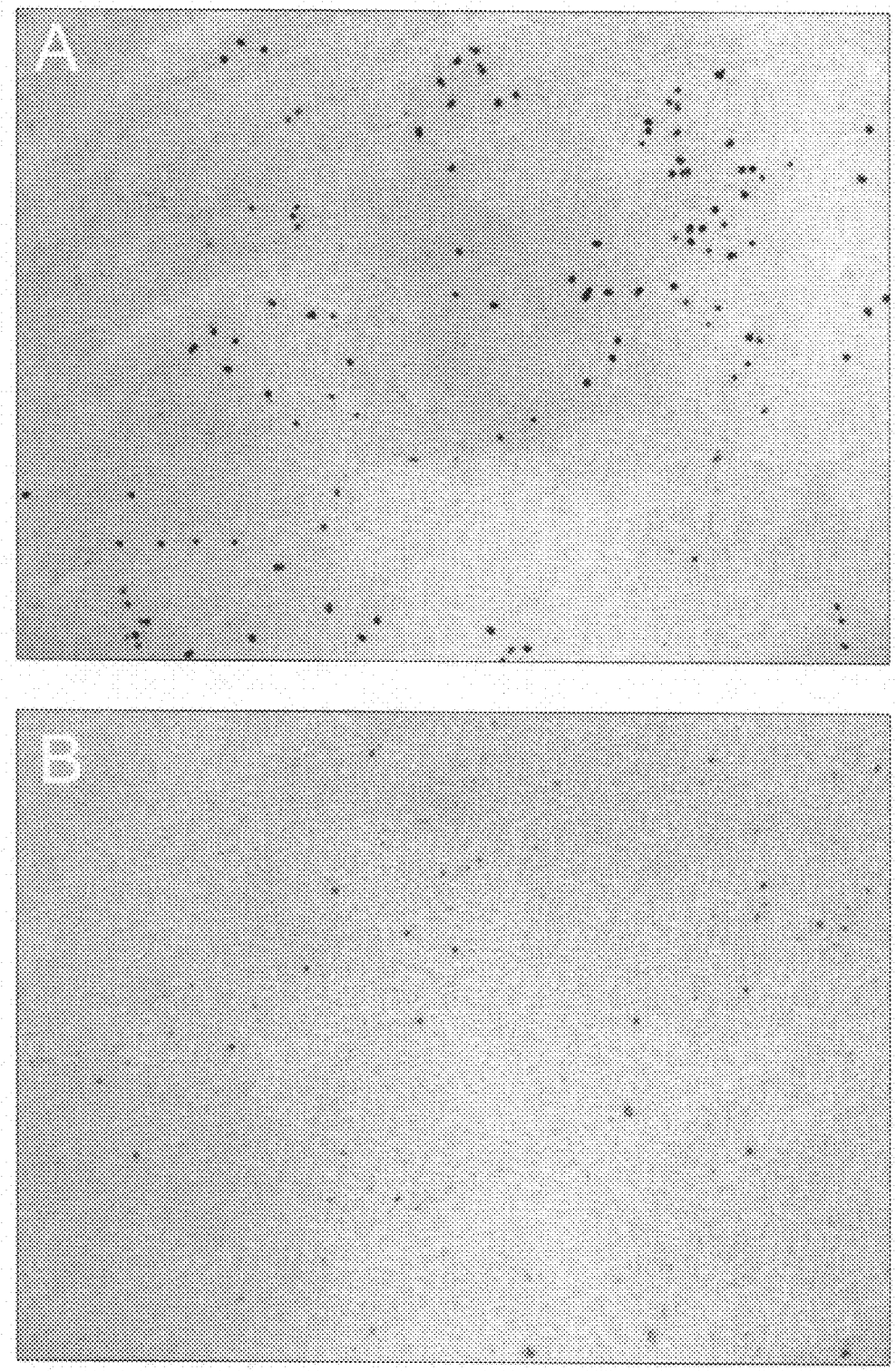
FIG. 23 shows photomicrographs of Fos immunostained sections of the IL10−/− mouse central amygdala. The central amygdala is the site of pathology in autism and is important in social recognition and early environmental conditioning. (A) Note the central amygdaloid nucleus of an IL10−/− mouse treated by physiological saline infusions. Note colitis-induced stress reaction of amygdala monitored by dramatic c-fos gene expression of Fos-like immunoreactivity concentrated in the central amygdaloid nucleus; (B) An IL10−/− colitis mouse treated with Secretin/Oxytocin peptide therapy. Note the dramatic decrease in amygdalar reactivity in an animal with resolution of IL10−/− colitis after treatment with 7 days of I.P. infusion of peptides.

The most striking subcortical IBD activation patterns were localized to the central amygdaloid nucleus and contiguous regions of the ventral and lateral striatum. By contrast, cortical, medial and basolateral amygdaloid nuclei were quiescent. After peptide treatment, the striatum and central amygdaloid nuclei of both the TNBS-colitis rat and IL10−/− mouse contained little immunoreactivity (See FIGS. 20 and 23). By comparison, striking activation of cortical, medial and basolateral amygdala and dentate gyrus of the hippocampal formation was observed, contrasting with the quiescence of those regions in saline-treated and untreated animals with IBD.

Other members of the S and OT families were also used in combination: vasopressin/secretin and VIP/OT. VIP/OT resulted in similar alterations in gut and brain to S/OT. A major difference between S/OT and VIP/OT was the latter's effect on the thalamus. The thalamic stress activation by IBD is characterized by diffuse activation of the midline intralamanar complex and contiguous regions of the mediodorsal thalamus. This pattern was reversed by VIP/OT infusion that resolved into selective activation of midline thalamic structures only whereas S/OT had more diffuse effects. This difference supports the inventors' hypothesis that more than two peptides may prove to be the superior combination.

Counts of neurons expressing Fos were obtained for control and experimental animals and were categorized according to treatment group. Comparisons of neurons expressing Fos in IBD saline placebo control and peptide treated animals were made.

In order to standardize sampling, counts of neurons were taken from a total of 6 sections each separated by 90 μm. Representative structures in mouse and rat were analyzed for quantitative analysis. Data were analyzed for statistical significance using non-parametric tests. The level of statistical significance was established at $p<0.001$ for all comparisons. Qualitative analyses demonstrated clear-cut and replicable differences in the aforementioned structures. In representative regions of animals with IBD neurons expressing Fos-like immunoreactivity were distributed topographically and far outnumbered those observed in peptide treated animals. The presence of Fos-like immunoreactivity in the IBD group was an index of regional brain response to chronic visceral inflammation. In regions which were devoid of Fos protein in IBD, the density of Fos protein was marked in peptide-treated animals. Table 1 shows statistical comparisons of the numbers of neurons expressing Fos in the piriform cortex and amygdala in animals with IBD and with IBD treated by systemic peptide infusions.

This study is the first demonstration of the relationship between IBD and regional brain activation in two models of visceral inflammation: a genetic and an acquired model of colitis. The results indicate that brain areas of visceral representation respond when the gut is inflamed. The results also show for the first time that secretin (S) and oxytocin (OT), when delivered in combination (S/OT), can ameliorate both visceral and central manifestations of two forms of inflammation, since the visceral inflammation in the model systems examined here arises from two distinct etiologies. Our findings, if confirmed, could have powerful therapeutic implications for a variety of inflammatory conditions.

Representations of visceral disturbance were visualized through the immunocytochemical detection of the c-fos gene product in characterizing inflammation-related changes to the brain in these two rodent models.

Central regions that were activated by IBD and attenuated by S/OT infusion selectively mapped to visceral/emotional areas. The most striking activation patterns were localized to pre-cognitive or emotional limbic areas, including medial pre-frontal/cingulate, insular, orbito-frontal and piriform cortex, amygdala, and midline visceral thalamus. HPA stress axis components were activated, including the paraventricular nucleus of the hypothalamus. Especially striking in both rat and IL10−/− mouse models were colitis-induced changes in regional cerebral metabolic activity of the habenula, the intralamanar thalamic complex, and the central amygdaloid nucleus and piriform cortex. IBD-related activation, and concomitant attenuation with resolution of IBD after peptide administration, mapped to brain centers subserving both pro- and reactive organized behaviors that are linked anatomically and modulated neurohumorally.

Brain structures involved in visceral processing are presumably activated by IBD-induced changes to the colon. Both the gut inflammation and corresponding central activation patterns are resolved by the dual peptide treatment. It is possible that peripheral and central areas are resolved separately by S/OT infusion. However, it is more likely that altered brain activation patterns resolve, once inflammation has been attenuated. After treatment, central regions of visceral processing are no longer receiving abnormal signals from the periphery. The basic mechanisms underlying the changes observed in gut and brain likely involve peptidergic actions on cellular components of the immune system. This hypothesis merits further investigation.

These models provide insight into the neurologic manifestations of inflammatory disorders. A systematic analysis of brain regions activated by chronic visceral inflammation appears to implicate structures regulating organized behavioral, endocrine and autonomic functions. Cortical thalamic structures activated in this study by both acquired and genetic colitis are involved in the perceptual encoding of visceral stress, as well as in adaptation to chronic unremitting stress. (Sica, et al., Chronic-intermittent hypoxia induces immediate early gene expression in the midline thalamus and epithalamus, *Brain Res.* (2000) 883(2): 224-8; Welch, et al., Secretin activates visceral brain regions in the rat including areas abnormal in autism, *Cell. Mol. Neurobiol.* (2003) (4-5): 817-37.) Chronic stress-related information generated by colitis is processed via neural and humoral modes of communication. Memory of dysregulated states, such as visceral inflammation, is encoded as unremitting stress. Stress adversely conditions the entire gut/brain network.

The fact that the S/OT peptide combination attenuated thalamic activation secondary to IBD suggests that a stress-regulatory mechanism was activated as a result of this study's intervention. The attenuation of the thalamus by VIP/OT was slightly different from the S/OT effect. The IBD activation pattern reversed by VIP/OT infusion resolved into selective activation of midline thalamic structures only, whereas S/OT had more diffuse effects. This difference supports the hypothesis that more than two peptides together may provide a superior treatment.

The fact that a peptide combination deactivated the robust colitis-induced c-fos response in the amygdala, the brain's anxiogenic center, suggests that a combined peptide treatment may have implications for a variety of psychiatric and developmental disorders. Under conditions of unremitting stress, the amygdala is implicated in adverse conditioning of cognitive, pre-cognitive, reflexive and peripheral organ response patterns.

C-fos activation by the peptide treatment is as important as attenuation and may shed light on the underlying mechanisms of the intervention. Certain regulatory areas including cortical, medial and basolateral amygdala, dentate gyrus of hippocampal formation and pre-optic areas of hypothalamus, which were not activated prior to treatment, were robustly immunolabeled by dual S/OT peptide treatment. We hypothesize that these areas had been, in fact, de-activated by IBD. These findings support the theory that peptide therapy is contributing to reestablishment of homeostasis.

Both psychiatric and physical illnesses are known to both cause stress and to be exacerbated by stressors. (Sidman, et al. (1971), Atlas of the Mouse Brain and Spinal Cord., Harvard University Press, Cambridge; Baker, et al., Variations in number of dopamine neurons and tyrosine hydroxylase activity in hypothalamus of two mouse strains, *J. Neurosci.* (1983) 3(4): 832-43; Sica, et al., Chronic-intermittent hypoxia induces immediate early gene expression in the midline thalamus and epithalamus, *Brain Res.* (2000) 883(2):224-8.) Isolation stress may exacerbate both IBD and autistic spectrum disorders (Sica, et al., Chronic-intermittent hypoxia induces immediate early gene expression in the midline thalamus and epithalamus, *Brain Res.* (2000) 883(2): 224-8) and dysregulate humoral and cellular immunity. (Sica, et al., Chronic-intermittent hypoxia induces immediate early gene expression in the midline thalamus and epithalamus, *Brain Res.* (2000) 883(2): 224-8; Welch, et al., Secretin activates visceral brain regions in the rat including areas abnormal in autism, *Cell. Mol. Neurobiol.* (2003) 23(4-5): 817-37). It is also known to cause hippocampal formation deficits (Palecek, et al., The dorsal column pathway facilitates visceromotor responses to colorectal distention after colon inflammation in rats, *Pain* (2003) 104(3):501-7; Drossman, et al., Alterations of brain activity associated with resolution of emotional distress and pain in a case of severe irritable bowel syndrome, *Gastroenterology* (2003) 124(3):754-61; Yaniv, et al., A gradient of plasticity in the amygdala revealed by cortical and subcortical stimulation, in vivo, *Neuroscience* (2001)106(3): 613-20) and gut abnormalities. (Saitoh, et al., Cross-sectional area of the posterior hippocampus in autistic patients with cerebellar and corpus callosum abnormalities, *Neurology* (1995) 45(2): 317-24; Lightdale, et al., Gastrointestinal symptoms in autistic children, *Clin. Perspec. Gastroenterol.*, 156-58 (2001); White, Intestinal pathophysiology in autism, *Exp. Biol. Med.* (Maywood) (2003) 228(6):639-49; Uvnas-Moberg, Oxytocin linked antistress effects—the relaxation and growth response; *Acta. Physiol. Scand. Suppl.* (1997) 640:38-42.) Such dysregulation may be resolved by possible anti-stress effects of peptide administration. (Luna, et al., Neocortical system abnormalities in autism: an fMRI study of spatial working memory, *Neurology* (2002) 24; 59(6):834-40.)

Gut and brain areas affected in this study overlap those affected in autism: gastrointestinal tract, amygdala, cingulate, hippocampal formation, pre-frontal and orbito-frontal cortex. (Baron-Cohen, et al., Social intelligence in the normal and autistic brain: an fMRI study, *Eur. J. Neurosci.* (1999) 11(6): 1891-8; Haznedar, et al., 2000, Limbic circuitry in patients with autism spectrum disorders studied with positron emission tomography and magnetic resonance imaging, *Am. J. Psychiatry*, 157(12):1994-2001; Levitt, et al., Proton magnetic resonance spectroscopic imaging of the brain in childhood autism, *Biol. Psychiatry* (2003) 54(12): 1355-66; Cook, Autism: review of neurochemical investigation, *Synapse* (1990) 6(3):292-308.) Though preliminary, the strength of this data suggest that gut inflammation could be linked to several types of dysregulation present in many autistic patients, such as hyperserotonemia (Chugani, et al., Altered serotonin synthesis in the dentatothalamocortical pathway in autistic boys, *Ann. Neurol.* (1997) 42(4):666-9), altered levels of brain serotonin (Linthorst, et al., Brain neurotransmission during peripheral inflammation, *Ann. N.Y. Acad. Sci.* (1998) 840:139-52; Porter, et al., Unique salience of maternal breast odors for newborn infants, *Neurosci. Biobehav. Rev.* (1999) 23(3):439-49), and a variety of sickness behaviors, such as behavioral inhibition/isolation (Porter, Olfaction and human kin recognition, *Genetica* (1998-99)104(3):259-63; Anisman, et al., Cytokines, stress and depressive illness: brain-immune interactions, *Ann. Med.* (2003) 35(1):2-11), mood lability (Dantzer, Cytokine-induced sickness behavior: mechanisms and implications, *Ann. N.Y. Acad. Sci.* (2001) 933:222-34; Penny, et al., Relationship between trace elements, sugar consumption, and taste in Crohn's disease, *Gut* (1983) 24(4):288 -92) and carbohydrate food preferences (Gershon, et al., Personal communication 2003).

More generally, autistic symptoms and other behavioral disorders may result from a dysregulation of the gut/brain axis that is conditioned by peptide/peptide and peptide/neurotransmitter interactions. One study, for instance, found an 80% decrease in serotonin/secretin co-localization in the guts of two autistic children. (Nelson, et al., Neuropeptides and neurotrophins in neonatal blood of children with autism or mental retardation, *Ann. Neurol.* (2001) 49(5): 597-606.) If peptides are, in fact, dysregulated in autism (Gershon, et al., Personal communication 2003; Welch, et al., Secretin: hypothalamic distribution and hypothesized neuroregulatory role in autism, *Cell. Mol. Neurobiol.* (2004) 24(2): 167-89), then these findings suggest that central, as well as peripheral networks, and peptide/transmitter interactions with norepinephrine, dopamine, angiotensin and 5HT, could be dysregulated, as well. (Walker, et al., (1999) Properties of secretin receptor internalization differ from those of the beta(2)-adrenergic receptor, *J. Biol. Chem.* 274(44):31515-23.)

Another interaction with relevance to gastrointestinal disorders is the relationship between angiotensin II AT (1) and S receptors, which are co-localized in endocytic vesicles. (Armando, et al., (2001) Peripheral administration of an angiotensin II AT(1) receptor antagonist decreases the hypothalamic-pituitary-adrenal response to isolation stress, *Endocrinology*, 142(9):3880-9.) Antagonizing angiotensin II AT(1), which is hyper-driven by social isolation stress (Bregonzio, et al., (2003) Anti-inflammatory effects of angiotensin II ATI receptor antagonism prevent stress-induced gastric injury, *Am. J. Physiol. Gastrointest. Liver Physiol.* (2003) 285(2):G414-23), prevents gastric mucosal injury (Armando, et al. (2001) Peripheral administration of an angiotensin II AT(1) receptor antagonist decreases the hypothalamic-pituitary-adrenal response to isolation stress, *Endocrinology* 142 (9):3880-9) and restores modulation of HPA stress axis function. (Breiner (1984) Parents as change agents in the management of their developmentally delayed children's noncompliant behaviors: a critical review, *Appl. Res. Ment. Retard.* 5(2):259-78.) Both autistic children and insubordinate vervets experience social isolation and share non-compliance behaviors (Uno, et al., (1989) Hippocampal damage associated with prolonged and fatal stress in primates, *J. Neurosci.*, 9(5):1705-11), as well as hippocampal pathology. (Gandhi, et al. (2002) Interactions of human secretin with sterically stabilized phospholipid micelles amplify peptide-induced vasodilatation in vivo, *Peptides*, 23(8):1433-9.) Secretin, acting as a vasodilator (Helou, et al. (2003) Angiotensin receptor subtypes in thin and muscular juxtamedullary efferent arterioles of rat kidney, *Am. J. Physiol. Renal Physiol.* 285(3):F507-14), may modulate the effect of angiotensin II AT(1), a vasoconstrictor (Leong, et al. (2002) Restraint stress modulates brain, pituitary and adrenal expression of angiotensin II AT(1A), AT(1B) and AT(2) receptors. *Neuroendocrinology* 75(4):227-40), via "cross-talk" or interaction of peptides at the hypothalamic level. (Horvath, et al. (2002) Autism and gastrointestinal symptoms, *Curr. Gastroenterol. Rep.* 4(3):251-8.) If secretin modulates AT(1) receptors, such an interaction may underlie secretin's ameliorative effects on both GI pathology (Horvath, et al. (1998) Improved social and language skills after secretin administration in patients with autistic spectrum disorders, *J. Assoc. Acad. Minor Phys.* 9(1):9-15) and symptoms of autism. (Iijima, et al., Alteration of interleukin 4 production results in the inhibition of T helper type 2 cell-dominated inflammatory bowel disease in T cell receptor alpha chain-deficient mice, *J. Exp. Med.*, 1999 190(5):607-15.)

The fact that a S/OT peptide combination resolved visceral inflammation and brain activation in a cytokine (IL 10–/–) knockout mouse is of interest. Cytokines are dysregulated in both IBD (Dohi, et al., Hapten-induced colitis is associated with colonic patch hypertrophy and T helper cell 2-type responses, *J. Exp. Med.* (1999) 19; 189(8):1169-80; Kucharzik, et al., Synergistic effect of immunoregulatory cytokines on peripheral blood monocytes from patients with inflammatory bowel disease, *Dig. Dis. Sci.* (1997) 42(4): 805-12; Malek-Ahmadi P., Cytokines and etiopathogenesis of pervasive developmental disorders, *Med. Hypotheses* (2001) 56(3): 321-4) and autism. (Jyonouchi, et al., Proinflammatory and regulatory cytokine production associated with innate and adaptive immune responses in children with autism spectrum disorders and developmental regression, *J. Neuroimmunol.* (2001) 120(1-2):170-9; Jyonouchi, et al., Innate immunity associated with inflammatory responses and cytokine production against common dietary proteins in patients with autism spectrum disorder, *Neuropsychobiology* (2002) 46(2): 76-84; Yaraee, et al., Neuropeptides (SP and CGRP) augment pro-inflammatory cytokine production in HSV-infected macrophages, *Int. Immunopharmacol.* (2003) 3(13-14):1883-7.) Cytokines modulate peptide release and peptides modulate cytokine release (Manfredini, et al., Development of an IL-6 antagonist peptide that induces apoptosis in 7TD1 cells; Friebe-Hoffmann, et al., Effect of IL-1beta and IL-6 on oxytocin secretion in human uterine smooth muscle cells, *Am. J. Reprod. Immunol.* (2001) 46(3): 226-31; Asarian, et al., Stimuli from conspecifics influence brain mast cell population in male rats, *Horm. Behav.* (2002) 42(1): 1-12). Our data indicates that systemic S/OT largely compensates for the lack of IL-10 in the transgenic mouse, suggesting that peptide actions and cytokine actions may affect a common pathway, albeit at different points. In the face of chronic inflammatory conditions, the visceral brain is altered by both neural and humoral responses to a dysfunctional metabolic state. Peptides may be effective in treatment of chronic inflammatory disorders by reversing such imbalances of metabolism. The marked resolution of visceral inflammation and brain activation by peptides suggests that this treatment may apply to both acute and chronic inflammation. Furthermore, it is possible that visceral stress dysregulates cytokine/peptide interactions, and thus conditions and determines cognitive and emotional states, to a greater degree than previously thought.

The psychiatric ramifications of chronic inflammation are a result of the brain's capacity to sense, synthesize and react to inflammatory signals of neural and humoral origin. (Traub, et al., Noxious colorectal distention induced-c-Fos protein in limbic brain structures in the rat, *Neurosci. Lett.* (1996) 13; 215(3):165-8.) Chronic visceral stress is a potent dysregulator of cognitive/emotional brain regions. (Eskandari, et al., Neural immune pathways and their connection to inflammatory diseases, *Arthritis Res. Ther.* (2003) 5(6):251-65.) In fact, peripheral and central stress are inseparable, and are communicated neurohumorally. (McEwen, The neurobiology of stress: from serendipity to clinical relevance, *Brain Res.* (2000) 886(1-2):172-189.) Because peptide treatment appears to resolve gut inflammation and affected central areas simultaneously, peptides may be efficacious in treating a variety of inflammatory disorders and their resultant sickness behaviors, and lead to a new class of peptide treatments.

What is claimed is:

1. A method for treating inflammatory bowel disease in a subject, comprising administering to the subject a therapeutically effective amount of secretin and a therapeutically effective amount of oxytocin.

2. The method of claim 1, wherein the secretin and the oxytocin are administered concurrently.

3. The method of claim 1, wherein the secretin and the oxytocin are administered sequentially.

4. The method of claim 1, wherein the secretin and the oxytocin are administered together in a single combined formulation.

5. The method of claim 1, wherein the secretin and the oxytocin are administered in separate individual formulations.

6. The method of claim 1, wherein the secretin or the oxytocin are administered by an oral, inhalational, parenteral, intramuscular, intraperitoneal, intravascular, intravenous, subcutaneous or transdermal route.

7. The method of claim 1, wherein the secretin is administered at a dose of from about 0.001 mg per day to about 1000 mg/day.

8. The method of claim 1, wherein the secretin is administered at a dose of from about 1 mg per day to about 100 mg/day.

9. The method of claim 1, wherein the oxytocin is administered at a dose of from about 0.001 mg per day to about 1000 mg/day.

10. The method of claim 1, wherein the oxytocin is administered at a dose of from about 1 mg per day to about 100 mg/day.

11. The method of claim 1, wherein the subject is a human.

12. A method for treating primary biliary cirrhosis in a subject, comprising administering to the subject a therapeutically effective amount of secretin and a therapeutically effective amount of oxytocin.

13. The method of claim 12, wherein the secretin and the oxytocin are administered concurrently.

14. The method of claim 12, wherein the secretin and the oxytocin are administered sequentially.

15. The method of claim 12, wherein the secretin and the oxytocin are administered together in a single combined formulation.

16. The method of claim 12, wherein the secretin and the oxytocin are administered in separate individual formulations.

17. The method of claim 12, wherein the secretin or the oxytocin are administered by an oral, inhalational, parenteral, intramuscular, intraperitoneal, intravascular, intravenous, subcutaneous route or transdermal route.

18. The method of claim 12, wherein the secretin is administered at a dose of from about 0.001 mg per day to about 1000 mg/day.

19. The method of claim 12, wherein the secretin is administered at a dose of from about 1 mg per day to about 100 mg/day.

20. The method of claim 12, wherein the oxytocin is administered at a dose of from about 0.001 mg per day to about 1000 mg/day.

21. The method of claim 12, wherein the oxytocin is administered at a dose of from about 1 mg per day to about 100 mg/day.

22. The method of claim 12, wherein the subject is a human.

* * * * *